United States Patent
Quaedflieg et al.

(10) Patent No.: US 10,138,268 B2
(45) Date of Patent: Nov. 27, 2018

(54) PEPTIDE FRAGMENT CONDENSATION AND CYCLISATION USING A SUBTILISIN VARIANT WITH IMPROVED SYNTHESIS OVER HYDROLYSIS RATIO

(71) Applicant: ENZYPEP B.V., Geleen (NL)

(72) Inventors: Peter Jan Leonard Mario Quaedflieg, Geleen (NL); Timo Nuijens, Geleen (NL); Jan Metske Van Der Laan, Breda (NL); Dirk Barend Janssen, Groningen (NL); Ana Toplak, Groningen (NL); Bian Wu, Groningen (NL)

(73) Assignee: ENZYPEP B.V., Geleen (NL)

( * ) Notice: Subject to any disclaimer, the term of this patent is extended or adjusted under 35 U.S.C. 154(b) by 0 days.

(21) Appl. No.: 15/517,812

(22) PCT Filed: Oct. 9, 2015

(86) PCT No.: PCT/NL2015/050711
§ 371 (c)(1),
(2) Date: Apr. 7, 2017

(87) PCT Pub. No.: WO2016/056913
PCT Pub. Date: Apr. 14, 2016

(65) Prior Publication Data
US 2017/0305963 A1    Oct. 26, 2017

(30) Foreign Application Priority Data

Oct. 10, 2014 (WO) ................ PCT/NL2014/050707
Jun. 16, 2015 (WO) ................ PCT/NL2015/050441

(51) Int. Cl.
| | | |
|---|---|---|
| *C12N 9/48* | (2006.01) | |
| *C07K 1/02* | (2006.01) | |
| *C12P 21/02* | (2006.01) | |
| *C12N 9/54* | (2006.01) | |
| *C07K 1/36* | (2006.01) | |

(52) U.S. Cl.
CPC ............. *C07K 1/026* (2013.01); *C07K 1/36* (2013.01); *C12N 9/54* (2013.01); *C12P 21/02* (2013.01); *C12Y 304/21062* (2013.01)

(58) Field of Classification Search
CPC ........................................................ C07K 1/02
USPC .............................................. 435/7.72, 212
See application file for complete search history.

(56) References Cited

U.S. PATENT DOCUMENTS

| | | |
|---|---|---|
| 5,403,737 A | 4/1995 | Abrahmsen |
| 9,598,714 B2 * | 3/2017 | Quaedflieg ............. C07K 1/02 |

FOREIGN PATENT DOCUMENTS

| | | |
|---|---|---|
| WO | 1994018329 | 8/1994 |
| WO | 2005017110 A2 | 2/2005 |
| WO | 2010056640 A2 | 5/2010 |
| WO | 2011072099 A2 | 6/2011 |
| WO | 2011072099 A3 | 6/2011 |

OTHER PUBLICATIONS

Almogt, Orna, et al., Structural Basis of Thermostability, The Journal of Biological Chemistry, vol. 277, No. 30, 2002, pp. 27553-27558.
Chang, Thomas K., et al., Subtiligase: A tool for semisynthesis of proteins, Proc. Natl. Acad. Sci. USA, vol. 91, Dec. 1994, pp. 12544-12548.
Strausberg, Susan L., et al., Directed Coevolution of Stability and Catalytic Activity in Calcium-free Subtilisin, Biochemistry, 2005, vol. 44, pp. 3272-3279.
Jackson, David Y., et al., A Designed Peptide Ligase for Total Synthesis of Ribonuclease A with Unnatural Catalytic Residues, Science, Oct. 14, 1994, vol. 266, pp. 243-247.
Haring, Dietmar, et al., Straightforward development of stereoselective biocatalysts—from detergent to semisynthetic peroxidase selenosubtilisin, Journal of Molecular Catalysis B: Enzymatic 5, 1998, pp. 339-342.

* cited by examiner

*Primary Examiner* — Tekchand Saidha
(74) *Attorney, Agent, or Firm* — Gianna J. Arnold; Saul Ewing Arnstein & Lehr LLP

(57) ABSTRACT

The invention relates to a method for enzymatically synthesizing an (oligo)peptide, comprising coupling (a) an (oligo)peptide C-terminal ester or thioester and (b) an (oligo)peptide nucleophile having an N-terminally unprotected amine, wherein the coupling is carried out in a fluid comprising water, and wherein the coupling is catalyzed by a subtilisin BPN' variant or a homo-log thereof, which comprises the following mutations compared to subtilisin BPN' represented by SEQUENCE ID NO: 2 or a homolog sequence thereof: a deletion of the amino acids corresponding to positions 75-83; a mutation at the amino acid position corresponding to S221, the mutation being S221C or S221 selenocysteine; preferably a mutation at the amino acid position corresponding to P225 wherein the amino acid positions are defined according to the sequence of subtilisin BPN' represented by SEQUENCE ID NO: 2. Further, the invention relates to an enzyme suitable for use as a catalyst in a method of the invention.

20 Claims, 23 Drawing Sheets

Specification includes a Sequence Listing.

SEQUENCE LISTING

<160> NUMBER OF SEQ ID NOS: 115

<210> SEQ ID NO 1
<211> LENGTH: 1149
<212> TYPE: DNA
<213> ORGANISM: Bacillus amyloliquefaciens

<400> SEQUENCE: 1

```
gtgagaggca aaaagtatg  gatcagtttg  ctgtttgctt  tagcgttaat  ctttacgatg    60
gcgttcggca gcacatcctc tgcccaggcg gcagggaaat caaacgggga aaagaaatat   120
attgtcgggt ttaaacagac aatgagcacg atgagcgccg ctaagaagaa agatgtcatt   180
tctgaaaaag gcgggaaagt gcaaaagcaa ttcaaatatg tagacgcagc ttcagctaca   240
ttaaacgaaa aagctgtaaa agaattgaaa aaagacccga gcgtcgctta cgttgaagaa   300
gatcacgtag cacatgcgta cgcgcagtcc gtgccttacg gcgtatcaca aattaaagcc   360
cctgctctgc actctcaagg ctacactgga tcaaatgtta agtagcggt  tatcgacagc   420
ggtatcgatt cttctcatcc tgatttaaag gtagcaggcg gagccagcat ggttccttct   480
gaaacaaatc ctttccaaga caacaactct cacggaactc acgttgccgg cacagttgcg   540
gctcttaata actcaatcgg tgtattaggc gttgcgccaa gcgcatcact ttacgctgta   600
aaagttctcg gtgctgacgg ttccggccaa tacagctgga tcattaacgg aatcgagtgg   660
gcgatcgcaa acaatatgga cgttattaac atgagcctcg gcggaccttc tggttctgct   720
gctttaaaag cggcagttga taaagccgtt gcatccggcg tcgtagtcgt tgcggcagcc   780
ggtaacgaag gcacttccgg cagctcaagc acagtgggct accctggtaa ataccctct    840
gtcattgcag taggcgctgt tgacagcagc aaccaaagag catctttctc aagcgtagga   900
cctgagcttg atgtcatggc acctggcgta tctatccaaa gcacgcttcc tggaaacaaa   960
tacggggcgt acaacggtac gtcaatggca tctccgcacg ttgccggagc ggctgctttg  1020
attcttttcta agcacccgaa ctggacaaac actcaagtcc gcagcagttt agaaaacacc  1080
actacaaaac ttggtgattc tttctactat ggaaaagggc tgatcaacgt acaggcggca  1140
gctcagtaa                                                            1149
```

<210> SEQ ID NO 2
<211> LENGTH: 275
<212> TYPE: PRT
<213> ORGANISM: Bacillus amyloliquefaciens

<400> SEQUENCE: 2

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
        50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110
```

```
Trp Ala Ile Ala Asn Asn Met Asp Val Ile Asn Met Ser Leu Gly Gly
            115                 120                 125
Pro Ser Gly Ser Ala Ala Leu Lys Ala Ala Val Asp Lys Ala Val Ala
        130                 135                 140
Ser Gly Val Val Val Ala Ala Gly Asn Glu Gly Thr Ser Gly
145                 150                 155                 160
Ser Ser Ser Thr Val Gly Tyr Pro Gly Lys Tyr Pro Ser Val Ile Ala
                165                 170                 175
Val Gly Ala Val Asp Ser Ser Asn Gln Arg Ala Ser Phe Ser Ser Val
            180                 185                 190
Gly Pro Glu Leu Asp Val Met Ala Pro Gly Val Ser Ile Gln Ser Thr
        195                 200                 205
Leu Pro Gly Asn Lys Tyr Gly Ala Tyr Asn Gly Thr Ser Met Ala Ser
210                 215                 220
Pro His Val Ala Gly Ala Ala Ala Leu Ile Leu Ser Lys His Pro Asn
225                 230                 235                 240
Trp Thr Asn Thr Gln Val Arg Ser Ser Leu Glu Asn Thr Thr Thr Lys
                245                 250                 255
Leu Gly Asp Ser Phe Tyr Tyr Gly Lys Gly Leu Ile Asn Val Gln Ala
            260                 265                 270
Ala Ala Gln
        275

<210> SEQ ID NO 3
<211> LENGTH: 266
<212> TYPE: PRT
<213> ORGANISM: Artificial Sequence
<220> FEATURE:
<223> OTHER INFORMATION: subtilisin BPN' variant with deletion of Ca2+
      binding loop and S221C + P225A mutation

<400> SEQUENCE: 3

Ala Gln Ser Val Pro Tyr Gly Val Ser Gln Ile Lys Ala Pro Ala Leu
1               5                   10                  15
His Ser Gln Gly Tyr Thr Gly Ser Asn Val Lys Val Ala Val Ile Asp
            20                  25                  30
Ser Gly Ile Asp Ser Ser His Pro Asp Leu Lys Val Ala Gly Gly Ala
        35                  40                  45
Ser Met Val Pro Ser Glu Thr Asn Pro Phe Gln Asp Asn Asn Ser His
    50                  55                  60
Gly Thr His Val Ala Gly Thr Val Ala Ala Pro Ser Ala Ser
65                  70                  75                  80
Leu Tyr Ala Val Lys Val Leu Gly Ala Asp Gly Ser Gly Gln Tyr Ser
                85                  90                  95
Trp Ile Ile Asn Gly Ile Glu Trp Ala Ile Ala Asn Asn Met Asp Val
            100                 105                 110
Ile Asn Met Ser Leu Gly Gly Pro Ser Gly Ser Ala Ala Leu Lys Ala
        115                 120                 125
Ala Val Asp Lys Ala Val Ala Ser Gly Val Val Val Ala Ala Ala
    130                 135                 140
Gly Asn Glu Gly Thr Ser Gly Ser Ser Thr Val Gly Tyr Pro Gly
145                 150                 155                 160
Lys Tyr Pro Ser Val Ile Ala Val Gly Ala Val Asp Ser Ser Asn Gln
                165                 170                 175
Arg Ala Ser Phe Ser Ser Val Gly Pro Glu Leu Asp Val Met Ala Pro
            180                 185                 190
```

```
Gly Val Ser Ile Gln Ser Thr Leu Pro Gly Asn Lys Tyr Gly Ala Tyr
            195                 200                 205

Asn Gly Thr Cys Met Ala Ser Ala His Val Ala Gly Ala Ala Ala Leu
210                 215                 220

Ile Leu Ser Lys His Pro Asn Trp Thr Asn Thr Gln Val Arg Ser Ser
225                 230                 235                 240

Leu Glu Asn Thr Thr Thr Lys Leu Gly Asp Ser Phe Tyr Tyr Gly Lys
            245                 250                 255

Gly Leu Ile Asn Val Gln Ala Ala Ala Gln
            260                 265

<210> SEQ ID NO 4
<211> LENGTH: 266
<212> TYPE: PRT
<213> ORGANISM: Artificial Sequence
<220> FEATURE:
<223> OTHER INFORMATION: subtilisin BPN'variant with preferred mutation
      positions compared to SEQ ID NO 3
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (208)..(209)
```

```
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid

<400> SEQUENCE: 4

Ala Xaa Xaa Val Xaa Tyr Gly Val Xaa Gln Ile Lys Ala Pro Ala Leu
1               5                   10                  15

His Ser Gln Gly Tyr Thr Gly Ser Asn Val Lys Val Ala Val Xaa Asp
            20                  25                  30

Ser Gly Ile Asp Ser Ser His Pro Asp Leu Xaa Val Ala Gly Gly Ala
        35                  40                  45

Ser Xaa Val Pro Ser Glu Thr Asn Pro Phe Gln Asp Asn Asn Ser His
    50                  55                  60

Gly Thr His Val Ala Gly Thr Val Xaa Ala Val Ala Pro Ser Ala Ser
65                  70                  75                  80

Leu Tyr Ala Val Lys Val Leu Gly Ala Asp Gly Ser Gly Gln Tyr Ser
                85                  90                  95

Trp Ile Ile Asn Gly Ile Glu Trp Ala Ile Ala Asn Asn Met Asp Val
            100                 105                 110

Ile Asn Met Ser Leu Gly Gly Pro Ser Gly Ser Ala Ala Leu Lys Ala
        115                 120                 125

Ala Val Asp Lys Ala Val Ala Ser Gly Val Val Val Ala Ala Ala
    130                 135                 140

Gly Asn Xaa Gly Thr Ser Gly Ser Ser Ser Thr Val Xaa Tyr Pro Xaa
145                 150                 155                 160

Lys Tyr Pro Ser Val Ile Ala Val Gly Ala Val Asp Ser Ser Asn Gln
                165                 170                 175

Arg Ala Xaa Phe Ser Ser Val Gly Pro Glu Leu Asp Val Met Ala Pro
            180                 185                 190

Gly Val Ser Ile Xaa Ser Thr Leu Pro Gly Xaa Lys Tyr Gly Ala Xaa
        195                 200                 205

Xaa Gly Thr Cys Met Ala Ser Ala His Val Ala Gly Ala Ala Ala Leu
    210                 215                 220

Ile Leu Ser Lys His Pro Asn Trp Thr Asn Thr Gln Val Arg Ser Ser
225                 230                 235                 240

Leu Glu Asn Thr Xaa Thr Lys Leu Gly Asp Ser Phe Tyr Tyr Gly Lys
                245                 250                 255

Gly Leu Ile Asn Val Xaa Ala Ala Ala Gln
            260                 265

<210> SEQ ID NO 5
<211> LENGTH: 1595
<212> TYPE: DNA
<213> ORGANISM: Artificial Sequence
<220> FEATURE:
<223> OTHER INFORMATION: E. coli/B. subtilis shuttle vector pBES:
      Ptl149DM
<220> FEATURE:
<221> NAME/KEY: CDS
<222> LOCATION: (189)..(1337)

<400> SEQUENCE: 5
actagtgttc ttttctgtat gaaaatagtt atttcgagtc tctacggaaa tagcgagaga      60
```

-continued

```
tgatatacct aaatagagat aaaatcatct caaaaaaatg ggtctactaa aatattattc      120
catctattac aataaattca cagaatagtc ttttaagtaa gtctactctg aacttaagca      180 aaaggaga ggg acg cgt gtg aga ggc aaa aaa gta tgg atc agt ttg ctg      230
         Gly Thr Arg Val Arg Gly Lys Lys Val Trp Ile Ser Leu Leu
           1               5                  10 ttt gct tta gcg tta atc ttt acg atg gcg ttc ggc agc aca tcc tct      278
Phe Ala Leu Ala Leu Ile Phe Thr Met Ala Phe Gly Ser Thr Ser Ser
 15              20                  25                  30 gcc cag gcg gca ggg aaa tca aac ggg gaa aag aaa tat att gtc ggg      326
Ala Gln Ala Ala Gly Lys Ser Asn Gly Glu Lys Lys Tyr Ile Val Gly
                 35                  40                  45 ttt aaa cag aca atg agc acg atg agc gcc gct aag aag aaa gat gtc      374
Phe Lys Gln Thr Met Ser Thr Met Ser Ala Ala Lys Lys Lys Asp Val
             50                  55                  60 att tct gaa aaa ggc ggg aaa gtg caa aag caa ttc aaa tat gta gac      422
Ile Ser Glu Lys Gly Gly Lys Val Gln Lys Gln Phe Lys Tyr Val Asp
                 65                  70                  75 gca gct tca gct aca tta aac gaa aaa gct gta aaa gaa ttg aaa aaa      470
Ala Ala Ser Ala Thr Leu Asn Glu Lys Ala Val Lys Glu Leu Lys Lys
 80              85                  90 gac ccg agc gtc gct tac gtt gaa gaa gat cac gta gca cac gcg atg      518
Asp Pro Ser Val Ala Tyr Val Glu Glu Asp His Val Ala His Ala Met
 95                 100                 105                 110 gcg aag tgc gtg tct tac ggc gta gca caa att aaa gcc cct gct ctg      566
Ala Lys Cys Val Ser Tyr Gly Val Ala Gln Ile Lys Ala Pro Ala Leu
                115                 120                 125 cac tct caa ggc tac act gga tca aat gtt aaa gta gcg gtt ctt gac      614
His Ser Gln Gly Tyr Thr Gly Ser Asn Val Lys Val Ala Val Leu Asp
                130                 135                 140 agc ggt atc gat tct tct cat cct gat tta aac gta gca ggc gga gcc      662
Ser Gly Ile Asp Ser Ser His Pro Asp Leu Asn Val Ala Gly Gly Ala
            145                 150                 155 agc ttc gtt cct tct gaa aca aat cct ttc caa gac aac aac tct cac      710
Ser Phe Val Pro Ser Glu Thr Asn Pro Phe Gln Asp Asn Asn Ser His
160                 165                 170 gga act cac gtt gcc ggc aca gtt ttg gct gtt gcg cca agc gca tca      758
Gly Thr His Val Ala Gly Thr Val Leu Ala Val Ala Pro Ser Ala Ser
175                 180                 185                 190 ctt tac gct gta aaa gtt ctc ggt gct gac ggt tcc ggc caa tac agc      806
Leu Tyr Ala Val Lys Val Leu Gly Ala Asp Gly Ser Gly Gln Tyr Ser
                195                 200                 205 tgg atc att aac gga atc gag tgg gcg atc gca aac aat atg gac gtt      854
Trp Ile Ile Asn Gly Ile Glu Trp Ala Ile Ala Asn Asn Met Asp Val
                210                 215                 220 att aac atg agc ctc ggc gga cct tct ggt tct gct gct tta aaa gcg      902
Ile Asn Met Ser Leu Gly Gly Pro Ser Gly Ser Ala Ala Leu Lys Ala
            225                 230                 235 gca gtt gat aaa gcc gtt gca tcc ggc gtc gta gtc gtt gcg gca gcc      950
Ala Val Asp Lys Ala Val Ala Ser Gly Val Val Val Ala Ala Ala
240                 245                 250 ggt aac tct ggc act tcc ggc agc tca agc aca atg agc tac cct gct      998
Gly Asn Ser Gly Thr Ser Gly Ser Ser Ser Thr Val Ser Tyr Pro Ala
255                 260                 265                 270 aaa tac cct tct gtc att gca gta ggc gct gtt gac agc agc aac caa     1046
Lys Tyr Pro Ser Val Ile Ala Val Gly Ala Val Asp Ser Ser Asn Gln
                275                 280                 285 aga gca ccg ttc tca agc gta gga cct gag ctt gat gtc atg gca cct     1094
Arg Ala Pro Phe Ser Ser Val Gly Pro Glu Leu Asp Val Met Ala Pro
                290                 295                 300
```

```
ggc gta tct atc tgt agc acg ctt cct gga ggc aaa tac ggg gcg ctt      1142
Gly Val Ser Ile Cys Ser Thr Leu Pro Gly Gly Lys Tyr Gly Ala Leu
        305                 310                 315 tct ggt acg tgc atg gca tct gcg cac gtt gcc gga gcg gct gct ttg      1190
Ser Gly Thr Cys Met Ala Ser Ala His Val Ala Gly Ala Ala Ala Leu
320                 325                 330 att ctt tct aag cac ccg aac tgg aca aac act caa gtc cgc agc agt      1238
Ile Leu Ser Lys His Pro Asn Trp Thr Asn Thr Gln Val Arg Ser Ser
335                 340                 345                 350 tta gaa aac acc gct aca aaa ctt ggt gat tct ttc tac tat gga aaa      1286
Leu Glu Asn Thr Ala Thr Lys Leu Gly Asp Ser Phe Tyr Tyr Gly Lys
        355                 360                 365 ggg ctg atc aac gta gaa gcg gca gct cag cac cac cac cac cac cac      1334
Gly Leu Ile Asn Val Glu Ala Ala Ala Gln His His His His His His
            370                 375                 380 taa aacataaaaa accggccttg ccccgccgg tttttttatta ttttctcttcc         1387 tccgcatgtt caatccgctc cataatcgac ggatggctcc ctctgaaaat tttaacgaga   1447
aacggcgggt tgacccggct cagtcccgta acggccaagt cctgaaacgt ctcaatcgcc   1507
gcttcccggt ttccggtcag ctcaatgccg taacggtcgg cggcgttttc ctgataccgg   1567
gagacggcat tcgtaatcgg atggatcc                                      1595

<210> SEQ ID NO 6
<211> LENGTH: 382
<212> TYPE: PRT
<213> ORGANISM: Artificial Sequence
<220> FEATURE:
<223> OTHER INFORMATION: Synthetic Construct

<400> SEQUENCE: 6

Gly Thr Arg Val Arg Gly Lys Lys Val Trp Ile Ser Leu Leu Phe Ala
1               5                   10                  15

Leu Ala Leu Ile Phe Thr Met Ala Phe Gly Ser Thr Ser Ser Ala Gln
            20                  25                  30

Ala Ala Gly Lys Ser Asn Gly Glu Lys Lys Tyr Ile Val Gly Phe Lys
        35                  40                  45

Gln Thr Met Ser Thr Met Ser Ala Lys Lys Lys Asp Val Ile Ser
    50                  55                  60

Glu Lys Gly Gly Lys Val Gln Lys Gln Phe Lys Tyr Val Asp Ala Ala
65                  70                  75                  80

Ser Ala Thr Leu Asn Glu Lys Ala Val Lys Glu Leu Lys Lys Asp Pro
                85                  90                  95

Ser Val Ala Tyr Val Glu Glu Asp His Val Ala His Ala Met Ala Lys
            100                 105                 110

Cys Val Ser Tyr Gly Val Ala Gln Ile Lys Ala Pro Ala Leu His Ser
        115                 120                 125

Gln Gly Tyr Thr Gly Ser Asn Val Lys Val Ala Val Leu Asp Ser Gly
    130                 135                 140

Ile Asp Ser Ser His Pro Asp Leu Asn Val Ala Gly Gly Ala Ser Phe
145                 150                 155                 160

Val Pro Ser Glu Thr Asn Pro Phe Gln Asp Asn Asn Ser His Gly Thr
                165                 170                 175

His Val Ala Gly Thr Val Leu Ala Val Ala Pro Ser Ala Ser Leu Tyr
            180                 185                 190

Ala Val Lys Val Leu Gly Ala Asp Gly Ser Gly Gln Tyr Ser Trp Ile
        195                 200                 205
```

```
Ile Asn Gly Ile Glu Trp Ala Ile Ala Asn Asn Met Asp Val Ile Asn
        210                 215                 220

Met Ser Leu Gly Gly Pro Ser Gly Ser Ala Ala Leu Lys Ala Ala Val
225                 230                 235                 240

Asp Lys Ala Val Ala Ser Gly Val Val Val Ala Ala Gly Asn
                245                 250                 255

Ser Gly Thr Ser Gly Ser Ser Ser Thr Val Ser Tyr Pro Ala Lys Tyr
                260                 265                 270

Pro Ser Val Ile Ala Val Gly Ala Val Asp Ser Ser Asn Gln Arg Ala
                275                 280                 285

Pro Phe Ser Ser Val Gly Pro Glu Leu Asp Val Met Ala Pro Gly Val
        290                 295                 300

Ser Ile Cys Ser Thr Leu Pro Gly Gly Lys Tyr Gly Ala Leu Ser Gly
305                 310                 315                 320

Thr Cys Met Ala Ser Ala His Val Ala Gly Ala Ala Ala Leu Ile Leu
                325                 330                 335

Ser Lys His Pro Asn Trp Thr Asn Thr Gln Val Arg Ser Ser Leu Glu
                340                 345                 350

Asn Thr Ala Thr Lys Leu Gly Asp Ser Phe Tyr Tyr Gly Lys Gly Leu
                355                 360                 365

Ile Asn Val Glu Ala Ala Ala Gln His His His His His His
                370                 375                 380

<210> SEQ ID NO 7
<211> LENGTH: 5
<212> TYPE: PRT
<213> ORGANISM: Artificial Sequence
<220> FEATURE:
<223> OTHER INFORMATION: pentapeptide
<220> FEATURE:
<221> NAME/KEY: MOD_RES
<222> LOCATION: (5)..(5)
<223> OTHER INFORMATION: CAM-ester

<400> SEQUENCE: 7

Asp Phe Ser Lys Leu
1               5

<210> SEQ ID NO 8
<211> LENGTH: 5
<212> TYPE: PRT
<213> ORGANISM: Artificial Sequence
<220> FEATURE:
<223> OTHER INFORMATION: pentapeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: CAM ester

<400> SEQUENCE: 8

Asp Xaa Ser Lys Leu
1               5

<210> SEQ ID NO 9
<211> LENGTH: 5
<212> TYPE: PRT
<213> ORGANISM: Artificial Sequence
<220> FEATURE:
<223> OTHER INFORMATION: pentapeptide acyl donor
```

```
<220> FEATURE:
<221> NAME/KEY: MOD_RES
<222> LOCATION: (5)..(5)
<223> OTHER INFORMATION: CAM ester

<400> SEQUENCE: 9

Asp Leu Ser Lys Gln
1               5

<210> SEQ ID NO 10
<211> LENGTH: 7
<212> TYPE: PRT
<213> ORGANISM: Artificial Sequence
<220> FEATURE:
<223> OTHER INFORMATION: pentapeptide acyl donor
<220> FEATURE:
<221> NAME/KEY: MOD_RES
<222> LOCATION: (7)..(7)
<223> OTHER INFORMATION: CAM ester

<400> SEQUENCE: 10

Thr Ser Asp Leu Ser Lys Gln
1               5

<210> SEQ ID NO 11
<211> LENGTH: 9
<212> TYPE: PRT
<213> ORGANISM: Artificial Sequence
<220> FEATURE:
<223> OTHER INFORMATION: pentapeptide acyl donor
<220> FEATURE:
<221> NAME/KEY: MOD_RES
<222> LOCATION: (9)..(9)
<223> OTHER INFORMATION: CAM ester

<400> SEQUENCE: 11

Thr Phe Thr Ser Asp Leu Ser Lys Gln
1               5

<210> SEQ ID NO 12
<211> LENGTH: 11
<212> TYPE: PRT
<213> ORGANISM: Artificial Sequence
<220> FEATURE:
<223> OTHER INFORMATION: pentapeptide acyl donor
<220> FEATURE:
<221> NAME/KEY: MOD_RES
<222> LOCATION: (11)..(11)
<223> OTHER INFORMATION: CAM ester

<400> SEQUENCE: 12

Glu Gly Thr Phe Thr Ser Asp Leu Ser Lys Gln
1               5                   10

<210> SEQ ID NO 13
<211> LENGTH: 4
<212> TYPE: PRT
<213> ORGANISM: Artificial Sequence
<220> FEATURE:
<223> OTHER INFORMATION: peptide amine nucleophile

<400> SEQUENCE: 13

Ala Phe Ala Tyr
1

<210> SEQ ID NO 14
<211> LENGTH: 5
<212> TYPE: PRT
<213> ORGANISM: Artificial Sequence
```

```
<220> FEATURE:
<223> OTHER INFORMATION: peptide C-terminal CAM ester
<220> FEATURE:
<221> NAME/KEY: MOD_RES
<222> LOCATION: (4)..(4)
<223> OTHER INFORMATION: CAM ester
<220> FEATURE:
<221> NAME/KEY: MOD_RES
<222> LOCATION: (5)..(5)
<223> OTHER INFORMATION: CAM ester

<400> SEQUENCE: 14

Phe Ile Glu Trp Leu
1               5

<210> SEQ ID NO 15
<211> LENGTH: 13
<212> TYPE: PRT
<213> ORGANISM: Artificial Sequence
<220> FEATURE:
<223> OTHER INFORMATION: C-terminal CAM ester
<220> FEATURE:
<221> NAME/KEY: MOD_RES
<222> LOCATION: (13)..(13)
<223> OTHER INFORMATION: CAM ester

<400> SEQUENCE: 15

Ala Cys Lys Asn Gly Gln Thr Asn Cys Tyr Gln Ser Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: C-terminal amide
<220> FEATURE:
<221> NAME/KEY: MOD_RES
<222> LOCATION: (10)..(10)
<223> OTHER INFORMATION: AMIDATION

<400> SEQUENCE: 16

Ala Leu Met Lys Tyr Asn Ser Thr Glu Val
1               5                   10

<210> SEQ ID NO 17
<211> LENGTH: 13
<212> TYPE: PRT
<213> ORGANISM: Artificial Sequence
<220> FEATURE:
<223> OTHER INFORMATION: C-terminal CAM ester
<220> FEATURE:
<221> NAME/KEY: MOD_RES
<222> LOCATION: (1)..(1)
<223> OTHER INFORMATION: coupled to Fmoc
<220> FEATURE:
<221> NAME/KEY: MOD_RES
<222> LOCATION: (13)..(13)
<223> OTHER INFORMATION: CAM ester

<400> SEQUENCE: 17

His Ala Glu Gly Thr Phe Thr Ser Asp Leu Ser Lys Gln
1               5                   10

<210> SEQ ID NO 18
<211> LENGTH: 23
<212> TYPE: PRT
<213> ORGANISM: Artificial Sequence
<220> FEATURE:
<223> OTHER INFORMATION: condensed peptide
<220> FEATURE:
```

```
<221> NAME/KEY: MOD_RES
<222> LOCATION: (1)..(1)
<223> OTHER INFORMATION: Coupled to Fmoc
<220> FEATURE:
<221> NAME/KEY: MOD_RES
<222> LOCATION: (23)..(23)
<223> OTHER INFORMATION: AMIDATION

<400> SEQUENCE: 18

His Ala Glu Gly Thr Phe Thr Ser Asp Leu Ser Lys Gln Ala Leu Met
1               5                   10                  15

Lys Tyr Asn Ser Thr Glu Val
            20

<210> SEQ ID NO 19
<211> LENGTH: 8
<212> TYPE: PRT
<213> ORGANISM: Artificial Sequence
<220> FEATURE:
<223> OTHER INFORMATION: condensed product

<400> SEQUENCE: 19

His Ala Glu Gly Thr Ala Leu Arg
1               5

<210> SEQ ID NO 20
<211> LENGTH: 5
<212> TYPE: PRT
<213> ORGANISM: Artificial Sequence
<220> FEATURE:
<223> OTHER INFORMATION: C-terminal CAM ester
<220> FEATURE:
<221> NAME/KEY: MOD_RES
<222> LOCATION: (5)..(5)
<223> OTHER INFORMATION: CAM ester

<400> SEQUENCE: 20

His Ala Glu Gly Thr
1               5

<210> SEQ ID NO 21
<211> LENGTH: 8
<212> TYPE: PRT
<213> ORGANISM: Artificial Sequence
<220> FEATURE:
<223> OTHER INFORMATION: condensed peptide

<400> SEQUENCE: 21

Asp Phe Ser Lys Leu Ala Leu Arg
1               5

<210> SEQ ID NO 22
<211> LENGTH: 6
<212> TYPE: PRT
<213> ORGANISM: Artificial Sequence
<220> FEATURE:
<223> OTHER INFORMATION: condensed paptide
<220> FEATURE:
<221> NAME/KEY: MOD_RES
<222> LOCATION: (5)..(5)
<223> OTHER INFORMATION: CAM ester

<400> SEQUENCE: 22

Asp Phe Ser Lys Leu Lys
1               5

<210> SEQ ID NO 23
<211> LENGTH: 4
```

```
<212> TYPE: PRT
<213> ORGANISM: Artificial Sequence
<220> FEATURE:
<223> OTHER INFORMATION: C-terminal thioester
<220> FEATURE:
<221> NAME/KEY: MOD_RES
<222> LOCATION: (1)..(1)
<223> OTHER INFORMATION: coupled tosuccinyl
<220> FEATURE:
<221> NAME/KEY: MOD_RES
<222> LOCATION: (4)..(4)
<223> OTHER INFORMATION: thio-ester

<400> SEQUENCE: 23

Ala Ala Pro Phe
1

<210> SEQ ID NO 24
<211> LENGTH: 4
<212> TYPE: PRT
<213> ORGANISM: Artificial Sequence
<220> FEATURE:
<223> OTHER INFORMATION: C-terminal CAM ester
<220> FEATURE:
<221> NAME/KEY: MOD_RES
<222> LOCATION: (4)..(4)
<223> OTHER INFORMATION: CAM ester

<400> SEQUENCE: 24

Asp Ser Lys Leu
1

<210> SEQ ID NO 25
<211> LENGTH: 5
<212> TYPE: PRT
<213> ORGANISM: Artificial Sequence
<220> FEATURE:
<223> OTHER INFORMATION: C-terminal CAM ester
<220> FEATURE:
<221> NAME/KEY: MOD_RES
<222> LOCATION: (5)..(5)
<223> OTHER INFORMATION: CAM ester

<400> SEQUENCE: 25

Asp Phe Ser Leu Lys
1               5

<210> SEQ ID NO 26
<211> LENGTH: 6
<212> TYPE: PRT
<213> ORGANISM: Artificial Sequence
<220> FEATURE:
<223> OTHER INFORMATION: condensed peptide
<220> FEATURE:
<221> NAME/KEY: MOD_RES
<222> LOCATION: (5)..(5)
<223> OTHER INFORMATION: CAM ester

<400> SEQUENCE: 26

Asp Phe Ser Lys Leu Leu
1               5

<210> SEQ ID NO 27
<211> LENGTH: 46
<212> TYPE: PRT
<213> ORGANISM: Bacillus amyloliquefaciens

<400> SEQUENCE: 27

Pro Phe Gln Asp Asn Asn Ser His Gly Thr His Val Ala Gly Thr Val
1               5                   10                  15
```

```
Ala Ala Leu Asn Asn Ser Ile Gly Val Leu Gly Val Ala Pro Ser Ala
            20                  25                  30

Ser Leu Tyr Ala Val Lys Val Leu Gly Ala Asp Gly Ser Gly
        35                  40                  45

<210> SEQ ID NO 28
<211> LENGTH: 37
<212> TYPE: PRT
<213> ORGANISM: Artificial Sequence
<220> FEATURE:
<223> OTHER INFORMATION: Subtilisin variant

<400> SEQUENCE: 28

Pro Phe Gln Asp Asn Asn Ser His Gly Thr His Val Ala Gly Thr Val
1               5                   10                  15

Leu Ala Val Ala Pro Ser Ala Ser Leu Tyr Ala Val Lys Val Leu Gly
            20                  25                  30

Ala Asp Gly Ser Gly
        35

<210> SEQ ID NO 29
<211> LENGTH: 46
<212> TYPE: PRT
<213> ORGANISM: Artificial Sequence
<220> FEATURE:
<223> OTHER INFORMATION: Subtilisin variant

<400> SEQUENCE: 29

Pro Phe Gln Asp Asn Asn Ser His Gly Thr His Val Ala Gly Thr Ala
1               5                   10                  15

Ala Ala Leu Asn Asn Ser Val Gly Val Leu Gly Val Ala Pro Ser Ala
            20                  25                  30

Ser Leu Tyr Ala Val Lys Val Leu Gly Ala Asp Gly Ser Gly
        35                  40                  45

<210> SEQ ID NO 30
<211> LENGTH: 46
<212> TYPE: PRT
<213> ORGANISM: Artificial Sequence
<220> FEATURE:
<223> OTHER INFORMATION: Subtilisin variant

<400> SEQUENCE: 30

Pro Phe Gln Asp Asn Asn Ser His Gly Thr His Val Ala Gly Thr Val
1               5                   10                  15

Ala Ala Leu Asn Asn Ser Val Gly Val Leu Gly Val Ala Pro Ser Ala
            20                  25                  30

Ser Leu Tyr Ala Val Lys Val Leu Gly Ala Asp Gly Ser Gly
        35                  40                  45

<210> SEQ ID NO 31
<211> LENGTH: 46
<212> TYPE: PRT
<213> ORGANISM: Artificial Sequence
<220> FEATURE:
<223> OTHER INFORMATION: Subtilisin variant

<400> SEQUENCE: 31

Pro Phe Gln Asp Tyr Asn Ser His Gly Thr His Val Ala Gly Thr Val
1               5                   10                  15

Ala Ala Leu Asn Asn Ser Val Gly Val Leu Gly Val Ala Pro Ser Ala
            20                  25                  30
```

```
Ser Leu Tyr Ala Val Lys Val Leu Gly Ala Asp Gly Ser Gly
        35                  40                  45

<210> SEQ ID NO 32
<211> LENGTH: 46
<212> TYPE: PRT
<213> ORGANISM: Artificial Sequence
<220> FEATURE:
<223> OTHER INFORMATION: Subtilisin variant

<400> SEQUENCE: 32

Pro Phe Gln Asp Arg Asn Ser His Gly Thr His Val Ala Gly Thr Val
1               5                   10                  15

Ala Ala Leu Asn Asn Ser Val Gly Val Leu Gly Val Ala Pro Ser Ala
            20                  25                  30

Ser Leu Tyr Ala Val Lys Val Leu Gly Ala Asp Gly Ser Gly
        35                  40                  45

<210> SEQ ID NO 33
<211> LENGTH: 46
<212> TYPE: PRT
<213> ORGANISM: Artificial Sequence
<220> FEATURE:
<223> OTHER INFORMATION: Subtilisin variant

<400> SEQUENCE: 33

Pro Phe Gln Asp Asn Asn Ser His Gly Thr His Val Ala Gly Thr Val
1               5                   10                  15

Ala Ala Leu Asn Asn Ser Val Gly Val Leu Gly Val Ser Pro Ser Ala
            20                  25                  30

Ser Leu Tyr Ala Val Lys Val Leu Gly Ala Asp Gly Ser Gly
        35                  40                  45

<210> SEQ ID NO 34
<211> LENGTH: 46
<212> TYPE: PRT
<213> ORGANISM: Artificial Sequence
<220> FEATURE:
<223> OTHER INFORMATION: Subtilisin variant

<400> SEQUENCE: 34

Pro Phe Gln Asp Asn Asn Ser His Gly Thr His Val Ala Gly Thr Val
1               5                   10                  15

Ala Ala Leu Asn Asn Ser Ile Gly Val Leu Gly Val Ala Pro Ser Ala
            20                  25                  30

Ser Leu Tyr Ala Val Lys Val Leu Gly Ala Asp Gly Ser Gly
        35                  40                  45

<210> SEQ ID NO 35
<211> LENGTH: 46
<212> TYPE: PRT
<213> ORGANISM: Artificial Sequence
<220> FEATURE:
<223> OTHER INFORMATION: Subtilisin variant

<400> SEQUENCE: 35

Pro Phe Gln Asp Asn Asn Ser His Gly Thr His Val Ala Gly Thr Val
1               5                   10                  15

Ala Ala Leu Asn Asn Ser Val Arg Val Leu Gly Gly Ala Pro Ser Ala
            20                  25                  30

Ser Leu Tyr Ala Val Lys Val Leu Gly Ala Asp Gly Ser Gly
        35                  40                  45
```

```
<210> SEQ ID NO 36
<211> LENGTH: 46
<212> TYPE: PRT
<213> ORGANISM: Artificial Sequence
<220> FEATURE:
<223> OTHER INFORMATION: Subtilisin variant

<400> SEQUENCE: 36

Pro Phe Gln Asp Asn Asn Ser His Gly Thr His Val Ala Gly Thr Val
1               5                   10                  15

Ala Ala Leu Asn Asn Ser Val Phe Val Leu Gly Val Ala Pro Ser Ala
            20                  25                  30

Ser Leu Tyr Ala Val Lys Val Leu Gly Ala Asp Gly Ser Gly
        35                  40                  45

<210> SEQ ID NO 37
<211> LENGTH: 46
<212> TYPE: PRT
<213> ORGANISM: Artificial Sequence
<220> FEATURE:
<223> OTHER INFORMATION: Subtilisin variant

<400> SEQUENCE: 37

Pro Phe Gln Asp Gly Asn Ser His Gly Thr His Val Ala Gly Thr Val
1               5                   10                  15

Ala Ala Leu Asn Asn Ser Val Gly Val Leu Gly Val Ala Pro Ser Ala
            20                  25                  30

Ser Leu Tyr Ala Val Lys Val Leu Ser Ser Gly Ser Gly
        35                  40                  45

<210> SEQ ID NO 38
<211> LENGTH: 46
<212> TYPE: PRT
<213> ORGANISM: Artificial Sequence
<220> FEATURE:
<223> OTHER INFORMATION: Subtilisin variant

<400> SEQUENCE: 38

Pro Tyr Gln Asp Gly Ser Ser His Gly Thr His Val Ala Gly Thr Val
1               5                   10                  15

Ala Ala Leu Asn Asn Ser Ile Gly Val Leu Gly Val Ala Pro Asn Ala
            20                  25                  30

Ser Leu Tyr Ala Val Lys Val Leu Asp Ser Thr Gly Asn Gly
        35                  40                  45

<210> SEQ ID NO 39
<211> LENGTH: 46
<212> TYPE: PRT
<213> ORGANISM: Artificial Sequence
<220> FEATURE:
<223> OTHER INFORMATION: Subtilisin variant

<400> SEQUENCE: 39

Pro Tyr Gln Asp Gly Ser Ser His Gly Thr His Ala Ala Gly Thr Ile
1               5                   10                  15

Ala Ala Leu Asn Asn Ser Ile Gly Val Leu Gly Val Ala Pro Ser Ala
            20                  25                  30

Ser Leu Tyr Ala Val Lys Val Leu Asp Ser Thr Gly Ser Gly
        35                  40                  45

<210> SEQ ID NO 40
```

```
<211> LENGTH: 46
<212> TYPE: PRT
<213> ORGANISM: Artificial Sequence
<220> FEATURE:
<223> OTHER INFORMATION: Subtilisin variant

<400> SEQUENCE: 40

Pro Tyr Gln Asp Gly Ser Ser His Gly Thr His Val Ala Gly Thr Ile
1               5                   10                  15

Ala Ala Leu Asn Asn Ser Ile Gly Val Leu Gly Val Ala Pro Ser Ala
            20                  25                  30

Ser Leu Tyr Ala Val Lys Val Leu Asp Ser Thr Gly Ser Gly
        35                  40                  45

<210> SEQ ID NO 41
<211> LENGTH: 46
<212> TYPE: PRT
<213> ORGANISM: Artificial Sequence
<220> FEATURE:
<223> OTHER INFORMATION: Subtilisin variant

<400> SEQUENCE: 41

Pro Tyr Gln Asp Gly Ser Ser His Gly Thr His Val Ala Gly Thr Ile
1               5                   10                  15

Ala Ala Leu Asn Asn Ser Ile Gly Val Leu Gly Val Ala Pro Asn Ala
            20                  25                  30

Ser Leu Tyr Ala Val Lys Val Leu Asp Ser Thr Gly Ser Gly
        35                  40                  45

<210> SEQ ID NO 42
<211> LENGTH: 46
<212> TYPE: PRT
<213> ORGANISM: Artificial Sequence
<220> FEATURE:
<223> OTHER INFORMATION: Subtilisin variant

<400> SEQUENCE: 42

Pro Tyr Gln Asp Gly Ser Ser His Gly Thr His Val Ala Gly Thr Ile
1               5                   10                  15

Ala Ala Leu Asn Asn Ser Ile Gly Val Leu Gly Val Ala Pro Ser Ser
            20                  25                  30

Ala Leu Tyr Ala Val Lys Val Leu Asp Ser Thr Gly Ser Gly
        35                  40                  45

<210> SEQ ID NO 43
<211> LENGTH: 46
<212> TYPE: PRT
<213> ORGANISM: Artificial Sequence
<220> FEATURE:
<223> OTHER INFORMATION: Subtilisin variant

<400> SEQUENCE: 43

Pro Tyr Gln Asp Gly Ser Ser His Gly Thr His Val Thr Gly Thr Ile
1               5                   10                  15

Ala Ala Leu Asn Asn Ser Ile Gly Val Leu Gly Val Ala Pro Ser Ala
            20                  25                  30

Ser Leu Tyr Ala Val Lys Val Leu Asp Ser Thr Gly Ser Gly
        35                  40                  45

<210> SEQ ID NO 44
<211> LENGTH: 46
<212> TYPE: PRT
<213> ORGANISM: Artificial Sequence
```

```
<220> FEATURE:
<223> OTHER INFORMATION: Subtilisin variant

<400> SEQUENCE: 44

Pro Tyr Gln Asp Gly Ser Ser His Gly Thr His Val Ala Gly Thr Val
1               5                   10                  15

Ala Ala Leu Asn Asn Thr Ile Gly Val Leu Gly Val Ala Pro Ser Ala
            20                  25                  30

Ser Leu Tyr Ala Val Lys Val Leu Asp Ser Thr Gly Ser Gly
        35                  40                  45

<210> SEQ ID NO 45
<211> LENGTH: 46
<212> TYPE: PRT
<213> ORGANISM: Artificial Sequence
<220> FEATURE:
<223> OTHER INFORMATION: Subtilisin variant

<400> SEQUENCE: 45

Pro Tyr Gln Asp Gly Ser Ser His Gly Thr His Val Ala Gly Thr Ile
1               5                   10                  15

Ala Ala Leu Asn Asn Thr Ile Gly Val Leu Gly Val Ala Pro Ser Ala
            20                  25                  30

Ser Leu Tyr Ala Val Lys Val Leu Asp Ser Thr Gly Ser Gly
        35                  40                  45

<210> SEQ ID NO 46
<211> LENGTH: 46
<212> TYPE: PRT
<213> ORGANISM: Artificial Sequence
<220> FEATURE:
<223> OTHER INFORMATION: Subtilisin variant

<400> SEQUENCE: 46

Pro Tyr Gln Asp Gly Ser Ser His Gly Thr His Val Ala Gly Thr Ile
1               5                   10                  15

Ala Ala Leu Asn Asn Ser Ile Gly Val Leu Gly Val Ala Pro Ser Ala
            20                  25                  30

Ser Leu Tyr Ala Val Ile Val Leu Asp Ser Thr Gly Ser Gly
        35                  40                  45

<210> SEQ ID NO 47
<211> LENGTH: 46
<212> TYPE: PRT
<213> ORGANISM: Artificial Sequence
<220> FEATURE:
<223> OTHER INFORMATION: Subtilisin variant

<400> SEQUENCE: 47

Pro Tyr Gln Asp Gly Ser Ser His Gly Thr His Val Ala Gly Thr Ile
1               5                   10                  15

Ala Ala Leu Asn Asn Ser Ile Gly Val Leu Gly Val Ala Pro Ser Ala
            20                  25                  30

Ser Leu Tyr Ala Val Lys Val Leu Asp Ser Pro Gly Ser Gly
        35                  40                  45

<210> SEQ ID NO 48
<211> LENGTH: 46
<212> TYPE: PRT
<213> ORGANISM: Artificial Sequence
<220> FEATURE:
<223> OTHER INFORMATION: Subtilisin variant
```

-continued

<400> SEQUENCE: 48

Pro Tyr Gln Asp Gly Ser Ser His Gly Thr His Val Ala Gly Thr Ile
1               5                   10                  15

Ala Ala Leu Asn Asn Ser Ile Gly Val Leu Gly Val Ala Pro Asn Ala
            20                  25                  30

Ser Leu Tyr Ala Val Lys Val Leu Asp Ser Ser Gly Ser Gly
        35                  40                  45

<210> SEQ ID NO 49
<211> LENGTH: 46
<212> TYPE: PRT
<213> ORGANISM: Artificial Sequence
<220> FEATURE:
<223> OTHER INFORMATION: Subtilisin variant

<400> SEQUENCE: 49

Pro Tyr Gln Asp Gly Ser Ser His Gly Thr His Val Ala Gly Thr Ile
1               5                   10                  15

Ala Ala Leu Asn Asn Ser Ile Cys Val Leu Gly Val Ala Pro Ser Ala
            20                  25                  30

Ser Leu Tyr Ala Val Lys Val Leu Asp Ser Thr Gly Ser Gly
        35                  40                  45

<210> SEQ ID NO 50
<211> LENGTH: 46
<212> TYPE: PRT
<213> ORGANISM: Artificial Sequence
<220> FEATURE:
<223> OTHER INFORMATION: Subtilisin variant

<400> SEQUENCE: 50

Pro Tyr Gln Gly Gly Ser Ser His Gly Thr His Val Ala Gly Thr Ile
1               5                   10                  15

Ser Ala Phe Asn Asn Ser Ile Gly Val Leu Gly Val Ala Pro Asn Ala
            20                  25                  30

Ser Leu Tyr Ala Val Lys Val Leu Asp Ser Thr Gly Ser Gly
        35                  40                  45

<210> SEQ ID NO 51
<211> LENGTH: 46
<212> TYPE: PRT
<213> ORGANISM: Artificial Sequence
<220> FEATURE:
<223> OTHER INFORMATION: Subtilisin variant

<400> SEQUENCE: 51

Ala Thr Gln Asp Phe Gln Ser His Gly Thr His Val Ala Gly Thr Ile
1               5                   10                  15

Ala Ala Leu Asp Asn Thr Ile Gly Val Leu Gly Val Ala Pro Ser Ala
            20                  25                  30

Ser Leu Tyr Ala Val Lys Val Leu Asp Arg Asn Gly Asp Gly
        35                  40                  45

<210> SEQ ID NO 52
<211> LENGTH: 46
<212> TYPE: PRT
<213> ORGANISM: Artificial Sequence
<220> FEATURE:
<223> OTHER INFORMATION: Subtilisin variant

<400> SEQUENCE: 52

Pro Tyr Gln Gly Arg Ser Ser His Gly Thr His Val Ala Gly Thr Ile

```
                1               5                  10                  15
Ala Ala Ser Phe Thr Ser Thr Gly Val Leu Gly Val Pro Pro Ser Ala
                    20                  25                  30

Ser Ser Tyr Pro Ser Lys Ala His Ser Ser Ser Gln Ser Ala
            35                  40                  45

<210> SEQ ID NO 53
<211> LENGTH: 46
<212> TYPE: PRT
<213> ORGANISM: Artificial Sequence
<220> FEATURE:
<223> OTHER INFORMATION: Subtilisin variant

<400> SEQUENCE: 53

Ala Thr Gln Asp Phe Gln Ser His Gly Thr His Val Ala Gly Thr Ile
1               5                  10                  15

Ala Ala Leu Asp Asn Thr Ile Gly Val Leu Gly Val Ala Pro Asn Ala
                    20                  25                  30

Ser Leu Tyr Ala Val Lys Val Leu Asp Arg Asn Gly Asp Gly
            35                  40                  45

<210> SEQ ID NO 54
<211> LENGTH: 46
<212> TYPE: PRT
<213> ORGANISM: Artificial Sequence
<220> FEATURE:
<223> OTHER INFORMATION: Subtilisin variant

<400> SEQUENCE: 54

Ala Thr Gln Asp Phe Gln Ser His Gly Thr His Val Ala Gly Thr Ile
1               5                  10                  15

Ala Ala Leu Asp Asn Thr Ile Gly Val Leu Gly Val Ala Pro Ser Ala
                    20                  25                  30

Ser Leu Tyr Ala Val Lys Val Leu Asp Arg Asn Gly Asp Gly
            35                  40                  45

<210> SEQ ID NO 55
<211> LENGTH: 46
<212> TYPE: PRT
<213> ORGANISM: Artificial Sequence
<220> FEATURE:
<223> OTHER INFORMATION: Subtilisin variant

<400> SEQUENCE: 55

Ala Thr Gln Asp Phe Gln Ser His Gly Thr His Val Ala Gly Thr Ile
1               5                  10                  15

Ala Ala Leu Asp Asn Thr Ile Gly Val Leu Gly Val Ala Pro Ser Ala
                    20                  25                  30

Ser Leu Tyr Ala Val Lys Val Leu Asp Arg Tyr Gly Asp Gly
            35                  40                  45

<210> SEQ ID NO 56
<211> LENGTH: 46
<212> TYPE: PRT
<213> ORGANISM: Artificial Sequence
<220> FEATURE:
<223> OTHER INFORMATION: Subtilisin variant

<400> SEQUENCE: 56

Ala Thr Gln Asp Phe Gln Ser His Gly Thr His Val Ala Gly Thr Ile
1               5                  10                  15

Ala Ala Leu Asp Asn Thr Ile Gly Val Leu Gly Val Ala Pro Ser Ala
```

```
                20                  25                  30

Ser Leu Tyr Ala Val Lys Ala Leu Asp Arg Asn Gly Asp Gly
        35                  40                  45

<210> SEQ ID NO 57
<211> LENGTH: 46
<212> TYPE: PRT
<213> ORGANISM: Artificial Sequence
<220> FEATURE:
<223> OTHER INFORMATION: Subtilisin variant

<400> SEQUENCE: 57

Pro Thr Gln Asp Gly Ser Ser His Gly Thr His Val Ala Gly Thr Val
1               5                   10                  15

Ala Ala Leu Asn Asn Thr Ile Gly Val Leu Gly Val Ala Pro Asn Ala
            20                  25                  30

Ser Leu Tyr Ala Val Lys Val Leu Asp Ser Thr Ser Asp Gly
        35                  40                  45

<210> SEQ ID NO 58
<211> LENGTH: 46
<212> TYPE: PRT
<213> ORGANISM: Artificial Sequence
<220> FEATURE:
<223> OTHER INFORMATION: Subtilisin variant

<400> SEQUENCE: 58

Tyr Asn Thr Asp Gly Asn Gly His Gly Thr His Val Ala Gly Thr Ile
1               5                   10                  15

Ala Ala Leu Asp Asn Thr Thr Gly Val Leu Gly Val Ala Pro Asn Val
            20                  25                  30

Ser Leu Tyr Ala Ile Lys Val Leu Asn Ser Ser Gly Ser Gly
        35                  40                  45

<210> SEQ ID NO 59
<211> LENGTH: 46
<212> TYPE: PRT
<213> ORGANISM: Artificial Sequence
<220> FEATURE:
<223> OTHER INFORMATION: Subtilisin variant

<400> SEQUENCE: 59

Tyr Asn Thr Asp Gly Asn Gly His Gly Thr His Val Ala Gly Thr Ile
1               5                   10                  15

Ala Ala Leu Asp Asn Thr Thr Gly Val Leu Gly Val Ala Pro Ser Val
            20                  25                  30

Ser Leu Tyr Ala Ile Lys Val Leu Asn Ser Ser Gly Ser Gly
        35                  40                  45

<210> SEQ ID NO 60
<211> LENGTH: 46
<212> TYPE: PRT
<213> ORGANISM: Artificial Sequence
<220> FEATURE:
<223> OTHER INFORMATION: Subtilisin variant

<400> SEQUENCE: 60

Pro Tyr Ile Asp Ser Asn Gly His Gly Thr His Val Ala Gly Thr Ile
1               5                   10                  15

Ala Ala Leu Asn Asn Thr Val Gly Val Leu Gly Val Ala Tyr Asn Ala
            20                  25                  30

Glu Leu Tyr Ala Ile Lys Val Leu Ser Ala Ser Gly Ser Gly
```

<210> SEQ ID NO 61
<211> LENGTH: 46
<212> TYPE: PRT
<213> ORGANISM: Artificial Sequence
<220> FEATURE:
<223> OTHER INFORMATION: Subtilisin variant

<400> SEQUENCE: 61

Tyr Asn Thr Asp Gly Asn Gly His Gly Thr His Val Ala Gly Thr Ile
1               5                   10                  15

Ala Ala Leu Asp Asn Thr Thr Gly Val Leu Gly Val Ala Pro Ser Val
            20                  25                  30

Ser Leu Tyr Ala Ile Lys Val Leu Asn Ser Ser Gly Ser Gly
        35                  40                  45

<210> SEQ ID NO 62
<211> LENGTH: 46
<212> TYPE: PRT
<213> ORGANISM: Artificial Sequence
<220> FEATURE:
<223> OTHER INFORMATION: Subtilisin variant

<400> SEQUENCE: 62

Tyr Asn Thr Asp Gly Asn Gly His Gly Thr His Val Ala Gly Thr Ile
1               5                   10                  15

Ala Ala Leu Asp Asn Thr Thr Gly Val Leu Gly Val Ala Pro Ser Val
            20                  25                  30

Ser Leu Phe Ala Ile Lys Val Leu Asn Ser Ser Gly Ser Gly
        35                  40                  45

<210> SEQ ID NO 63
<211> LENGTH: 46
<212> TYPE: PRT
<213> ORGANISM: Artificial Sequence
<220> FEATURE:
<223> OTHER INFORMATION: Subtilisin variant

<400> SEQUENCE: 63

Tyr Asn Thr Asp Gly His Gly His Gly Thr His Val Ala Gly Thr Ile
1               5                   10                  15

Ala Ala Leu Asp Asn Thr Thr Gly Val Leu Gly Val Ala Pro Ser Val
            20                  25                  30

Ser Leu Tyr Ala Ile Lys Val Leu Asn Ser Ser Gly Ser Gly
        35                  40                  45

<210> SEQ ID NO 64
<211> LENGTH: 46
<212> TYPE: PRT
<213> ORGANISM: Artificial Sequence
<220> FEATURE:
<223> OTHER INFORMATION: Subtilisin variant

<400> SEQUENCE: 64

Ala Leu Gln Asp Gly Asn Gly His Gly Thr His Val Ala Gly Thr Ile
1               5                   10                  15

Ala Ala Leu Asp Asn Gln Val Gly Val Leu Gly Val Ala Tyr Asp Val
            20                  25                  30

Asp Leu Tyr Ala Ile Lys Val Leu Gly Ala Asp Gly Ser Gly
        35                  40                  45

-continued

<210> SEQ ID NO 65
<211> LENGTH: 46
<212> TYPE: PRT
<213> ORGANISM: Artificial Sequence
<220> FEATURE:
<223> OTHER INFORMATION: Subtilisin variant

<400> SEQUENCE: 65

```
Ala Leu Gln Asp Gly Asn Gly His Gly Thr His Val Ala Gly Thr Ile
1               5                   10                  15

Ala Ala Leu Asp Asn Thr Thr Gly Val Leu Gly Val Ala Tyr Asn Ala
            20                  25                  30

Asp Leu Tyr Ala Ile Lys Val Leu Ser Ala Ser Gly Ser Gly
        35                  40                  45
```

<210> SEQ ID NO 66
<211> LENGTH: 46
<212> TYPE: PRT
<213> ORGANISM: Artificial Sequence
<220> FEATURE:
<223> OTHER INFORMATION: Subtilisin variant

<400> SEQUENCE: 66

```
Pro Phe Val Asp Pro His Lys His Gly Thr His Val Ala Gly Thr Ile
1               5                   10                  15

Ala Ala Leu Asp Asn Lys Val Gly Val Val Gly Val Ala Pro Lys Ala
            20                  25                  30

Ser Ile Tyr Ala Val Lys Val Ala Asp Glu Asn Gly Asp Gly
        35                  40                  45
```

<210> SEQ ID NO 67
<211> LENGTH: 46
<212> TYPE: PRT
<213> ORGANISM: Artificial Sequence
<220> FEATURE:
<223> OTHER INFORMATION: Subtilisin variant

<400> SEQUENCE: 67

```
Tyr Asn Thr Asp Gly Asn Gly His Gly Thr His Val Ala Gly Thr Val
1               5                   10                  15

Ala Ala Leu Asp Asn Thr Thr Gly Val Leu Gly Val Ala Pro Ser Val
            20                  25                  30

Ser Leu Tyr Ala Ile Lys Val Leu Asn Ser Ser Gly Ser Gly
        35                  40                  45
```

<210> SEQ ID NO 68
<211> LENGTH: 46
<212> TYPE: PRT
<213> ORGANISM: Artificial Sequence
<220> FEATURE:
<223> OTHER INFORMATION: Subtilisin variant

<400> SEQUENCE: 68

```
Pro Leu Ile Asp Pro His Glu His Gly Thr His Val Ala Gly Thr Ile
1               5                   10                  15

Ala Ala Leu Asp Asn Lys Val Gly Val Val Gly Val Ala Pro Lys Ala
            20                  25                  30

Ser Ile Tyr Ala Val Lys Val Ala Asp Glu Asn Gly Asp Gly
        35                  40                  45
```

<210> SEQ ID NO 69
<211> LENGTH: 46
<212> TYPE: PRT

<213> ORGANISM: Artificial Sequence
<220> FEATURE:
<223> OTHER INFORMATION: Subtilisin variant

<400> SEQUENCE: 69

```
Ala Leu Thr Asp Gly Asn Gly His Gly Thr His Val Ala Gly Thr Ile
1               5                   10                  15

Ala Ala Leu Asn Asn Asn Val Gly Val Leu Gly Val Ser Tyr Asp Val
            20                  25                  30

Asp Leu Tyr Ala Val Lys Val Leu Ser Ala Gly Gly Ser Gly
        35                  40                  45
```

<210> SEQ ID NO 70
<211> LENGTH: 46
<212> TYPE: PRT
<213> ORGANISM: Artificial Sequence
<220> FEATURE:
<223> OTHER INFORMATION: Subtilisin variant

<400> SEQUENCE: 70

```
Pro Leu Val Asp Pro His Glu His Gly Thr His Val Ala Gly Thr Ile
1               5                   10                  15

Ala Ala Leu Asp Asn Lys Val Gly Val Val Gly Val Ala Pro Lys Ala
            20                  25                  30

Ser Ile Tyr Ala Val Lys Val Ala Asp Glu Asn Gly Asp Gly
        35                  40                  45
```

<210> SEQ ID NO 71
<211> LENGTH: 46
<212> TYPE: PRT
<213> ORGANISM: Artificial Sequence
<220> FEATURE:
<223> OTHER INFORMATION: Subtilisin variant

<400> SEQUENCE: 71

```
Tyr Asn Thr Asp Gly Asn Gly His Gly Thr His Val Ala Gly Thr Val
1               5                   10                  15

Ala Ala Leu Asp Asn Thr Thr Gly Val Leu Gly Val Ala Pro Ser Val
            20                  25                  30

Ser Leu Tyr Ala Val Lys Val Leu Asn Ser Ser Gly Ser Gly
        35                  40                  45
```

<210> SEQ ID NO 72
<211> LENGTH: 46
<212> TYPE: PRT
<213> ORGANISM: Artificial Sequence
<220> FEATURE:
<223> OTHER INFORMATION: Subtilisin variant

<400> SEQUENCE: 72

```
Ser Thr Gln Asp Gly Asn Gly His Gly Thr His Val Ala Gly Thr Ile
1               5                   10                  15

Ala Ala Leu Asn Asn Ser Ile Gly Val Leu Gly Val Ala Pro Ser Ala
            20                  25                  30

Glu Leu Tyr Ala Val Lys Val Leu Gly Ala Asp Gly Arg Gly
        35                  40                  45
```

<210> SEQ ID NO 73
<211> LENGTH: 46
<212> TYPE: PRT
<213> ORGANISM: Artificial Sequence
<220> FEATURE:
<223> OTHER INFORMATION: Subtilisin variant

<400> SEQUENCE: 73

Ser Thr Gln Asp Gly Asn Gly His Gly Thr His Val Ala Gly Thr Ile
1               5                   10                  15

Ala Ala Leu Asn Asn Ser Ile Gly Val Leu Gly Val Ala Pro Ser Ala
            20                  25                  30

Glu Leu Tyr Ala Val Lys Val Leu Gly Ala Ser Gly Ser Gly
        35                  40                  45

<210> SEQ ID NO 74
<211> LENGTH: 46
<212> TYPE: PRT
<213> ORGANISM: Artificial Sequence
<220> FEATURE:
<223> OTHER INFORMATION: Subtilisin variant

<400> SEQUENCE: 74

Ser Thr Gln Asp Gly Asn Gly His Gly Thr His Val Ala Gly Thr Ile
1               5                   10                  15

Ala Ala Leu Asn Asn Ser Ile Gly Val Leu Gly Val Ala Pro Asn Ala
            20                  25                  30

Glu Leu Tyr Ala Val Lys Val Leu Gly Ala Ser Gly Ser Gly
        35                  40                  45

<210> SEQ ID NO 75
<211> LENGTH: 46
<212> TYPE: PRT
<213> ORGANISM: Artificial Sequence
<220> FEATURE:
<223> OTHER INFORMATION: Subtilisin variant

<400> SEQUENCE: 75

Asn Ile Ser Asp Gly Asn Gly His Gly Thr His Val Ala Gly Thr Ile
1               5                   10                  15

Ala Ala Leu Asn Asn Ser Ile Gly Val Leu Gly Val Ala Pro Asn Val
            20                  25                  30

Asp Leu Tyr Gly Val Lys Val Leu Gly Ala Ser Gly Ser Gly
        35                  40                  45

<210> SEQ ID NO 76
<211> LENGTH: 46
<212> TYPE: PRT
<213> ORGANISM: Artificial Sequence
<220> FEATURE:
<223> OTHER INFORMATION: Subtilisin variant

<400> SEQUENCE: 76

Asn Ile Ser Asp Gly Asn Gly His Gly Thr His Val Ala Gly Thr Ile
1               5                   10                  15

Ala Ala Leu Asn Asn Ser Ile Gly Val Ile Gly Val Ala Pro Asn Val
            20                  25                  30

Asp Leu Tyr Gly Val Lys Val Leu Gly Ala Ser Gly Cys Gly
        35                  40                  45

<210> SEQ ID NO 77
<211> LENGTH: 46
<212> TYPE: PRT
<213> ORGANISM: Artificial Sequence
<220> FEATURE:
<223> OTHER INFORMATION: Subtilisin variant

<400> SEQUENCE: 77

```
Asn Ile Ser Asp Gly Thr Gly His Gly Thr His Val Ala Gly Thr Ile
1               5                   10                  15

Ala Ala Leu Asn Asn Ser Ile Gly Val Leu Gly Val Ala Pro Asn Val
            20                  25                  30

Asp Leu Tyr Gly Val Lys Val Leu Gly Ala Ser Gly Ser Gly
        35                  40                  45
```

<210> SEQ ID NO 78
<211> LENGTH: 46
<212> TYPE: PRT
<213> ORGANISM: Artificial Sequence
<220> FEATURE:
<223> OTHER INFORMATION: Subtilisin variant

<400> SEQUENCE: 78

```
Thr Tyr Val Asp Tyr Asn Gly His Gly Thr His Val Ala Gly Thr Val
1               5                   10                  15

Ala Ala Leu Asn Asn Ser Tyr Gly Val Leu Gly Val Ala Pro Gly Ala
            20                  25                  30

Glu Leu Tyr Ala Val Lys Val Leu Asp Arg Asn Gly Ser Gly
        35                  40                  45
```

<210> SEQ ID NO 79
<211> LENGTH: 46
<212> TYPE: PRT
<213> ORGANISM: Artificial Sequence
<220> FEATURE:
<223> OTHER INFORMATION: Subtilisin variant

<400> SEQUENCE: 79

```
Asn Ile Ser Asp Gly Asn Gly His Gly Thr Gln Val Ala Gly Thr Ile
1               5                   10                  15

Ala Ala Leu Asn Asn Ser Ile Gly Val Leu Gly Val Ala Pro Asn Val
            20                  25                  30

Asp Leu Tyr Gly Val Lys Val Leu Gly Ala Ser Gly Ser Gly
        35                  40                  45
```

<210> SEQ ID NO 80
<211> LENGTH: 46
<212> TYPE: PRT
<213> ORGANISM: Artificial Sequence
<220> FEATURE:
<223> OTHER INFORMATION: Subtilisin variant

<400> SEQUENCE: 80

```
Thr Thr Ala Asp Leu Asn Gly His Gly Thr His Val Ala Gly Thr Val
1               5                   10                  15

Ala Ala Leu Asn Asn Ser Ile Gly Val Ile Gly Val Ala Pro Asn Ala
            20                  25                  30

Glu Leu Tyr Ala Val Lys Val Leu Gly Ala Asn Gly Ser Gly
        35                  40                  45
```

<210> SEQ ID NO 81
<211> LENGTH: 46
<212> TYPE: PRT
<213> ORGANISM: Artificial Sequence
<220> FEATURE:
<223> OTHER INFORMATION: Subtilisin variant

<400> SEQUENCE: 81

```
Pro Tyr Tyr Asp Gly Ser Gly His Gly Thr His Val Ala Gly Thr Val
1               5                   10                  15
```

```
Ala Ala Leu Asn Asn Ser Val Gly Val Gly Val Ala Tyr Asn Ala
            20                  25                  30

Glu Leu Tyr Ala Val Lys Val Leu Asn Ser Gly Ser Gly
        35                  40                  45

<210> SEQ ID NO 82
<211> LENGTH: 46
<212> TYPE: PRT
<213> ORGANISM: Artificial Sequence
<220> FEATURE:
<223> OTHER INFORMATION: Subtilisin variant

<400> SEQUENCE: 82

Ser Tyr Gln Asp Gly Asn Gly His Gly Thr His Val Ala Gly Thr Ile
1               5                   10                  15

Ala Ala Leu Asn Asn Ser Ile Gly Val Val Gly Val Ala Pro Asn Ala
            20                  25                  30

Glu Leu Tyr Ala Val Lys Val Leu Gly Ala Asn Gly Ser Gly
        35                  40                  45

<210> SEQ ID NO 83
<211> LENGTH: 46
<212> TYPE: PRT
<213> ORGANISM: Artificial Sequence
<220> FEATURE:
<223> OTHER INFORMATION: Subtilisin variant

<400> SEQUENCE: 83

Thr Tyr Val Asp Tyr Asn Gly His Gly Thr His Val Ala Gly Thr Val
1               5                   10                  15

Ala Ala Leu Asn Asn Ser Tyr Gly Val Leu Gly Val Ala Pro Gly Ala
            20                  25                  30

Glu Leu Tyr Ala Val Lys Val Leu Asp Arg Asn Gly Ser Gly
        35                  40                  45

<210> SEQ ID NO 84
<211> LENGTH: 46
<212> TYPE: PRT
<213> ORGANISM: Artificial Sequence
<220> FEATURE:
<223> OTHER INFORMATION: Subtilisin variant

<400> SEQUENCE: 84

Thr Met Leu Asp Gly Asn Gly His Gly Thr His Val Ala Gly Thr Ile
1               5                   10                  15

Ala Ala Leu Asn Asn Asn Val Gly Val Leu Gly Val Ala Pro Asn Val
            20                  25                  30

Glu Leu Tyr Gly Val Lys Val Leu Gly Ala Asn Gly Ser Gly
        35                  40                  45

<210> SEQ ID NO 85
<211> LENGTH: 46
<212> TYPE: PRT
<213> ORGANISM: Artificial Sequence
<220> FEATURE:
<223> OTHER INFORMATION: Subtilisin variant

<400> SEQUENCE: 85

Ser Tyr Gln Asp Tyr Asn Gly His Gly Thr His Val Ala Gly Thr Ile
1               5                   10                  15

Ala Gly Leu Asn Asn Ser Tyr Gly Val Leu Gly Val Ala Pro Asn Val
            20                  25                  30
```

Asn Leu Tyr Ala Val Lys Val Leu Asp Arg Asn Gly Ser Gly
            35                  40                  45

<210> SEQ ID NO 86
<211> LENGTH: 46
<212> TYPE: PRT
<213> ORGANISM: Artificial Sequence
<220> FEATURE:
<223> OTHER INFORMATION: Subtilisin variant

<400> SEQUENCE: 86

Gly Ala Asp Asp Gly Asn Gly His Gly Thr His Val Ala Gly Thr Ile
1               5                   10                  15

Ala Ala Leu Asp Asn Asp Glu Gly Val Leu Gly Val Ala Pro Glu Val
            20                  25                  30

Asp Leu Phe Ala Val Lys Val Leu Ser Ala Ser Gly Ser Gly
            35                  40                  45

<210> SEQ ID NO 87
<211> LENGTH: 46
<212> TYPE: PRT
<213> ORGANISM: Artificial Sequence
<220> FEATURE:
<223> OTHER INFORMATION: Subtilisin variant

<400> SEQUENCE: 87

Thr Ile Ala Asp Gly Asn Gly His Gly Thr His Val Ala Gly Thr Ile
1               5                   10                  15

Ala Ala Leu Asn Asn Asn Val Gly Val Leu Gly Val Ala Pro Asn Val
            20                  25                  30

Glu Leu Tyr Gly Val Lys Val Leu Gly Ala Asn Gly Ser Gly
            35                  40                  45

<210> SEQ ID NO 88
<211> LENGTH: 46
<212> TYPE: PRT
<213> ORGANISM: Artificial Sequence
<220> FEATURE:
<223> OTHER INFORMATION: Subtilisin variant

<400> SEQUENCE: 88

Ser Tyr His Asp Asn Asn Gly His Gly Thr His Val Ala Gly Thr Ile
1               5                   10                  15

Ala Ala Leu Asn Asn Ser Ile Gly Val Leu Gly Val Ala Pro Ser Ala
            20                  25                  30

Asp Leu Tyr Ala Val Lys Val Leu Asp Arg Asn Gly Ser Gly
            35                  40                  45

<210> SEQ ID NO 89
<211> LENGTH: 46
<212> TYPE: PRT
<213> ORGANISM: Artificial Sequence
<220> FEATURE:
<223> OTHER INFORMATION: Subtilisin variant

<400> SEQUENCE: 89

Pro Tyr Tyr Asp Ala Asn Gly His Gly Thr His Val Ala Gly Thr Val
1               5                   10                  15

Ala Ala Val Asn Asn Asn Leu Gly Val Leu Gly Val Ala Tyr Gln Ala
            20                  25                  30

Asp Leu Tyr Ala Val Lys Val Leu Asn Asn Asp Gly Ser Gly
            35                  40                  45

<210> SEQ ID NO 90
<211> LENGTH: 46
<212> TYPE: PRT
<213> ORGANISM: Artificial Sequence
<220> FEATURE:
<223> OTHER INFORMATION: Subtilisin variant

<400> SEQUENCE: 90

```
Ser Thr His Asp Gly Asn Ala His Gly Thr Gln Val Ala Gly Thr Ile
1               5                   10                  15

Ala Ala Leu Asn Asn Ser Ile Gly Val Leu Gly Val Ala Pro Asn Ala
            20                  25                  30

Glu Leu Tyr Ala Val Asn Val Ile Gly Ala Ser Gly Ser Gly
        35                  40                  45
```

<210> SEQ ID NO 91
<211> LENGTH: 46
<212> TYPE: PRT
<213> ORGANISM: Artificial Sequence
<220> FEATURE:
<223> OTHER INFORMATION: Subtilisin variant

<400> SEQUENCE: 91

```
Pro Phe Phe Asp Gly Asp Gly His Gly Thr His Val Ala Gly Thr Val
1               5                   10                  15

Ala Ala Val Asn Asn Asp Ile Gly Val Val Gly Val Ala Ser Glu Ala
            20                  25                  30

Asp Leu Tyr Ala Val Lys Val Leu Asn Asn Ala Gly Ser Gly
        35                  40                  45
```

<210> SEQ ID NO 92
<211> LENGTH: 46
<212> TYPE: PRT
<213> ORGANISM: Artificial Sequence
<220> FEATURE:
<223> OTHER INFORMATION: Subtilisin variant

<400> SEQUENCE: 92

```
Pro Phe Phe Asp Gly Asp Gly His Gly Thr His Val Ala Gly Thr Val
1               5                   10                  15

Ala Ala Val Asn Asn Asp Ile Gly Val Val Gly Val Ala Ser Glu Ala
            20                  25                  30

Asp Leu Tyr Ala Val Lys Val Leu Asn Asn Ala Gly Ser Gly
        35                  40                  45
```

<210> SEQ ID NO 93
<211> LENGTH: 46
<212> TYPE: PRT
<213> ORGANISM: Artificial Sequence
<220> FEATURE:
<223> OTHER INFORMATION: Subtilisin variant

<400> SEQUENCE: 93

```
Pro Tyr Asn Asp Val Gln Gly His Gly Thr His Val Ala Gly Thr Ile
1               5                   10                  15

Ala Ala Arg Asn Asn Ser Val Gly Val Ile Gly Val Ala Tyr Asn Ala
            20                  25                  30

Gln Leu Tyr Ala Val Lys Val Leu Asn Asn Gln Gly Ser Gly
        35                  40                  45
```

<210> SEQ ID NO 94
<211> LENGTH: 46

```
<212> TYPE: PRT
<213> ORGANISM: Artificial Sequence
<220> FEATURE:
<223> OTHER INFORMATION: Subtilisin variant

<400> SEQUENCE: 94

Pro Tyr Gln Asp Gly Ser Ser His Gly Thr His Val Ala Gly Thr Val
1               5                   10                  15

Ala Ala Leu Asn Asn Ser Ile Gly Val Leu Gly Val Ala Pro Asn Ala
            20                  25                  30

Ser Leu Tyr Ala Val Lys Val Leu Asp Ser Thr Gly Asn Gly
        35                  40                  45

<210> SEQ ID NO 95
<211> LENGTH: 46
<212> TYPE: PRT
<213> ORGANISM: Artificial Sequence
<220> FEATURE:
<223> OTHER INFORMATION: Subtilisin variant

<400> SEQUENCE: 95

Asn Tyr Asn Asp Asp Phe Gly His Gly Thr Arg Val Ala Gly Val Ile
1               5                   10                  15

Ala Ala Leu Asp Asn Asn Lys Gly Val Leu Gly Met Ala Pro Leu Ser
            20                  25                  30

Glu Ile Tyr Ala Ile Lys Val Leu Asp Ala Arg Gly Lys Gly
        35                  40                  45

<210> SEQ ID NO 96
<211> LENGTH: 46
<212> TYPE: PRT
<213> ORGANISM: Artificial Sequence
<220> FEATURE:
<223> OTHER INFORMATION: Subtilisin variant

<400> SEQUENCE: 96

Phe Tyr Arg Asp Leu Asn Gly His Gly Thr His Val Ala Gly Thr Ile
1               5                   10                  15

Ala Ala Gln Glu Asn Asp Glu Ala Ser Thr Gly Ile Ala Pro Asn Val
            20                  25                  30

Glu Leu Tyr Ala Val Lys Val Leu Asn Gly Leu Gly Ala Gly
        35                  40                  45

<210> SEQ ID NO 97
<211> LENGTH: 46
<212> TYPE: PRT
<213> ORGANISM: Artificial Sequence
<220> FEATURE:
<223> OTHER INFORMATION: Subtilisin variant

<400> SEQUENCE: 97

Asn Tyr Asn Asp Asp Tyr Gly His Gly Thr Arg Val Ala Gly Val Ile
1               5                   10                  15

Ser Ala Leu Asp Asn Asn Lys Gly Val Leu Gly Met Ala Pro Leu Ser
            20                  25                  30

Glu Ile Tyr Ala Ile Lys Val Leu Asp Ala Arg Gly Lys Gly
        35                  40                  45

<210> SEQ ID NO 98
<211> LENGTH: 46
<212> TYPE: PRT
<213> ORGANISM: Artificial Sequence
<220> FEATURE:
```

<223> OTHER INFORMATION: Subtilisin variant

<400> SEQUENCE: 98

Asp Tyr Met Asp Tyr Asn Gly His Gly Thr His Val Ala Gly Thr Val
1               5                   10                  15

Ala Ala Leu Asp Asn Asn Ser Gly Val Val Gly Val Ala Pro Asp Ala
            20                  25                  30

Asn Leu Phe Ala Gly Lys Val Leu Asp Asp Gly Ser Gly
        35                  40                  45

<210> SEQ ID NO 99
<211> LENGTH: 46
<212> TYPE: PRT
<213> ORGANISM: Artificial Sequence
<220> FEATURE:
<223> OTHER INFORMATION: Subtilisin variant

<400> SEQUENCE: 99

Ser Tyr Thr Asp Asp Asn Gly His Gly Thr His Val Ala Gly Ile Ile
1               5                   10                  15

Gly Ala Lys Asn Asn Ser Tyr Gly Thr Val Gly Val Ala Asn Asp Ala
            20                  25                  30

Ser Leu Tyr Ala Val Lys Val Leu Gly Ser Asp Gly Ser Gly
        35                  40                  45

<210> SEQ ID NO 100
<211> LENGTH: 45
<212> TYPE: PRT
<213> ORGANISM: Artificial Sequence
<220> FEATURE:
<223> OTHER INFORMATION: Subtilisin variant

<400> SEQUENCE: 100

Pro Met Asp Asp His Ser His Gly Thr His Val Ala Gly Ile Val Val
1               5                   10                  15

Ala Ala Ser Asn Gly Ile Gly Val Leu Gly Ala Ala Pro His Ala Gly
            20                  25                  30

Leu Tyr Ser Val Lys Val Ala Asp Ser Ser Gly Tyr Cys
        35                  40                  45

<210> SEQ ID NO 101
<211> LENGTH: 46
<212> TYPE: PRT
<213> ORGANISM: Artificial Sequence
<220> FEATURE:
<223> OTHER INFORMATION: Subtilisin variant

<400> SEQUENCE: 101

Ser Tyr Leu Asp Asp Asn Gly His Gly Thr His Val Ala Gly Ile Ile
1               5                   10                  15

Gly Ala Lys Asn Asn Gly Tyr Gly Ile Val Gly Val Ala Asn Glu Ala
            20                  25                  30

Ser Leu Tyr Ala Ile Lys Val Leu Gly Asn Asp Gly Ala Gly
        35                  40                  45

<210> SEQ ID NO 102
<211> LENGTH: 45
<212> TYPE: PRT
<213> ORGANISM: Artificial Sequence
<220> FEATURE:
<223> OTHER INFORMATION: Subtilisin variant

<400> SEQUENCE: 102

```
Pro Met Asp Asp Gln Gly His Gly Thr His Cys Ala Gly Thr Ile Ala
1               5                   10                  15

Ala Ala Ile Asn Gly Ala Gly Val Val Gly Val Ala Pro Gln Ala Ser
            20                  25                  30

Leu Tyr Ala Ala Lys Val Leu Asp Arg Asn Gly Ser Gly
        35                  40                  45

<210> SEQ ID NO 103
<211> LENGTH: 46
<212> TYPE: PRT
<213> ORGANISM: Artificial Sequence
<220> FEATURE:
<223> OTHER INFORMATION: Subtilisin variant

<400> SEQUENCE: 103

Ser Tyr Ala Asp Asp Asn Gly His Gly Thr His Val Ala Gly Ile Ile
1               5                   10                  15

Gly Ala Arg Asn Asn Ser Ile Gly Thr Val Gly Ile Ala His Glu Ala
            20                  25                  30

Ser Ile Tyr Ala Val Lys Ala Leu Glu Ala Asn Gly Ser Gly
        35                  40                  45

<210> SEQ ID NO 104
<211> LENGTH: 45
<212> TYPE: PRT
<213> ORGANISM: Artificial Sequence
<220> FEATURE:
<223> OTHER INFORMATION: Subtilisin variant

<400> SEQUENCE: 104

Pro Met Asp Asp His Ser His Gly Thr His Val Ala Gly Thr Val Ala
1               5                   10                  15

Ala Leu Ser Asn Asp Ile Gly Val Leu Gly Ala Ala Pro Gln Ala Gly
            20                  25                  30

Leu Tyr Ala Val Lys Val Ala Asp Ser Ser Gly Ser Cys
        35                  40                  45

<210> SEQ ID NO 105
<211> LENGTH: 46
<212> TYPE: PRT
<213> ORGANISM: Artificial Sequence
<220> FEATURE:
<223> OTHER INFORMATION: Subtilisin variant

<400> SEQUENCE: 105

Ser Tyr Asn Asp Asp Asn Gly His Gly Thr His Val Ala Gly Ile Ile
1               5                   10                  15

Ala Ala Lys Asn Asn Arg Ile Gly Val Leu Gly Val Ala Pro Glu Ala
            20                  25                  30

Ser Ile Tyr Ala Val Lys Val Leu Asn Arg Phe Gly Glu Gly
        35                  40                  45

<210> SEQ ID NO 106
<211> LENGTH: 46
<212> TYPE: PRT
<213> ORGANISM: Artificial Sequence
<220> FEATURE:
<223> OTHER INFORMATION: Subtilisin variant

<400> SEQUENCE: 106

Pro Ser Tyr Asp Gly Val Gly His Gly Thr His Val Ala Gly Thr Ile
1               5                   10                  15
```

```
Ala Ala Lys Asp Asn Gly Tyr Gly Val Val Gly Val Ala Pro Asp Ala
            20                  25                  30

Asn Ile His Ser Ala Lys Val Leu Asp Ser Gln Gly Tyr Gly
            35                  40                  45

<210> SEQ ID NO 107
<211> LENGTH: 46
<212> TYPE: PRT
<213> ORGANISM: Artificial Sequence
<220> FEATURE:
<223> OTHER INFORMATION: Subtilisin variant

<400> SEQUENCE: 107

Ala Tyr Asn Asp Asp Asn Gly His Gly Thr His Val Ala Gly Ile Ile
1               5                   10                  15

Ala Ala Lys Asn Asn His Ile Gly Val Leu Gly Val Ala Pro Glu Ala
            20                  25                  30

Ser Ile Tyr Ala Val Lys Val Leu Asp Arg Phe Gly Glu Gly
            35                  40                  45

<210> SEQ ID NO 108
<211> LENGTH: 46
<212> TYPE: PRT
<213> ORGANISM: Artificial Sequence
<220> FEATURE:
<223> OTHER INFORMATION: Subtilisin variant

<400> SEQUENCE: 108

Ser Tyr Ala Asp Asp Asn Gly His Gly Thr His Val Ala Gly Ile Ile
1               5                   10                  15

Gly Ala Arg Asn Asn Ser Ile Gly Thr Val Gly Ile Ala His Glu Ala
            20                  25                  30

Ser Ile Tyr Ala Val Lys Ala Leu Glu Ala Asn Gly Ser Gly
            35                  40                  45

<210> SEQ ID NO 109
<211> LENGTH: 46
<212> TYPE: PRT
<213> ORGANISM: Artificial Sequence
<220> FEATURE:
<223> OTHER INFORMATION: Subtilisin variant

<400> SEQUENCE: 109

Pro Phe Gln Asp Asn Asn Ser His Gly Thr His Val Ala Gly Thr Val
1               5                   10                  15

Ala Ala Leu Asn Asn Ser Val Gly Val Leu Gly Val Ala Pro Ser Ala
            20                  25                  30

Ser Leu Tyr Ala Val Lys Val Leu Gly Ala Asp Gly Ser Gly
            35                  40                  45

<210> SEQ ID NO 110
<211> LENGTH: 46
<212> TYPE: PRT
<213> ORGANISM: Artificial Sequence
<220> FEATURE:
<223> OTHER INFORMATION: Subtilisin variant

<400> SEQUENCE: 110

Ser Tyr Ala Asp Asp Asn Gly His Gly Thr His Val Ala Gly Ile Ile
1               5                   10                  15

Ala Ala Arg Asn Asn Gly Ile Gly Thr Val Gly Ile Ala His Glu Ala
            20                  25                  30
```

-continued

Ser Leu Tyr Ala Val Lys Ala Leu Glu Ala Asn Gly Ser Gly
        35                  40                  45

<210> SEQ ID NO 111
<211> LENGTH: 46
<212> TYPE: PRT
<213> ORGANISM: Artificial Sequence
<220> FEATURE:
<223> OTHER INFORMATION: Subtilisin variant

<400> SEQUENCE: 111

Ser Phe Asp Asp Asn Gly His Gly Thr His Leu Ala Gly Ile Val
1               5                   10                  15

Ala Ala Gln Asp Asn Glu Leu Gly Met Thr Gly Ile Ala Pro Asn Val
            20                  25                  30

Asp Leu Tyr Ala Val Lys Val Leu Asp Lys Tyr Thr Asn Gly
        35                  40                  45

<210> SEQ ID NO 112
<211> LENGTH: 46
<212> TYPE: PRT
<213> ORGANISM: Artificial Sequence
<220> FEATURE:
<223> OTHER INFORMATION: Subtilisin variant

<400> SEQUENCE: 112

Ser Tyr Gln Asp Asp Asn Gly His Gly Thr His Val Ala Gly Ile Ile
1               5                   10                  15

Ala Ala Lys Asp Asn Asp Ile Gly Thr Val Gly Val Ala Pro Asn Ala
            20                  25                  30

Ser Ile Tyr Ala Val Lys Val Leu Asp Arg Tyr Gly Glu Gly
        35                  40                  45

<210> SEQ ID NO 113
<211> LENGTH: 46
<212> TYPE: PRT
<213> ORGANISM: Artificial Sequence
<220> FEATURE:
<223> OTHER INFORMATION: Subtilisin variant

<400> SEQUENCE: 113

Ser Tyr Gln Asp Asp Asn Gly His Gly Thr His Val Ala Gly Ile Ile
1               5                   10                  15

Ala Ala Lys Asp Asn Asn Ile Gly Ser Val Gly Val Ala Pro Gly Ala
            20                  25                  30

Ser Val Tyr Ala Leu Lys Val Leu Asp Arg Tyr Gly Glu Gly
        35                  40                  45

<210> SEQ ID NO 114
<211> LENGTH: 46
<212> TYPE: PRT
<213> ORGANISM: Artificial Sequence
<220> FEATURE:
<223> OTHER INFORMATION: Subtilisin variant

<400> SEQUENCE: 114

Ser Phe Asp Asp Asn Gly His Gly Thr His Leu Ala Gly Ile Val
1               5                   10                  15

Ala Ala Gln Asp Asn Glu Leu Gly Met Thr Gly Ile Ala Pro Asn Val
            20                  25                  30

Asp Leu Tyr Ala Val Lys Val Leu Asp Lys Tyr Thr Asn Gly
        35                  40                  45

```
<210> SEQ ID NO 115
<211> LENGTH: 46
<212> TYPE: PRT
<213> ORGANISM: Artificial Sequence
<220> FEATURE:
<223> OTHER INFORMATION: Subtilisin variant

<400> SEQUENCE: 115

Ser Tyr Thr Asp Glu Asn Gly His Gly Thr His Val Ala Gly Ile Ile
1               5                   10                  15

Ala Ala Gln Gly Leu Asn Gly Gly Val Lys Gly Val Ala Pro Asp Ala
            20                  25                  30

Ser Ile Tyr Ala Val Lys Ala Leu Asp Ser Asp Gly Glu Gly
        35                  40                  45
```

PEPTIDE FRAGMENT CONDENSATION AND CYCLISATION USING A SUBTILISIN VARIANT WITH IMPROVED SYNTHESIS OVER HYDROLYSIS RATIO

CROSS REFERENCE TO RELATED APPLICATIONS

This application claims priority and the benefit of PCT/NL2015/050711, filed Oct. 9, 2015, which claims priority and the benefit of PCT/NL2015/050441, filed Jun. 16, 2015, which claims priority and the benefit of PCT/NL2014/050707, filed Oct. 10, 2014, the entire contents of each of which are hereby incorporated in total by reference.

SEQUENCE LISTING

This application incorporates by reference the Sequence Listing contained in an ASCII text file named "362346_00041_Sequence.txt" submitted via EFS-Web. The text file was created on Apr. 7, 2017 and is 70 kb in size.

The invention relates to a method for enzymatically synthesising an (oligo)peptide (i.e. a peptide, in particular oligopeptide), to an enzyme suitable for catalyzing said synthesis, to a host cell capable of functionally expressing said enzyme and to a method for preparing said enzyme.

Peptides, in particular oligopeptides have many applications, for instance as pharmaceutical, food or feed ingredient, or cosmetic ingredient.

Methods for synthesizing (oligo)peptides are generally known in the art.

Oligopeptides can be chemically synthesized in a stepwise fashion in solution or on the solid phase via highly optimized processes. However, peptides longer than 10-15 amino acids are often very difficult to synthesize due to side reactions and as a consequence purification is troublesome. Therefore, peptides longer than 10 amino acids are often synthesized by a combination of solid-phase synthesis of side-chain protected oligopeptide fragments which are subsequently chemically condensed in solution, e.g. as in a 10+10 condensation to make a oligopeptide of 20 amino acids. The major drawback of chemical side-chain protected oligopeptide fragment condensation is that upon activation of the C-terminal amino acid residue of the acyl donor racemisation occurs. In contrast, enzyme-catalyzed peptide couplings are completely devoid of racemisation and have several other advantages over chemical peptide synthesis such as the absence of side reactions on the side-chain functionalities. For industrial application, an enzymatic peptide synthesis concept based on a kinetic approach, i.e. using an acyl donor C-terminal ester is most attractive (see for instance N. Sewald and H.-D. Jakubke, in: "Peptides: Chemistry and Biology", $1^{st}$ reprint, Ed. Wiley-VCH Verlag GmbH, Weinheim 2002).

Chemo-enzymatic peptide synthesis can entail the enzymatic coupling of oligopeptide fragments which have individually been synthesized using chemical synthesis, fermentation, or by a combination of chemical and enzymatic coupling steps. Some reports have been published on the enzymatic condensation of oligopeptide fragments in aqueous solution (Kumaran et al. Protein Science, 2000, 9, 734; Bjorup et al. Bioorg. Med. Chem. 1998, 6, 891; Homandberg et al. Biochemistry, 1981, 21, 3387; Komoriya et al. Int. J. Pep. Prot. Res. 1980, 16, 433). However, a major drawback of such enzymatic oligopeptide fragment condensation in aqueous solution is that simultaneous hydrolysis of the peptide bonds within the oligopeptide fragments and of the C-terminal ester functionality takes place leading to low yields and many side products.

Proteases have hitherto mainly been produced commercially for hydrolytic application, e.g. in cleaning, where peptide bonds are hydrolysed by the proteases. A typical example are the subtilisins, which form an enzyme class with considerable importance for their use as detergents. Therefore, subtilisins have been the subject of numerous protein engineering studies. subtilisins have also been used for the synthesis of oligopeptides, which was, however, almost always accompanied by hydrolytic side-reactions to a significant extent. It was found by Wells et al. (U.S. Pat. No. 5,403,737) that the condensation of oligopeptides in aqueous solution could be significantly improved by altering the active site of subtilisin BPN', a subtilisin from *B. amyloliquefaciens* (SEQUENCE ID NO: 2). When two mutations were introduced, i.e. S221C and P225A, a subtilisin BPN' variant called subtiligase was obtained having a 500-fold increased synthesis over hydrolysis ratio (S/H ratio) as compared to wild-type subtilisin BPN'. However, the average ligating yield was around 66% and hydrolysis of the oligopeptide acyl donor C-terminal ester was still substantial (Wells et al. Science, 1994, 266, 243). Most often, 10 equivalents of oligopeptide acyl donor C-terminal ester was used to obtain a decent reaction yield. Another drawback of subtiligase was the poor stability against organic co-solvents that are required to solubilize the oligopeptide fragments, against enhanced temperature and against denaturating agents, which are often needed for successful oligopeptide condensation. Therefore, Wells et al. added five additional mutations to subtiligase, i.e. M50F, N76D, N109S, K213R and N218S, to make the enzyme more stable (Proc. Natl. Acad. Sci. USA, 1994, 91, 12544). The new mutant called stabiligase appeared moderately more resistant to sodium dodecasulfate and guanidinium hydrochloride, but hydrolysis was still a major side reaction. For instance an oligopeptide carboxyamidomethyl-ester (Cam-ester) was ligated to an oligopeptide amine using stabiligase in a yield of 44%. In this example, 10 equivalents of the oligopeptide C-terminal ester were used and thus, 9.56 equivalents of the oligopeptide C-terminal ester were hydrolyzed at the C-terminal ester functionality and only 0.44 equivalents ligated to the oligopeptide amine to form the product. Clearly, there is a need for an improved enzyme with a higher S/H ratio to make the oligopeptide condensation reaction an economically viable process. Probably for this reason, the past 20 years subtiligase nor stabiligase have been industrially applied, to the best of the inventors knowledge.

Another aspect of subtilisin BPN' that has received attention is the increase of the stability of the enzyme for its use as detergent (i.e. for the hydrolysis of peptide bonds) at higher temperatures and/or in the presence of metal chelators. A typical example of such study was disclosed by Bryan et al. who engineered a subtilisin BPN' variant lacking a high affinity $Ca^{2+}$ binding site (WO02/22796). The high affinity $Ca^{2+}$ binding site in subtilisin BPN' is made up by a loop comprising amino acids 74-82 and the amino acids Gln2 (Q2) and Asp41 (D41). Comparison of the 3D structure of subtilisin BPN' with the structure of homologous subtilisins shows that the high affinity $Ca^{2+}$ binding site is highly conserved. This binding site is important for their stability in known subtilisins. Stripping of the $Ca^{2+}$ ion by for instance metal chelators leads to unfolding and thus inactivation of the known subtilisins. When Bryan et al. deleted amino acids 75-83 (Δ 75-83) of subtilisin BPN' and additionally implemented the mutations Q2K, S3C, P5S, S9A, I31L, K43N, M50F, A73L, E156S, G166S, G169A, S188P, Q206C, N212G, Y217L, N218S, T254A and Q271E, a subtilisin BPN' variant was obtained (called BS149, also known as Sbt149) which lacks the $Ca^{2+}$ binding domain and has a greatly improved stability against metal chelators (1000×). However, this enzyme cannot be used for peptide fragment condensation in aqueous solution since it is only hydrolytically active.

It is an object of the present invention to provide an enzymatic method for preparing an (oligo)peptide by condensation of a first and a second (oligo)peptide fragment or by cyclisation of an (oligo)peptide that can serve as an alternative to known methods of preparing (oligo)peptides. There is a need for alternative methods in general, in particular in order to broaden the palette of tools for making specific (oligo)peptides.

In particular, it is an object to provide an enzymatic method for preparing an (oligo)peptide by condensation of a first and a second (oligo)peptide fragment or by cyclisation of an (oligo)peptide, wherein an enzyme is used having an improved S/H ratio and stability compared to subtilisin BPN', at least under certain reaction conditions.

Further, it is an object to provide an enzymatic method for preparing an (oligo)peptide by condensation of a first and a second (oligo)peptide fragment or by cyclisation of an (oligo)peptide, wherein an enzyme is used having an improved stability compared to subtiligase, in particular an improved stability and S/H ratio compared to subtiligase.

It is yet a further object of the invention to provide the coupling of a (oligo)peptide to a protein. It is in particular a challenge to provide enzymatic methodology that allows coupling of a peptide with a protein, in particular due to the added complexity of a protein's three-dimensional structure.

It is yet a further object to provide a novel subtilisin BPN' variant capable of catalyzing the condensation of two (oligo) peptides or of cyclisation of an (oligo)peptide, in particular such an enzyme having an improved property, such as an improved synthesis over hydrolysis ratio ratio and/or improved stability, compared to known enzymes suitable to catalyse such condensation, such as subtilisin BPN' and/or subtiligase, at least under certain reaction conditions.

One or more other objects that may be subject of the invention follow from the description below.

It has now surprisingly been found that it is possible to provide a subtilisin BPN' variant wherein the calcium binding domain at the positions corresponding to amino acids 75-83 has been inactivated, namely by deletion, that has catalytic activity with respect to the condensation of two (oligo)peptide fragments or the cyclisation of a peptide, and in particular to provide such a variant that has an improved S/H ratio compared to subtilisin BPN' and/or subtiligase, by providing a subtilisin BPN' variant that has a specific mutation, preferably a specific combination of mutations, in addition to the deletion of the amino acids corresponding to positions 75 to 83.

Accordingly, the present invention relates to a method for enzymatically synthesizing an (oligo)peptide, comprising coupling (a) an (oligo)peptide C-terminal ester or thioester and (b) an (oligo)peptide nucleophile having an N-terminally unprotected amine,
    wherein the coupling is carried out in a fluid comprising water, and
    wherein the coupling is catalyzed by a subtilisin BPN' variant or a homologue thereof, which comprises the following mutations compared to subtilisin BPN' represented by SEQUENCE ID NO: 2 or a homologue sequence thereof:
i) a deletion of the amino acids corresponding to positions 75-83;
ii) a mutation at the amino acid position corresponding to S221, the mutation being S221C or S221selenocysteine (S221U);
iii) preferably, a mutation at the amino acid position corresponding to P225;
    wherein the amino acid positions are defined according to the sequence of subtilisin BPN' represented by SEQUENCE ID NO: 2.

Further, the invention relates to a method for enzymatically synthesizing a cyclic (oligo)peptide of at least 12 amino acids, comprising subjecting an (oligo)peptide C-terminal ester or thioester having an N-terminally unprotected amine to a cyclisation step
    wherein said cyclization is carried out in a fluid comprising water, and
    wherein the cyclization is catalyzed by a subtilisin BPN' variant or a homologue thereof, which comprises the following mutations compared to subtilisin BPN' represented by SEQUENCE ID NO: 2 or a homologue sequence thereof:
i) a deletion of the amino acids corresponding to positions 75-83;
ii) a mutation at the amino acid position corresponding to S221, the mutation being S221C or S221selenocysteine;
iii) preferably, a mutation at the amino acid position corresponding to P225;
    wherein the amino acid positions are defined according to the sequence of subtilisin BPN' represented by SEQUENCE ID NO: 2.

Further, the invention relates to an enzyme, which enzyme is a subtilisin BPN' variant or homologue thereof, comprising the following mutations compared to subtilisin BPN' represented by SEQUENCE ID NO: 2 or homologue sequence thereof:
    i) a deletion of the amino acids corresponding to positions 75-83;
    a mutation at the amino acid position corresponding to S221, the mutation being S221C or S221selenocysteine;
    ii) a mutation at the amino acid position corresponding to P225;
    in which the amino acid positions are defined according to the sequence of subtilisin BPN' represented by SEQUENCE ID NO: 2.

Further, the invention relates to a recombinant method for preparing the enzyme according to the invention, said method comprising:
    a) providing a recombinant host cell functionally expressing a gene encoding the enzyme;
    b) culturing said host cell under conditions which provide for the expression of the enzymatically active enzyme; and
    c) recovering the expressed enzyme from said microbial host.

Further, the invention relates to a recombinant polynucleotide comprising a sequence which encodes for an enzyme according to the invention.

Further, the invention relates to a host cell, comprising a polynucleotide according to the invention. The host cell is capable of functionally expressing the enzyme of the invention.

Further, the invention relates to the use of an enzyme according to the invention as a catalyst. Such use generally comprises contacting one or more substrates (reactants) in the presence of the enzyme under conditions wherein the enzyme catalyses a chemical reaction wherein the substrate(s) participate(s). The enzyme has been found particularly useful as a catalyst in peptide synthesis. It is in particular contemplated that an enzyme of the invention is useful for catalyzing reactions of which known subtilisins are known to be catalytically active. In an embodiment, the synthesised peptide is a protein. In an embodiment the synthesised peptide is an oligopeptide. In a further embodiment the synthesised peptide is composed of at least 201 amino acid units.

The invention provides a useful alternative to known methods of preparing (oligo)peptides, including proteins extended with an (oligo)peptide.

Moreover, it has surprisingly been found possible with a method of the invention to enzymatically condense two (oligo)peptide fragments or to cyclize an (oligo)peptide in a liquid comprising water with a high synthesis over hydrolysis ratio. The method of the invention is advantageous in that it offers the possibility for coupling various oligopeptide fragments in aqueous solution in high yield without substantial hydrolytic side reactions. Such surprising finding is illustrated by the Examples, which show that a method of the invention is not only suitable to synthesise (oligo)peptides that lack a secondary and tertiary protein structure, but also allows coupling two peptide fragments wherein at least one of the fragments is a protein, thereby synthesizing an (elongated) protein provided with an additional sequence of amino acid units. It has been found possible to synthesise such protein whilst maintaining a secondary and tertiary structure of the protein.

For the purpose of this invention, with "synthesis over hydrolysis ratio" (S/H ratio) is meant the amount of enzymatically synthesised (oligo)peptide product divided by the amount of (oligo)peptide C-terminal ester or thioester of which the ester or thioester group has been hydrolysed.

The value of the S/H ratio of an enzyme of the invention depends on various factors, for instance the nature of the substrates (the amino acid sequences of the (oligo)peptide C-terminal ester or thioester and of the (oligo)peptide nucleophile) and reaction conditions (e.g. temperature, pH, concentration of the peptide fragments, enzyme concentration). As shown in the Examples, it was found though that under various reaction conditions and for various substrates the S/H ratio was higher than for known subtilisins, such as subtiligase and subtilisin BPN'. Thus, it is contemplated that the S/H ratio of an enzyme according to the invention in general has a significantly higher S/H ratio than subtiligase and subtilisin BPN', when tested under the same reaction conditions and using the same substrates, and in particular it is contemplated that an enzyme of the invention has a significantly higher S/H ratio under the conditions used in Example 1 (100 mM phosphate buffer, pH 8.0, temperature about 20° C., concentration of (oligo)peptide C-terminal ester 0.83 mM, concentration of (oligo)peptide nucleophile 3.33 mM, enzyme concentration 5.5 mg/L) or one or more of the other examples. Thus, in particular, the invention relates to a subtilisin BPN' variant or homologue thereof wherein the S/H ratio of the subtilisin BPN' variant or homologue thereof divided by the S/H ratio of subtiligase—at least under the conditions described in Example 1 or one or more of the other Examples—is more than 1, preferably 2 or more, in particular 5 or more. The upper value of this quotient is not critical; in practice it may e.g. be 100 or less, in particular 20 or less.

The S/H ratio of the subtilisin BPN' variant or homologue thereof of the invention divided by the S/H ratio of subtilisin BPN'—at least under the conditions described in Example 1 or one or more of the other Examples—is usually more than 100, preferably 250 or more, more preferably 500 or more, in particular 1000 or more. The upper value of this quotient is not critical; The S/H ratio of subtilisin BPN' at least under the reaction conditions specified herein is generally very low, it may be even zero (no detectable synthesis). Thus, the S/H ratio of the subtilisin BPN' variant or homologue thereof of the invention divided by the S/H ratio of subtilisin BPN' may approximate infinity. In a potential circumstance wherein subtilisin BPN' has substantial ligase or cyclase activity, the inventors consider that the S/H ratio of the subtilisin BPN' variant or homologue thereof of the invention divided by the S/H ratio of subtilisin BPN' is also high, e.g. up to 100 000, in particular up to 25 000, more in particular up to 10 000.

Further, using a method of the invention, the (oligo) peptide product is very easy to purify from the reaction mixture because only little hydrolytic by-products are formed.

Another advantage of the invention is that, due to the improved S/H ratio, a small or no excess of the (oligo) peptide C-terminal ester or thioester or of the (oligo)peptide nucleophile is needed to reach a high yield (>80%) in the condensation reaction. Accordingly, in an advantageous embodiment an (oligo)peptide C-terminal ester or thioester and an (oligo)peptide nucleophile are contacted in a small excess of one of said (oligo)peptide fragments or in an about stoichiometric ratio although a larger excess of one over the other may be used, as described below.

As illustrated by the Examples, an enzyme according to the invention is also advantageous in that it allows the synthesis of a cyclic (oligo)peptide with significantly higher yield than with subtiligase (78% versus 61% for subtiligase). Cyclic (oligo)peptides are a particularly interesting class of peptides since they are often more potent due to their more constrained three dimensional structure and higher resistance to proteolysis.

Figure 1A:
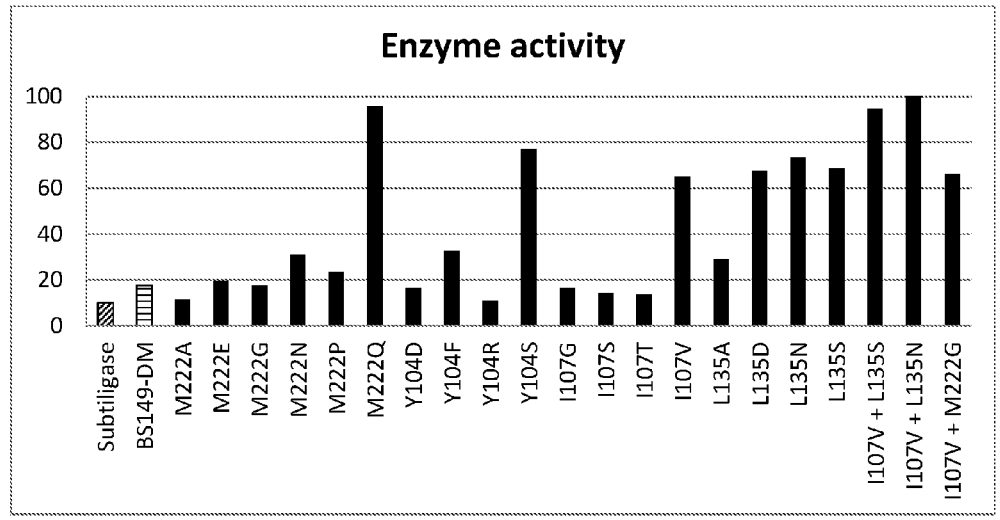
FIGS. 1A and 1B show enzymatic activity respectively S/H ratio of different enzymes of the invention, compared to subtiligase; all indicated mutations on M222, Y104, I107 and/or L135 are additional to those of BS149-DM. The name 'BS149-DM' is used herein for the subtilisin BPN' variant which has the following mutations compared to subtilisin BPN' (SEQUENCE ID NO 2): a deletion of the amino acids 75-83 (Δ75-83) S221C, P225A, Y217L, Q2K, S3C, P5S, S9A, I13L, K43N, M50F, A73L, E156S, G166S, G169A, S188P, Q206C, N212G, N218S, T254A and Q271E.

For the purpose of this invention, with "peptides" is meant any chain composed of two or more amino acids. Thus, peptides are generally amides at least conceptually composed of two or more amino carboxylic acid molecules (i.e. amino acids) by formation of a covalent bond from the carbonyl carbon of one to the nitrogen atom of another with formal loss of water. The term is usually applied to structures formed from alpha-amino acids. A peptide may be linear, branched or cyclic. A peptide can have a single chain composed of two or more amino acids or a peptide can have a plurality of chains. In the case a peptide is composed of two or more chains, each chain generally is composed of three or more amino acid molecules. The amino acid sequence of a peptide is referred to as the primary structure.

In an embodiment, the peptide is essentially free of a secondary structure and essentially free of a tertiairy structure.

In a further embodiment, the peptide has a secondary structure. Secondary structures are generally highly regular local sub-structures, such as alpha-helices and beta-sheets (or beta-strands), by interactions between the individual amino acids and the peptide backbone.

In an embodiment, the peptide (or plurality of peptides) has a tertiary structure. Tertiary structures are generally formed by multiple interactions, among others hydrogen bonding, hydrophobic interactions, van der Waals interactions, ionic interactions and disulphide bonds. The secondary structure can also contribute to the tertiary structure. The tertiary structure provides a three-dimensional shape (which is essentially fixed in a stable environment, such as in the absence of a change in temperature and in the absence of a change in the medium wherein the peptide is present, etc.). As the skilled person knows, the tertiary structure is different from a random coil peptide chain lacking any fixed three-dimensional structure. Proteins are (oligo)peptides having a tertiary structure. A well known example of tertiary structure is the globular structure of globular proteins. In an embodiment, the protein is a protein for target delivery of a pharmaceutically active (oligo)peptide to a specific site, e.g. to a tumour or to organ tissue. Well known examples of proteins, suitable for such purpose, are immunoglobulins or parts thereof, such as an antigen-binding fragment (Fab) of an immunoglobulin. Immuglobulins coupled to a pharmaceutically active (oligo)peptide can thus be used to more efficiently deliver a pharmaceutically active (oligo)peptide to a target, e.g. tumor tissue or organ tissue, that contain an antigen for the immunoglobulin. In an embodiment, the protein is a protein suitable to increase the half-life of an (oligo)peptide in a living organism, in particular the blood plasma half-life. Albumins are examples of proteins that can be coupled to an (oligo)peptide to increase the half-life.

Disulphide bonds (disulphide bridges) are typically bonds between two cysteine units (formed by oxidation). Thus, two amino acids in a same peptide chain (amino acid sequence) can be covalently bound, also if they are not adjacent amino acids in the amino acid sequence. Also, a disulphide bond between a first cysteine of a first peptide chain and a second cysteine of a second peptide chain, which may have the same or a different amino acid sequence, can be formed to form a peptide. Such peptide comprises more than one peptide chain. An example of a peptide composed of more than one peptide chain, wherein the different chains are bound via a disulphide bond is insulin. Other bonds to join different peptide chains are generally known in the art.

In an embodiment, the (oligo)peptide essentially consists of amino acid units. In a further embodiment, the (oligo)peptide essentially consists of amino acid units and protective groups. In an embodiment, the peptide is a conjugate of a peptide chain of two or more amino acids and another molecule, in particular a carobohydrate or a lipid. These peptides are called glycopeptides and lipopeptides respectively. In a further embodiment, the peptide conjugate is a conjugate of two or more amino acids and an imaging agent, such as a fluorescent, phosphorescent, chromogenic or radioactive group. The peptide conjugate may also contain a chelation agent or toxin.

Typically, a peptide—which term includes oligopeptides, proteins and peptide conjugates—comprises up to about 35 000 amino acid units, in particular 3-20 000 amino acid units, more in particular 4-5 000 amino acid units, preferably 5-1000 amino acid units. In a specifically preferred embodiment the peptide comprises 500 amino acid units or less, in particular 200 or less, more in particular 100 or less In a specifically preferred embodiment, the peptide comprises at least 10 amino acid units, more specifically at least 15 amino acids, at least 25 amino acids or at least 40 amino acids.

With "oligopeptides" is meant within the context of the invention, a peptide composed of 2-200 amino acid units, in particular composed of 5-100 amino acid units, more in particular composed of 10-50 amino acid units.

The term "(oligo)peptide" is used herein as a short-hand for the phrase "peptides, in particular oligopeptides".

The (oligo)peptide that is synthesized may be linear, branched or cyclic. Good results have been achieved with the synthesis of a linear or cyclic oligopeptide. Further good results have been achieved in the synthesis of a peptide having more than 200 amino acid units, e.g. of about 800 amino acid units. Thus, the peptide can have at least 250 amino acid units or at least 400 amino acid units. Further, good results have been achieved with the coupling of a peptide fragment to a protein, such as insulin, whilst maintaining a secondary and tertiary protein structure. The protein can have 200 or less amino acid units or can have more than 201 amino acid units.

The non-cyclic (oligo)peptides are synthesized from a first (oligo)peptide and a second (oligo)peptide, which are both smaller than the (oligo)peptide that is synthesized. The first (oligo)peptide is an (oligo)peptide C-terminal ester or thioester and the second (oligo)peptide comprises an N-terminally unprotected amine. The (oligo)peptide C-terminal ester or thioester is also referred to as an (oligo)peptide acyl donor. The second (oligo)peptide is also referred to as an (oligo)peptide nucleophile. These (oligo)peptides from which the synthesised (oligo)peptide is formed are referred to herein as '(oligo)peptide fragments'. These (oligo)peptide fragments can on their turn be synthesized enzymatically from a smaller (oligo)peptide acyl donor and an (oligo)peptide nucleophile or by regular chemical solution or solid phase peptide synthesis, known by the person skilled in the art.

For the purpose of this invention, with "peptide bond" is meant the amide bond between (i) either the alpha-amino terminus of one alpha-amino acid or the beta-amino acid terminus of one beta-amino acid and (ii) either the alpha-carboxyl terminus of one other alpha-amino acid or the beta-carboxyl terminus of one other beta-amino acid. Preferably, the peptide bond is between the alpha-amino terminus of one amino acid and the alpha-carboxyl terminus of another amino acid.

For the purpose of this invention, with "cyclic peptide" is meant an (oligo)peptide chain wherein the alpha-amino terminus and the alpha-carboxyl terminus of a branched or linear (oligo)peptide are linked via a peptide bond, thereby forming a ring structure of at least 12 amino acid units. The cyclic peptide is in particular composed of 12-200 amino acid units, more in particular composed of 12-100 amino acid units and preferably composed of 12-50 amino acid units.

For the purpose of this invention, with "condensation" is meant the formation of a new peptide bond between the C-terminal carboxylic function of an (oligo)peptide with the N-terminal amine function of another (oligo)peptide or of the same (oligo)peptide.

In the context of this application, the term "about" means in particular a deviation of 10% or less from the given value, more in particular 5% or less, even more in particular 3% or less.

As defined by Schechter and Berger, the active site residues in proteases, including subtilisins, are composed of contiguous pockets termed subsites. Each subsite pocket binds to a corresponding residue in the peptide substrate sequence, referred to here as the sequence position. According to this definition, amino acid residues in the substrate sequence are consecutively numbered outward from the cleavage sites as . . . -P4-P3-P2-P1-P1'-P2'-P3'-P4'- . . . (the scissile bond is located between the P1 and P1' positions), while the subsites in the active site are correspondingly labelled as . . . -S4-S3-S2-S1-S1'-S2'-S3'-S4'-. (Schechter and Berger, Biochem Biophys Res Commun. 1967 Apr. 20; 27(2):157-62.)).

For the purpose of this invention, with "S1, S2, S3 and S4 pocket" is meant the amino acids of a protease which interact with the amino acids of an (oligo)peptide acyl donor. The C-terminal amino acid (1st amino acid; P1) of the acyl donor (oligo)peptide interacts with the amino acids in the S1 pocket of the protease. The penultimate amino acid ($2^{nd}$ amino acid; P2) of the acyl donor (oligo)peptide interacts with the amino acids in the S2 pocket of the protease, the third amino acid (P3) with the S3 and the fourth amino acid (P4) with the S4 pocket. The S1-S4 binding pockets of a protease are defined by several amino acids which can be distant in the primary structure of the protease, but are close in the three dimensional space. For the purpose of this invention, with S1' and S2' pockets are meant the amino acids of a protease which interact with the N-terminal amino acids of an (oligo)peptide nucleophile. The N-terminal amino acid of the (oligo)peptide nucleophile interacts with the amino acids in the S1' pocket of the protease. The N-terminal penultimate amino acid of the (oligo)peptide nucleophile interacts with the amino acids in the S2' pocket of the protease. The S1' and S2' binding pockets of a protease are defined by several amino acids which can be distant in the primary structure of the protease, but are close in the three dimensional space.

For the purpose of this invention, with "denaturing agent" is meant an additive which potentially can destroy the three dimensional structure of a protease, and thus, can potentially inactivate the protease.

In the context of the invention with "amino acid side-chain" is meant any proteinogenic or non-proteinogenic amino acid side-chain.

Proteinogenic amino acids are the amino acids that are encoded by the genetic code. Proteinogenic amino acids include: alanine (Ala), valine (Val), leucine (Leu), isoleucine (Ile), serine (Ser), threonine (Thr), methionine (Met), cysteine (Cys), asparagine (Asn), glutamine (Gln), tyrosine (Tyr), tryptophan (Trp), glycine (Gly), aspartic acid (Asp), glutamic acid (Glu), histidine (His), lysine (Lys), arginine (Arg), proline (Pro) and phenylalanine (Phe). Selenocysteine (Sec, U) is an amino acid, of which the structure corresponds to cysteine, with the proviso that it contains a selenium instead of a sulphur atom.

Non-proteinogenic amino acids may in particular be selected amongst D-amino acids, L- or D-phenylglycine, DOPA (3,4-dihydroxy-L-phenylalanine), beta-amino acids, 4-fluoro-phenylalanine, or $C^{\alpha}$-alkylated amino acids.

The term "mutated" or "mutation" as used herein regarding proteins or polypeptides—in particular enzymes—means that at least one amino acid in the wild-type or naturally occurring protein or polypeptide sequence has been replaced with a different amino acid, inserted into, appended to, or deleted from the sequence via mutagenesis of nucleic acids encoding these amino acids. Mutagenesis is a well-known method in the art, and includes, for example, site-directed mutagenesis by means of PCR or via oligo-nucleotide-mediated mutagenesis as described in Sambrook et al., Molecular Cloning-A Laboratory Manual, 2nd ed., Vol. 1-3 (1989). The term "mutated" or "mutation" as used herein regarding genes means that at least one nucleotide in the nucleic acid sequence of that gene or a regulatory sequence thereof, has been replaced with a different nucleotide, has been inserted into, has been appended to, or has been deleted from the sequence via mutagenesis, resulting in the transcription of a protein sequence with a qualitatively of quantitatively altered function or resulting in the knock-out of that gene.

In the present specification, a shorthand for denoting amino acid substitutions employs the single letter amino acid code of the amino acid that is substituted, followed by the number designating where in the protein amino acid sequence the substitution is made. This number is the amino acid position of the wild-type amino acid sequence (generally subtilisin BPN' unless specified otherwise). Thus for the mutated amino acid sequence it is the amino acid position corresponding to the position with that number in the wild type enzyme. Due to one or more other mutations at a lower position (additions, insertions, deletions, etc.) the actual position does not need to be the same. The skilled person will be able to determine the corresponding positions using a generally known alignment technique, such as NEEDLE. The number is followed by the single letter code of the amino acid that replaces the wild-type amino acid therein. For example, G166S denotes the substitution of glycine at the position corresponding to position 166 to serine. X is used to indicate any other proteinogenic amino acid than the amino acid to be substituted. For example, G166X denotes the substitution of glycine 166 to any other proteinogenic amino acid.

When referring to a compound of which stereoisomers exist, the compound may be any of such stereoisomers or a mixture thereof. Thus, when referred to, e.g., an amino acid of which enantiomers exist, the amino acid may be the L-enantiomer, the D-enantiomer or a mixture thereof. In case a natural stereoisomer exists, the compound is preferably a natural stereoisomer.

The term 'pH' is used herein for the apparent pH, i.e. the pH as measured with a standard, calibrated pH electrode.

When an enzyme is mentioned with reference to an enzyme class (EC) between brackets, the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at http://www.chem.qmul.ac.uk/iubmb/enzyme/. Other suitable enzymes that have not (yet) been classified in a specified class but may be classified as such, are meant to be included.

Homologues typically have an intended function in common with the polynucleotide respectively polypeptide (enzyme) of which it is a homologue, such as encoding the same peptide respectively being capable of catalyzing the same reaction. The term homologue is also meant to include nucleic acid sequences (polynucleotide sequences) which differ from another nucleic acid sequence due to the degeneracy of the genetic code and encode the same polypeptide sequence.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively.

The terms "homology", "percent homology", "percent identity" or "percent similarity" are used interchangeably herein. For the purpose of this invention, it is defined here that in order to determine the percent identity of two amino acid sequences or of two nucleic acid sequences, the complete sequences are aligned for optimal comparison purposes. In order to optimize the alignment between the two sequences gaps may be introduced in any of the two sequences that are compared. Such alignment is carried out over the full length of the sequences being compared. Alternatively, the alignment may be carried out over a shorter length, for example over about 20, about 50, about 100 or more nucleic acids or amino acids. The percentage identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby, A. Trends in Genetics 16, (6) pp 276-277, http://emboss.bioinformatics.nl/). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The homology or identity between the two aligned sequences is calculated as follows: the number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity". For purposes of the invention the level of identity (homology) between two sequences (amino acid or nucleotide) is calculated according to the definition of "longest-identity" as can be carried out by using the program NEEDLE.

The polypeptide sequences representing an enzyme of the present invention, can further be used as a "query sequence" to perform a search against sequence databases, for example to identify other family members or related sequences. Such searches can be performed using the BLAST programs. Software for performing BLAST analyses is publicly available through the National Center for Biotechnology Information (http://www.ncbi.nlm.nih.gov). BLASTP is used for amino acid sequences and BLASTN for nucleotide sequences. The BLAST program uses as defaults:
Cost to open gap: default=5 for nucleotides/11 for proteins
Cost to extend gap: default=2 for nucleotides/1 for proteins
Penalty for nucleotide mismatch: default=−3
Reward for nucleotide match: default=1
Expect value: default=10
Wordsize: default=11 for nucleotides/28 for megablast/3 for proteins Furthermore the degree of local identity (homology) between the amino acid sequence query or nucleic acid sequence query and the retrieved homologous sequences is determined by the BLAST program. However only those sequence segments are compared that give a match above a certain threshold. Accordingly the program calculates the identity only for these matching segments. Therefore the identity calculated in this way is referred to as local identity.

The term "homologue" is used herein in particular for polypeptides (enzymes) having a sequence identity of at least 50%, preferably at least 60%, more preferably at least 70%, at least 80%, at least 90%, at least 95%, at least 96%, at least 97%, at least 98% or at least 99% with the polypeptide (enzyme) with which the homologue peptide is compared. Evidently, the sequence identity will be less than 100%. The percentage of sequence identity will depend on the number of mutations and the length of the polypeptide with which the homologue is prepared. In particular, for a subtilisin BPN' variant, the number of mutations for the enzymes in the present invention will typically be at least 11, of which at least nine mutations are deletions and at least two mutations are replacements for another amino acid. In 'longest identity' alignment the deletions are not taken into account. This means that the sequence identity of an enzyme of the invention compared to subtilisin BPN' generally is 99.25% (two replacements in a polypeptide with 266 amino acids) or less. Preferably, the sequence identity of an enzyme of the invention compared to SEQUENCE ID NO 2, is 98% or less, more preferably 96% or less, in particular 94% or less, more in particular 92% or less, or 90% or less.

"Expression" refers to the transcription of a gene into structural RNA (rRNA, tRNA) or messenger RNA (mRNA) with subsequent translation into a protein.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "heterologous expression" refers to the expression of heterologous nucleic acids in a host cell. The expression of heterologous proteins in suitable host cell systems are well known to those of skill in the art. The skilled person will be able to provide suitable host cells for producing an enzyme of the invention from various organisms without undue burden based upon common general knowledge and the information disclosed herein.

As used herein "promoter" is a DNA sequence that directs the transcription of a (structural) gene. Typically, a promoter is located in the 5' region of a gene, proximal to the transcriptional start site of a (structural) gene. Promoter sequences may be constitutive, inducible or repressible. If a promoter is an inducible promoter, then the rate of transcription increases in response to an inducing agent.

The term "vector" as used herein, includes reference to an autosomal expression vector and to an integration vector used for integration into the chromosome.

The term "expression vector" refers to a DNA molecule, linear or circular, that comprises a segment encoding a polypeptide (enzyme) of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

"Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e. operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

As used herein, the term "operably linked" refers to a juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence. Generally, operably linked means that the nucleic acid sequences being linked are contiguous and, where necessary to join two protein coding regions, contiguous and in the same reading frame.

By "host cell" is meant a cell which contains a vector and supports the replication and/or expression of the vector. Host cells may be prokaryotic cells such as bacterial cells, or eukaryotic cells such as yeast, plant, insect, amphibian, or mammalian cells.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

For the purpose of clarity and a concise description features are described herein as part of the same or separate embodiments, however, it will be appreciated that the scope of the invention may include embodiments having combinations of all or some of the features described.

The term 'C-terminal protection' is used herein to indicate that a C-terminal carboxylic group of an (oligo)peptide is provided with a protective group, generally substantially protecting the carboxylic group from being coupled to an N-terminal amine group of another (oligo)peptide or of the same (oligo)peptide molecule. The C-terminal protective group may be a t-alkyl ester group for instance a t-butyl ester group, which is a commonly used protective group. The C-terminal protective group may also be a C-terminal carboxy-amide. A primary carboxy-amide is a commonly used protective group.

The term 'N-terminal protection' is used herein to indicate that an N-terminal amine group of an (oligo)peptide is provided with a protective group, generally at least substantially protecting the N-terminal amine group from being coupled to a C-terminal carboxylic group of another (oligo) peptide or of the same (oligo)peptide molecule.

The (oligo)peptide C-terminal ester or thioester typically is an activated (thio)ester, i.e. it contains a carboxy ester or carboxy thioester group that can take part in the enzymatic coupling reaction. In principle, any (substituted or unsubstituted) alkyl or (substituted or unsubstituted) aryl (thio) ester can be used. Typical examples of (thio)esters which can take part in the enzymatic coupling reaction are methyl-, ethyl, propyl-, isopropyl-, phenyl-, benzyl-, 2,2,2-trichloroethyl-, 2,2,2-trifluoroethyl-, cyanomethyl- and carboxyamidomethyl-(thio)esters.

Particularly good results have been obtained with carboxyamidomethyl-type esters represented by the formula peptide-(C=O)—O—$CX_1X_2$—C(=O)N—$R_1R_2$. Herein, each $X_1$ and $X_2$ independently represents a hydrogen atom or an alkyl group. Good results have been achieved when both $X_1$ and $X_2$ are a hydrogen atom (peptide-(C=O)—O—$CH_2$—C(=O)N—$R_1R_2$). Herein $R_1$ represents a hydrogen atom or an alkyl group and $R_2$ represents a hydrogen atom or an alkyl group or an amino acid or a peptide residue with a C-terminal carboxyamide or carboxylic acid functionality, optionally protected on the side-chain functionality of the amino acid or on one or more of the side-chain functionalities of the amino acids. Herein, each alkyl group may independently represent a (substituted or unsubstituted) C1-C7 alkyl group, preferably a (substituted or unsubstituted) linear C1-C6 alkyl group, more preferably a (substituted or unsubstituted) linear C1-C3 alkyl group, and most preferably a methyl group. Good results have in particular been achieved in a method of the invention wherein both $R_1$ and $R_2$ represent a hydrogen atom or wherein $R_1$ represents a hydrogen atom and $R_2$ represents an amino acid or peptide residue with a C-terminal carboxyamide or carboxylic acid functionality, optionally protected on the side-chain functionality of the amino acid or on one or more of the side-chain functionalities of the amino acids. Particularly good results have been achieved when using the Cam-ester, when $X_1$, $X_2$, $R_1$ and $R_2$ are a hydrogen atom.

The (oligo)peptide C-terminal (thio)ester can be N-terminally unprotected or N-terminally protected. In an embodiment, one or more side-chain functionalities (in particular carboxyl groups, amine groups), e.g. all side-chain functionalities, are provided with a protecting group; in another embodiment all the side-chain functionalities are unprotected. In a preferred embodiment, only the side-chain functionalities of the amino acids at the P4 and P1 position of the (oligo)peptide acyl donor and at the P1' or P2' position of the (oligo)peptide nucleophile (in particular hydroxy groups, carboxyl groups or amine groups) are provided with a protecting group. Suitable protecting groups are known to the person skilled in the art. Carboxylic acid groups can for instance be protected with a cyclohexyl, benzyl or allyl group; amine functionalities can for instance be protected with an allyloxycarbonyl group or a trifluoroacetyl group.

The activated C-terminal (thio)ester group of the (oligo) peptide C-terminal (thio)ester can be synthesized using solid phase synthesis in high yield and purity without racemization. An additional advantage of the use of (thio)esters wherein $R_1$ represents a hydrogen atom and $R_2$ represents an amino acid or peptide residue with a C-terminal carboxylic acid functionality, optionally protected on the side-chain functionality of the amino acid or on one or more of the side-chain functionalities of the amino acids is, that their activated C-terminal ester or thioester group can be synthesized using the cheap and industrially available 2-chlorotritylchloride resin.

The activated C-terminal (thio)ester group of the (oligo) peptide C-terminal (thio)ester can also be synthesized by fermentation using a microorganism. A reliable method to obtain (oligo)peptide (thio)esters using fermentation is via so-called intein expression (see for instance E. K. Lee, Journal of Chemical Technology and Biotechnology, 2010, 9, 11-18). Different intein expression systems kits are commercially available (for instance the IMPACT™ kit). Other methods for the fermentative production of (oligo)peptide (thio)esters are known in the art.

The C-terminal amino acid of the (oligo)peptide C-terminal (thio)ester and the other amino acids of the (oligo) peptide C-terminal (thio)ester may in principle be any amino acid, proteinogenic or non-proteinogenic. If the amino acid sequence of the C-terminal part of the (oligo)peptide C-terminal (thio)ester is poorly recognized by or inaccessible to the coupling enzyme due to the amino acid preference of the coupling enzyme and/or due to the secondary or tertiary structure of the (oligo)peptide, the primary structure (amino acid sequence) may be elongated at the C-terminus. Essentially the C-terminus of the (oligo)peptide C-terminal (thio) ester is elongated with a number of amino acids to ensure good recognition by the enzyme and accessibility into the enzyme for the enzymatic coupling reaction. The skilled person will know how to elongate the (oligo)peptide C-terminal (thio)ester on the basis of the information disclosed herein and common general knowledge. Usually the number of amino acids for elongation is in the range of 1-10, although in principle it can be higher. Good results have been obtained by elongation of the (oligo)peptide C-terminal (thio)ester with 4 amino acid residues, e.g. -Phe-Ser-Lys-Leu-(thio)ester.

In particular the (optionally N-terminal protected) (oligo) peptide C-terminal (thio)ester may be represented by a compound of Formula I.

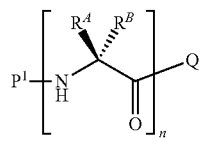

Formula I

Herein Q represents an OR or SR moiety. R may represent a (substituted or unsubstituted) alkyl or a (substituted or unsubstituted) aryl group.

Herein $P^1$ stands for a hydrogen or an N-terminal protecting group. Suitable N-terminal protecting groups are those N-protecting groups which can be used for the synthesis of (oligo)peptides. Such groups are known to the person skilled in the art. Examples of suitable N-protecting groups include carbamate or acyl type protecting groups, for instance 'Cbz' (benzyloxycarbonyl), 'Boc' (tert-butyloxycarbonyl), 'For' (formyl), 'Fmoc' (9-fluorenylmethoxycarbonyl), 'PhAc' (phenacetyl) and 'Ac' (acetyl). The groups For, PhAc and Ac may be introduced and cleaved enzymatically using the enzymes Peptide Deformylase, PenG acylase or Acylase, respectively. Chemical cleavage methods are generally known in the art.

Herein, n is an integer of at least 2. n May in particular be at least 3, at least 4, at least 5, at least 6, at least 7 at least 8, at least 9 or at least 10. n May in particular be 100 or less, 75 or less, 50 or less, 25 or less, 20 or less 15 or less, e.g. 10 or less.

Herein, each $R^A$ and each $R^B$ independently represent a hydrogen atom or an organic moiety, preferably an amino acid side-chain. Thus, it is not required that $R^A$ is the same in all n amino acid units. Similarly, it is not required that $R^B$ is the same in all n amino acid units. Optionally, one or more of the side-chain functionalities may contain a protecting group.

The amino acid units of the (oligo)peptide nucleophile may in principle be selected from any amino acid, proteinogenic or non-proteinogenic.

In particular, the (oligo)peptide nucleophile may be represented by a compound of Formula II.

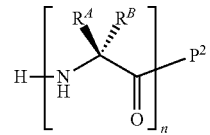

Formula II

Herein, n, $R^A$ and $R^B$ are as defined above.

Herein $P^2$ represents an amine moiety or an OR moiety.

In case $P^2$ represents an amine moiety, the amine moiety may be represented by the formula $NR_3R_4$, in which $R_3$ and $R_4$ may each individually represent any (substituted or unsubstituted) alkyl or (substituted or unsubstituted) aryl group. In particular, one out of $R_3$ and $R_4$ is a hydrogen atom and the other a (substituted or unsubstituted) alkyl group. Good results have particularly been obtained with $R_3$ and $R_4$ both being a hydrogen atom.

In case $P^2$ represents an OR moiety, R may represent a C-terminal protective group or a cation, for instance a monovalent cation, such as a tri- or tetrasubstituted ammonium ion or an alkaline metal cation or an H. In case R is a C-terminal protective group this may in particular be an optionally substituted alkyl group. Preferably it is a t-alkyl group, although in principle it also may be any other protective ester as known to a man skilled in the art. The t-alkyl may in principle be any protective tertiary alkyl group. Preferably the t-alkyl is selected from the group of t-butyl (2-methyl-2-propyl), t-pentyl (2-methyl-2-butyl) and t-hexyl (2,3-dimethyl-2-butyl).

In an embodiment, the (oligo)peptide nucleophile is C-terminal protected. In another embodiment it is not C-terminal protected.

The (oligo)peptide nucleophile may be synthesized using methods known in the art, such as solid-phase synthesis, solution phase synthesis or by fermentation using a microorganism. The N-terminal amino acid of the (oligo)peptide nucleophile and the other amino acids of the (oligo)peptide nucleophile may in principle be any amino acid, proteinogenic or non-proteinogenic. If the amino acid sequence of the N-terminal part of the (oligo)peptide nucleophile is poorly recognized by or inaccessible to the coupling enzyme due to the amino acid preference of the coupling enzyme or due to the secondary or tertiary structure of the (oligo) peptide nucleophile, the primary structure (amino acid sequence) may be elongated at the N-terminus. Essentially the N-terminus of the (oligo)peptide nucleophile is elongated with a number of amino acids to ensure good recognition by and accessibility to the coupling enzyme for the enzymatic coupling reaction. The skilled person will know how to elongate the (oligo)peptide nucleophile on the basis of the information disclosed herein and common general knowledge. Usually the number of amino acids for elongation is in the range of 1-10, although in principle it can be higher. Good result have been obtained by elongation of the (oligo)peptide nucleophile with 3 amino acid residues, e.g. H-Ser-Tyr-Arg.

The invention provides an enzyme having catalytic activity with respect to the formation of a peptide bond (condensation activity), whereby it has catalytic activity in the synthesis of an (oligo)peptide with a high S/H ratio. In particular, the enzyme has ligase activity or cyclase activity, i.e. catalytic activity in the cyclization of an (oligo)peptide by catalyzing the formation of a peptide bond by coupling the C-terminus and the N-terminus of an (oligo)peptide.

In particular, the invention provides an isolated enzyme (isolated from the organism wherein it has been expressed (typically a recombinant organism), if it has been produced in an organism or from the reaction medium in which it has been synthesized.

In particular, an enzyme of the invention is considered isolated for the purpose of the invention if it has been substantially purified by any suitable technique such as, for example, the single-step purification method disclosed in Smith and Johnson, Gene 67:31-40 (1988).

An enzyme of the present invention can be provided in at least substantially pure form (e.g. more than 75 wt. %, more than 80 wt. %) or in a mixture with one or more other components, e.g. in the form of a stock solution, in particular in an aqueous buffer solution.

This enzyme is typically a subtilisin BPN' variant or homologue thereof. The present disclosure provides various examples of enzymes of the invention, which are in particular considered subtilisin BPN' variants. As already described above, an enzyme of the invention should comprise at least:
  a deletion of the amino acids corresponding to L75, N76, N77, S78, I79, G80, V81, L82 and G83 of subtilisin BPN' (Δ75-83; thus in general a deletion of a corresponding $Ca^{2+}$ binding site)
  a cysteine or selenocysteine at a position corresponding to position 221 in subtilisin BPN'
  preferably an amino acid different from proline at position corresponding to position 225 in subtilisin BPN'.

It has surprisingly been found that a mutant having both the deletion corresponding to Δ75-83 of subtilisin BPN' and the mutation to a cysteine corresponding to position 221 in subtilisin BPN' has sufficient stability and an S/H ratio of more than 1, which is an improved S/H ratio compared to, e.g. subtiligase. The position corresponding to S221 in a subtilisin is considered to be important for stability and activity of the enzyme, and of alcalase it has been reported that a single mutation corresponding to S221C results in a virtually inactive enzyme. In this respect, good results have been achieved with the mutation into cysteine at a position corresponding to position 221.

An enzyme of the invention may have further mutations compared to subtilisin BPN', provided that it has enzymatic fragment condensation or cyclisation activity in the preparation of an (oligo)peptide, in particular one or more further mutations as described elsewhere herein.

Alternatives to subtilisin BPN', as template enzymes from which an enzyme according to the invention, in particular a homologue of a subtilisin BPN' variant of the invention, can be derived by mutagenesis are other subtilisins, in particular subtilisins having at least 50% homology with subtilisin BPN'.

Figure 14:
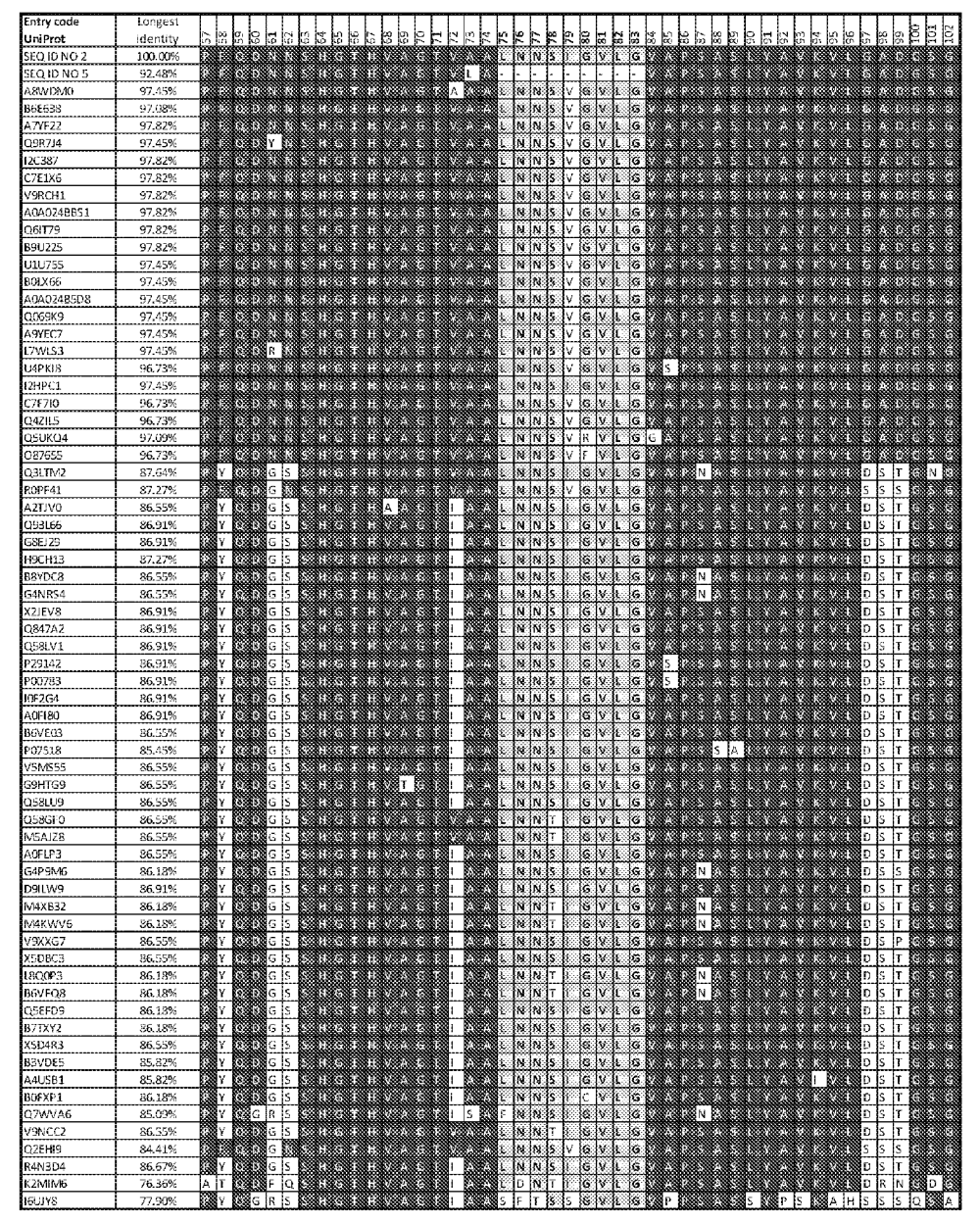
Figure 14:
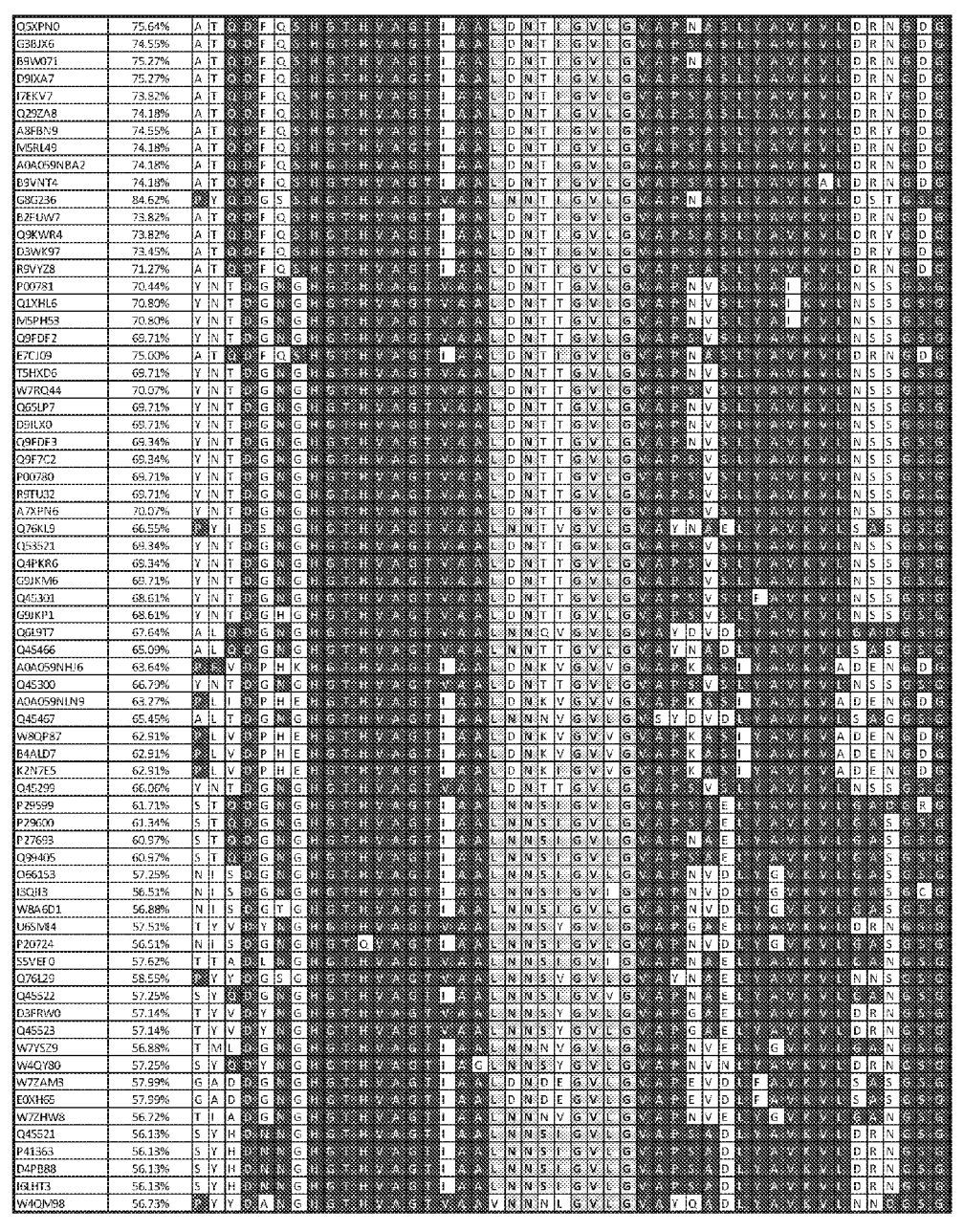
Figure 14:
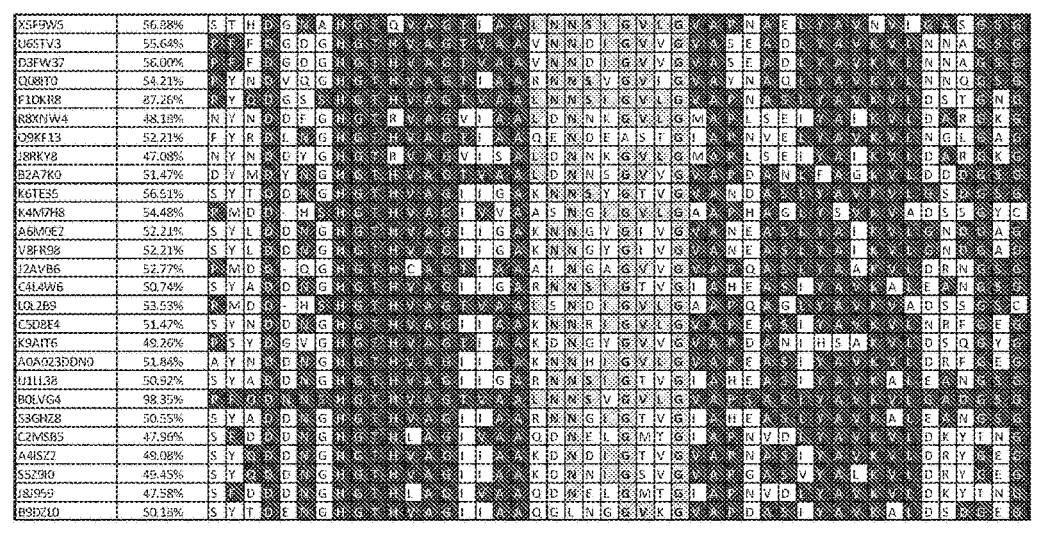

Sequences of suitable subtilisins can be retrieved from the UNIPROT sequence database (http://www.uniprot.org/), as available on 11 Aug. 2014, by BLASTing the database with subtilisin BPN' (SEQ ID 2) as a query. However sequence retrieval is not limited to UNIPROT nor to the date. The skilled person in the art knows how to query alternative sequence depositories or to collect additional homologue sequences by sequencing (see for example *Zooming in on metagenomics: molecular microdiversity of Subtilisin Carlsberg in soil.*, Gabor E, Niehaus F, Aehle W, Eck J. J Mol Biol. 2012 Apr. 20; 418(1-2):16-20). In particular, the invention further relates to variants, having at least said deletions of the amino acids corresponding to L75 till and including G83 of subtilisin BPN', cysteine at a position corresponding to position 221 in subtilisin BPN' and alanine or another mutation at position corresponding to position 225 in subtilisin BPN' (such as a mutation corresponding to P225N, 225D, P225S, P225C, P225G, P225A, P225T, P225V, P225I, P225L, P225H, P225Q of SEQUENCE ID NO: 2) of any of the subtilisins mentioned in FIG. 14, of which the full sequence is as available from said UNIPROT sequence data base and of which the alignments around positions 75-83 are shown.

Preferably, the subtilisin BPN' variant or homologue of the invention comprises a mutation at the position corresponding to P225. For an improvement in S/H ratio, the mutation is usually a mutation corresponding to P225 selected from the group of P225N, P225D, P225S, P225C, P225G, P225A, P225T, P225V, P225I, P225L, P225H, P225Q, P225F and P225E. For an improvement of the S/H ratio compared to, e.g., subtiligase a mutation is preferred corresponding to P225 selected from the group of P225N, P225D, P225S, P225C, P225G, P225A, P225T, P225V, P225I, P225L, P225H and P225Q. Of these, particularly good results have been achieved with said mutation into one of the amino acids of the group commonly referred to as 'Asx', i.e. asparagine (Asn/N) and aspartic acid (Asp/D), i.e. the mutation corresponding to P225N or P225D. Further, particularly good results have been achieved with the mutation corresponding to P225S. Further, particulary good results have been achieved with the mutation corresponding to P225C.

Further, good results have been achieved with the mutation corresponding to P225G. Further, good results have been achieved with the mutation corresponding to P225A. Further, good results have been achieved with the mutation corresponding to P225T. Further, good results have been achieved with the mutation at the position corresponding to P225 into a branched amino acid, i.e. valine (V), isoleucine (I) or Leucine (L).

Preferably, the subtilisin BPN' variant or homologue of the invention comprises one or more mutations at an amino acid position corresponding to Q2, S3, P5, S9, I31, K43, M50, A73, E156, G166, G169, S188, Q206, N212, N218S, T254 and Q271 of SEQUENCE ID NO 2. The inventors found that one or more of the following mutations are advantageous in the subtilisin BPN' variant of the invention: Q2K, S3C, P5S, S9A, I31L, K43N, M50F, A73L, E156S, G166S, G169A, S188P, Q206C, N212G, N218S, T254A and Q271E. In particular for an improved activity, an improved stability or an improved S/H ratio it is preferred that a plurality of said mutations are present in an enzyme of the invention, such as at least two, at least three, more preferably four or more, more preferably five or more, more preferably six or more, more preferably at least eight, more preferably at least 12 of the mutations selected from the group of Q2K, S3C, P5S, S9A, I31L, K43N, M50F, A73L, E156S, G166S, G169A, S188P, Q206C, N212G, N218S, T254A and Q271E. The inventors consider that in particular the presence of one or more of the mutations N218S, S3C-Q206C, G169A, T254A, A73L, M50F and Q2K are advantageous with respect to improving enzyme stability. Further, the inventors consider that in particular the presence of one or more of the mutations I314 E156S, G166S, G169A, is advantageous with respect to improving activity and/or S/H ratio.

Further, a subtilisin BPN' variant or homologue according to the invention comprising a plurality of mutations at an amino acid position corresponding to Q2, S3, P5, S9, I31, K43, M50, A73, E156, G166, G169, S188, Q206, N212, N218S, T254 and Q271 of SEQUENCE ID NO 2 is easier to produce and purify than subtiligase.

In a preferred embodiment, the enzyme, comprises a mutation at the amino acid position corresponding to N218, in particular N218S.

In a preferred embodiment, the enzyme, comprises a mutation at the amino acid position corresponding to M50, in particular M50F.

In a preferred embodiment, the enzyme comprises a mutation at the amino acid position corresponding to Q2, in particular Q2K.

In a preferred embodiment, the enzyme comprises a mutation at the amino acid position corresponding to A73, in particular A73L.

In a preferred embodiment, the enzyme comprises a mutation at the amino acid position corresponding to P5, in particular P5S.

In a preferred embodiment, the enzyme comprises a mutation at the amino acid position corresponding to G166, in particular G166S.

In a preferred embodiment, the enzyme comprises a mutation at the amino acid positions corresponding to S3 and Q206, in particular 53C-Q206C For an improved S/H ratio, it is particularly preferred that the enzyme comprises a mutation at each of the positions corresponding to Q2, P5, M50, A73 and N218, more in particular at each of the positions corresponding to Q2, P5, M50, A73, G166 and N218.

In particular, good results have been achieved with a subtilisin BPN' variant comprising each of the mutations corresponding to Q2K, S3C, P5S, S9A, I31L, K43N, M50F, A73L, E156S, G166S, G169A, S188P, Q206C, N212G, N218S, T254A and Q271E.

Further, it has surprisingly been found that the S/H ratio is improved in general or for certain substrates, by altering the S1' pocket or the S4 pocket by site-specific mutations in one or more of the amino acid positions of said pockets. It is in particular surprising that a site-specific mutation in a pocket, in particular the P1' pocket has an effect in another pocket, in particular the P2' pocket. The inventors realized that this is also advantageous for broadening the range of substrates that can advantageously be used in a method for synthesizing a peptide according to the invention. Thus this broadens the substrate scope for which an enzyme of the invention offers a high S/H ratio.

The S1' pocket is mainly formed by the amino acids M222 and Y217 (Strausberg L. et al. Biochemistry, 2005, 44, 3272; Estell D. A. et al. J. Biol. Chem., 1985, 260, 6518). The three dimensional structure of the S1' binding pocket may also be altered by more distant amino acids, for instance N62, G100, S125, L126, G127, P129, N155 and N218. Substitution of one or more of these amino acids may significantly alter and improve the S/H ratio of the subtilisin BPN' variant or homologue, at least for a number of peptide sequences. In an advantageous embodiment, the substitution at an amino acid position corresponding to M222 or Y217 increases the activity, S/H ratio or substrate scope for which the enzyme shows a (highly) improved S/H ratio.

Preferably, a mutation is present at the position corresponding to M222 is M222G, M222P, M222N, M222E, M222Q or M222A. In a particularly preferred embodiment, said mutation corresponds to M222P or M222G.

Preferably, a mutation at the position corresponding to Y217 is Y217L, Y217N, Y217E, Y217G, Y217S, Y217F or Y217H.

Particularly good results have been obtained with a variant having a mutation selected from the group of M222G, M222P and Y217L in that the S/H ratio and/or the activity of the resulting subtilisin BPN' variant significantly increases, at least for a number of peptide sequences.

The S4 binding pocket is mainly formed by the amino acids Y104, I107, L126, S101, G102, G127, and G128, but the three-dimensional structure of the S4 binding pocket is also determined by more distant amino acids such as L135 and P168 (Ruan et al. Biochemistry, 2008, 47, 6628; Rheinnecker et al. Biochemistry, 1994, 33, 221).

Preferably, the enzyme comprises a mutation at one, two or each of the positions corresponding to Y104, I107 and L135. Particularly good results have been obtained with a subtilisin BPN' variant having a mutation selected from the group of Y104F, Y104S, I107V, I107A, L135N, L135S, L135D and L135A. Substitution of these amino acids can significantly alter and improve the S/H ratio and/or the activity of the enzyme, at least for certain substrates.

In particular, good results with respect to P4 substrate scope, enzyme activity and S/H ratio have been obtained with a subtilisin BPN' variant having a substitution in the amino acid corresponding to I107 (I107V) and a substitution in L135 (L135S or L135N).

In a preferred embodiment, the enzyme of the invention has one or more substitutions in the S1' binding pocket and one or more substitutions in the S4 binding pocket, in particular two or more substitutions in the S1' binding pocket and two or more substitutions in the S4 binding pocket.

A substitution of both the amino acids corresponding to M222 and I107 has been found advantageous for providing an enzyme with improved activity and S/H ratio compared to a variant of the invention having only one of said mutations. Either mutation alone was also found beneficial for the enzyme activity and S/H ratio. In particular, good results in such embodiment have been achieved by mutations I107V and M222G. Examples of other combinations of mutations of specific interest are variants with mutations L135N+M222G and variants with mutations I107V+M222P. Further, such a combination of mutations at the positions corresponding to I107 and M222 offers improvement with respect to substrate scope for both the P4 and the P1' pocket.

In a preferred embodiment, the subtilisin BPN' variant or homologue thereof according to the invention, has a substitution in the S1' binding pocket at the position corresponding to M222 and at the position corresponding to Y217. The M222 mutation in this embodiment preferably is either M222G or M222P. The Y217 mutation preferably is one selected from the group of Y217F, Y217H and Y217G. Such enzymes of the invention have been found to have a broad substrate scope and a good S/H ratio. Particularly good results have been achieved with a subtilisin BPN' variant or homologue thereof comprising the mutations M222P and Y217H; the mutations M222P and Y217G; the mutations M222G and Y217F; or the mutations M222G and Y217G. Of these, a subtilisin BPN' variant or homologue thereof comprising the mutations M222G and Y217F gave particularly good results with respect to substrate broadness and S/H ratio.

Good results have been achieved with a subtilisin BPN' variant or homologue thereof according to the invention having a substitution in the S1' binding pocket at the position corresponding to M222 and at the position corresponding to Y217 that is free of mutations in the S4 binding pocket. However, in an alternative embodiment, with which also good results have been achieved, it additionally has one or more mutations in the S4 binding pocket. In a specific embodiment, this subtilisin BPN' variant or homologue thereof has a substitution in two or more positions of the S4 binding pocket corresponding to Y104, I107, L126, L135, S101, G102, G127, and G128. The mutations in the S4 binding pocket may in particular include I107V and/or either L135N or L135S.

Preferred enzymes according to the invention are in particular the subtilisin BPN' variant or homologues comprising any one of the sequences represented by SEQUENCE ID NO 3, 4 or 5 or homologues thereof. SEQUENCE ID NO 3 shows the preferred mutation corresponding to S221C, although in another embodiment this can be selenocysteine. The X at the position corresponding to P225 can be P, or a different amino acid preferably one of the preferred mutations identified elsewhere herein (N/D/S/C/G/A/T/V/I/LH/Q). SEQUENCE ID NO 4 shows preferred mutation sites compared to SEQUENCE ID NO 3. In SEQUENCE ID NO 4, each X independently represents any proteinogenic amino acid. In particular, any X can be the amino acid present in the wild type subtilisin BPN' at the position of that X or a mutation as described elsewhere in the present disclosure. Preferably, one or more X's represent a mutation, as described elsewhere herein.

In the method of the invention the enzymatic coupling reactions and cyclisations are performed in a fluid comprising water. Preferably the reaction is performed in a buffered fluid. The water content usually is 10-100 vol %, based on total liquids, preferably 20 vol. % or more, preferably 40 vol. % or more, in particular 50 vol. % or more in particular 60 vol. % or more.

In principle, any buffer is suitable. Good buffers are known to a person skilled in the art. See for instance David Sheehan in Physical Biochemistry, $2^{nd}$ Ed. Wiley-VCH Verlag GmbH, Weinheim 2009; http://www.sigmaaldrich-.comdife-science/core-bioreagents/biological-buffers/learning-center/buffer-calculator.html.

The pH of the buffer for an (oligo)peptide fragment condensation may be at least 5, in particular at least 6, preferably at least 7. A desired maximum pH is usually less than 11, in particular less than 10, even more preferably less than 9. Usually the optimal pH for the enzymatic reactions is between 7 and 9. For cyclisation reactions the optimal pH can be different. The pH for the cyclisation reaction may be at least 3, in particular at least 4, preferably at least 5. A desired maximum pH is usually less than 11, in particular less than 10, preferably less than 9. Usually the optimal pH for the enzymatic cyclisation reactions is between 5 and 9.

Due to the high S/H ratio, a large excess of the (oligo)peptide C-terminal ester or thioester or of the (oligo)peptide nucleophile is generally not needed to reach a high yield in the condensation reaction. Usually the ratio of (a) the (oligo)peptide C-terminal ester or thioester to (b) the (oligo)peptide nucleophile is between 1:5 and 5:1, preferably in the range of 1:3 to 3:1, more preferably in the range of 1.0:2.5 to 2.5:1.0, in particular in the range of 1:2 to 2:1, more in particular in the range of 1:1.5 to 1.5:1. An about stoichiometric ratio has been found particularly effective.

In the method of the invention, it may be advantageous to add additives to the fluid wherein the reaction is carried out to improve the solubility of the (oligo)peptide fragments or to improve the reaction yield. Such additives may be a salt or an organic molecule, for instance guanidinium hydrochloride, urea, sodium dodecasulphate or Tween.

The reaction may be carried out in a fully aqueous liquid or in a mixture of water and a water mixable co-solvent such as N,N-dimethylformamide (DMF), N-methyl-pyrrolidinone (NMP), N,N-dimethylacetamide (DMA), dimethylsulphoxide (DMSO), acetonitrile, an ether, such as tetrahydrofuran (THF), 2-methyl-tetrahydrofuran (Me-THF) or 1,2-dimethoxyethane, or a (halogenated) alcohol, such as methanol, ethanol, isopropanol, tert-butanol, 2,2,2-trifluoroethanol (TFE), 1,1,1,3,3,3-hexafluoroisopropanol, or a mixture of these organic solvents. Depending on the stability of the subtilisin BPN' variant and the solubility of the (oligo)peptide substrates, the amount of co-solvent is preferably below 70 vol %, more preferably below 60 vol %, even more preferably below 50 vol %, and most preferably below 40%.

In principle the temperature during the enzymatic fragment condensations or cyclisations is not critical, as long as a temperature is chosen at which the subtilisin BPN' variant used show sufficient activity and stability. Such a temperature is usually known for the subtilisin BPN' variant to be used or can be routinely determined, making use of a known substrate for the subtilisin BPN' variant under known reaction conditions. Generally, the temperature may be at least −10° C., in particular at least 0° C. or at least 10° C. Generally, the temperature may be 70° C. or less, in particular 60° C. or less or 50° C. or less. Optimal temperature conditions can easily be identified for a specific subtilisin BPN' variant for a specific enzymatic fragment condensation or cyclisation by a person skilled in the art through routine experimentation based on common general knowledge and the information disclosed herein. In general, the temperature advantageously is in the range of 20-50° C.

The subtilisin BPN' variants of the present invention are generally produced by recombinant methods, in particular by expression of a subtilisin BPN' DNA which has been mutated such that upon expression it results in a subtilisin BPN' variant of the invention which is enzymatically active.

Expression of the DNA of the subtilisin BPN' variants and homologues thereof of the present invention is provided using available vectors and regulatory sequences. The actual selection depends in large part upon the particular host cells which are utilized for expression. For example, if the subtilisin BPN' mutant DNA is expressed in *Bacillus*, a *Bacillus* promoter is generally utilized as well as a *Bacillus* derived vector.

In order to produce and secrete the enzyme of the invention from a host cell into the medium, a gene may be used which encodes a precursor polypeptide (enzyme) containing a signal sequence and a pre-pro sequence preceding the mature enzyme. In subtilisin BPN', the additional N-terminal sequence comprises 107 amino acids. Upon secretion first the signal sequence can be removed and after secretion the pre-pro sequence can be removed resulting in the fully active enzyme (James A. Wells, Nucleic Acids Research, Volume 11 Number 22 1983). In case of native subtilisin BPN' the mature enzyme comprises 275 amino acids. Conveniently to describe the position of individual amino acids in the polypeptide chain of subtilisin BPN' and its homologues the so called subtilisin BPN' numbering is used which runs from the N-terminus (amino acid 1) tot the C-terminus (amino acid 275). Corresponding positions in homologous enzymes can be determined by aligning said homologous sequences with the sequence of subtilisin BPN'.

As is known to the person skilled in the art, it is possible that the N- and/or C-termini of the mature polypeptide numbered 1-275 within SEQ ID NO: 5 or of the mature enzyme in the amino acid sequence according to SEQ ID NO: 2, 3 or 4 (as set out in amino acids 1 to 275) maybe heterogeneous, due to variations in processing during maturation. In particular such processing variations might occur upon overexpression of the enzyme. In addition, exo-protease activity might give rise to heterogeneity. The extent to which heterogeneity occurs depends also on the host and fermentation protocols that are used. Such C-terminal processing artefacts might lead to shorter polypeptides or longer polypeptides than indicated with the mature wild-type subtilisin BPN' (SEQ ID NO: 2) or with the mature enzymes according to the invention represented by SEQ ID NO: 3 or 4. As a result of such processing variations the N-terminus might also be heterogeneous. Processing variants at the N-terminus could be due to alternative cleavage of the signal sequence by signal peptidases.

The enzyme of the invention may be produced by recombinant technology, based on common general knowledge and the information disclosed herein. For secretion of the translated enzyme into the lumen of the endoplasmic reticulum, into the periplasmic space or into the extracellular environment, an appropriate secretion signal sequence may be fused to the polynucleotide encoding the enzyme of the invention. The signals may be endogenous to the enzyme or they may be heterologous signals.

The enzyme according to the invention may be produced in a modified form, such as a fusion protein, and may include not only secretion signals but also additional heterologous functional regions. Thus, for instance, a region of additional amino acids (a so called tag), particularly charged amino acids, may be added to the enzyme, in particular to the C-terminus of the enzyme, to improve stability and persistence in the host cell, during purification or during subsequent handling and storage or to facilitate the purification. Examples of suitable tags are for instance described in a review by M. E. Kimple et al., in 'Current Protocols in Protein Science 9.9.1-9.9.23, August 2013'. A well known example of a useful tag is the so called His tag, an amino acid sequence having a plurality of histidine units. The inventors found that such a tag could be used successfully in the production and purification of enzymes of the invention. No substantial differences in functional enzyme properties were observed between enzymes with the His tag and enzymes without the His tag.

Further, an enzyme of the invention can be produced as an inclusion body with refolding in an appropriate buffer.

Enzymes of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the enzymes of the present invention may be glycosylated or may be non-glycosylated. In addition, enzymes of the invention may also include an initial modified methionine residue, in some cases as a result of host-mediated processes.

Polynucleotides of the invention can be incorporated into a vector, including cloning and expression vectors. A vector may be a recombinant replicable vector. The vector may be used to replicate a polynucleotide of the invention in a compatible host cell. The vector may conveniently be subjected to recombinant DNA procedures.

The invention also pertains to methods of growing, transforming or transfecting such vectors in a suitable host cell, for example under conditions in which expression of an enzyme of the invention occurs. The invention provides a method of making enzymes of the invention by introducing a polynucleotide of the invention into a vector, in an embodiment an expression vector, introducing the vector into a compatible host cell, and growing the host cell under conditions which bring about replication of the vector.

The vector may be recovered from the host cell.

A vector according to the invention may be an autonomously replicating vector, i.e. a vector which exists as an extra-chromosomal entity, the replication of which is independent of chromosomal replication, e.g. a plasmid.

Alternatively, the vector may be one which, when introduced into a host cell, is integrated into the host cell genome and replicated together with the chromosome(s) into which it has been integrated.

One type of vector is a "plasmid", which refers to a circular double stranded DNA loop into which additional DNA segments can be inserted. Another type of vector is a viral vector, wherein additional DNA segments can be inserted into the viral genome.

Certain vectors are capable of autonomous replication in a host cell into which they are introduced (e.g., bacterial vectors having a bacterial origin of replication and episomal mammalian vectors). Other vectors (e.g., bacterial integration vector without a suitable origin of replication or a non-episomal mammalian vectors) are integrated into the genome of a host cell upon introduction into the host cell, and thereby are replicated along with the host genome.

The recombinant expression vectors of the invention comprise a polynucleotide of the invention in a form suitable for expression of the polynucleotide in a host cell, which means that the recombinant expression vector includes one or more regulatory sequences, selected on the basis of the host cells to be used for expression, which is operably linked to the polynucleotide sequence to be expressed. The term regulatory sequence includes promoters, enhancers and other expression control elements (e.g., polyadenylation signal). Such regulatory sequences are described, for example, in Goeddel; Gene Expression Technology: Methods in Enzymology 185, Academic Press, San Diego, Calif. (1990).

A vector or expression construct for a given host cell may thus comprise the following elements operably linked to each other in a consecutive order from the 5'-end to 3'-end relative to the coding strand of the sequence encoding an enzyme of the invention: (1) a promoter sequence capable of directing transcription of the nucleotide sequence encoding the enzyme in the given host cell; (2) a ribosome binding site to facilitate the translation of the transcribed RNA (3) optionally, a signal sequence capable of directing secretion of the enzyme from the given host cell into a culture medium; (4) a polynucleotide sequence according to the invention; and preferably also (5) a transcription termination region (terminator) capable of terminating transcription downstream of the nucleotide sequence encoding the enzyme.

Downstream of the nucleotide sequence according to the invention there may be a 3' untranslated region containing one or more transcription termination sites (e.g. a terminator, herein also referred to as a stop codon). The origin of the terminator is less critical. The terminator can, for example, be native to the DNA sequence encoding the enzyme. However, preferably a bacterial terminator is used in bacterial host cells and a filamentous fungal terminator is used in filamentous fungal host cells. More preferably, the terminator is endogenous to the host cell (in which the nucleotide sequence encoding the enzyme is to be expressed). In the transcribed region, a ribosome binding site for translation may be present. The coding portion of the mature transcripts expressed by the constructs will include a start codon is usually AUG (or ATG), but there are also alternative start codons, such as for example GUG (or GTG) and UUG (or TTG), which are used in prokaryotes. Also a stop or translation termination codon is appropriately positioned at the end of the polypeptide to be translated.

Enhanced expression of the polynucleotide of the invention may also be achieved by the selection of homologous and heterologous regulatory regions, e.g. promoter, secretion leader and/or terminator regions, which may serve to increase expression and, if desired, secretion levels of the protein of interest from the expression host and/or to provide for the inducible control of the expression of an enzyme of the invention.

The enzymes according to the invention can be produced in bacterial cells such as *E. coli* and *Bacilli*, insect cells (using baculovirus expression vectors), fungal cells, yeast cells or mammalian cells. Suitable host cells are discussed herein and further in Goeddel, Gene Expression Technology: Methods in Enzymology 185, Academic Press, San Diego, Calif. (1990) and in "Production of Recombinant Proteins: Novel Microbial and Eukaryotic Expression Systems", 2004, Wiley-Blackwell, Editor (http://eu.wiley.com/WileyCDA/Section/id-302479.html?query=Gerd+Gellissen).

Alternatively, the recombinant expression vector can be transcribed and translated in vitro, for example using T7 promoter regulatory sequences and T7 polymerase.

For most bacteria, filamentous fungi and yeasts, the vector or expression construct is preferably integrated in the genome of the host cell in order to obtain stable transformants. In case the expression constructs are integrated in the host cells genome, the constructs are either integrated at random loci in the genome, or at predetermined target loci using homologous recombination, in which case the target loci preferably comprise a highly expressed gene.

In the invention, bacteria, in particular *Bacilli*, may preferably be used as host cells for the expression of an enzyme of the invention. Suitable inducible promoters useful in such host cells include promoters regulated primarily by an ancillary factor such as a repressor or an activator. The repressors are sequence-specific DNA binding proteins that repress promoter activity. The transcription can be initiated from this promoter in the presence of an inducer that prevents binding of the repressor to the operator of the promoter. Production of secondary sigma factors can be primarily responsible for the transcription from specific promoters. Attenuation and antitermination also regulates transcription.

Strong constitutive promoters are well known and an appropriate one may be selected according to the specific sequence to be controlled in the host cell. A variety of promoters can be used that are capable of directing transcription in the recombinant host cells of the invention. Preferably the promoter sequence is from a highly expressed gene. Vector DNA can be introduced into prokaryotic or eukaryotic cells via natural competence, conventional transformation or transfection techniques. As used herein, the terms "transformation" and "transfection" are intended to refer to a variety of art-recognized techniques for introducing foreign polynucleotide (e.g., DNA) into a host cell, including calcium phosphate or calcium chloride co-precipitation, DEAE-dextran-mediated transfection, transduction, infection, lipofection, cationic lipid mediated transfection or electroporation. Suitable methods for transforming or transfecting host cells can be found in Sambrook, et al. (supra) and other laboratory manuals.

In order to identify and select cells which harbor a vector, a gene that encodes a selectable marker (e.g., resistance to antibiotics) is generally introduced into the host cells along with the polynucleotide of the invention. Preferred selectable markers include, but are not limited to, those which confer resistance to drugs or which complement a defect in the host cell. They also include e.g. versatile marker genes that can be used for transformation of most filamentous fungi and yeasts such as acetamidase genes or genes providing resistance to antibiotics like G418, hygromycin, bleomycin, kanamycin, methotrexate, phleomycin orbenomyl resistance (benA). Alternatively, specific selection markers can be used such as auxotrophic markers which require corresponding mutant host strains: e.g. D-alanine racemase (from *Bacillus*), URA3 (from *S. cerevisiae* or analogous genes from other yeasts), pyrG or pyrA (from *A. nidulans* or *A. niger*), argB (from *A. nidulans* or *A. niger*) or trpC. In an embodiment the selection marker is deleted from the transformed host cell after introduction of the expression construct so as to obtain transformed host cells capable of producing enzymes of the invention which are free of selection marker genes.

Expression of proteins in prokaryotes is often carried out with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

Vectors preferred for use in bacteria are for example disclosed in WO-A1-2004/074468, which are hereby enclosed by reference. Other suitable vectors will be readily apparent to the skilled artisan.

Vectors of the invention may be transformed into a suitable host cell as described herein to provide for expression of a polypeptide of the invention. Thus, in a further aspect the invention provides a process for preparing an enzyme according to the invention which comprises cultivating a host cell transformed or transfected with an expression vector encoding the enzyme, and recovering the expressed polypeptide.

A polynucleotide according to the invention encodes, when transformed into a proper host cell an enzyme according to the invention. The invention features cells, e.g., transformed host cells or recombinant host cells comprising a polynucleotide according to the invention or comprising a vector according to the invention. A "transformed host cell" or "recombinant host cell" is a cell into which a polynucleotide according to the invention has been introduced, by means of recombinant DNA techniques.

Both prokaryotic and eukaryotic cells are included, e.g., bacteria, fungi, yeast, insect, mammalian and the like.

Suitable host cells include bacteria, including *Escherichia, Anabaena, Caulobactert, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus Streptomyces*, and *Pseudomonas*, In an aspect of the vector according to the invention, the host cell is a bacterial cell selected from the group consisting of *B. subtilis, B. puntis, B. megaterium, B. halodurans, B. pumilus, G. oxydans, Caulobactert crescentus CB* 15, *Methylobacterium extorquens, Rhodobacter sphaeroides, Pseudomonas zeaxanthinifaciens, Paracoccus denitrificans, C. glutamicum, Staphylococcus carnosus, Streptomyces lividans, Sinorhizobium melioti* and *Rhizobium radiobacter*.

In a further embodiment of the vector according to the invention the suitable host cell is an *Aspergillus, Chrysosporium, Kluyveromyces, Penicillium, Saccharomyces*, or *Talaromyces* species.

Preferably the host cell is a *Bacillus subtilis, Bacillus amyloliquefaciens, Bacillus licheniformis, Escherichia coli, Aspergillus Niger* or *Aspergillus oryzae* species.

The recombinant host cell according to the invention may comprise the polynucleotide according to the invention or the vector according to the invention. In an embodiment of the recombinant host cell according the invention, the recombinant host cell is capable of expressing or overexpressing the polynucleotide according to the invention or the vector according to the invention.

The method according to the invention for manufacturing the polynucleotide according to the invention or the vector according to the invention comprises the steps of culturing a host cell transformed with said polynucleotide or said vector and isolating said polynucleotide or said vector from said host cell.

Preferred are cells of a *Bacillus* strain, e.g., *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis*; or a *Streptomyces* strain, e.g., *Streptomyces lividans* or *Streptomyces murinus*; or from a gram negative bacterium, e.g., *E. coli* or *Pseudomonas* sp. (Long Liu et al., Appl Microbiol Biotechnol (2013) 97:6113-6127 and Kay Terpe, Appl Microbiol Biotechnol (2006) 72:211-222).

According to another aspect, the host cell is a eukaryotic host cell. In an embodiment the eukaryotic cell is a fungal cell, i.e. a yeast cell, such as *Candida, Hansenula, Kluyveromyces, Pichia, Saccharomyces, Schizosaccharomyces*, or *Yarrowia* strain. Preferably the yeast cell is a *Kluyveromyces lactis, S. cerevisiae, Hansenula polymorpha, Yarrowia lipolytica, Pichia pastoris*, or a filamentous fungal cell.

Filamentous fungi include all filamentous forms of the subdivision *Eumycota* and *Oomycota* (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Thermoascus, Thielavia, Tolypocladium* and *Trichoderma*. In an embodiment, filamentous fungal cells are used belonging to a species of an *Aspergillus, Chrysosporium, Penicillium, Talaromyces, Fusarium* or *Trichoderma* genus, and preferably a species of *Aspergillus niger, Aspergillus awamori, Aspergillus foetidus, Aspergillus sojae, Aspergillus fumigatus, Talaromyces emersonii, Aspergillus oryzae, Chrysosporium lucknowense, Myceliophthora thermophila, Fusarium oxysporum, Trichoderma reesei* or *Penicillium chrysogenum*.

A host cell can be chosen which modifies and processes the encoded enzyme in a specific, desired fashion after translation. Such post translational modification (e.g., glycosylation) and processing (e.g., cleavage) of protein products may facilitate optimal functioning of the protein. Various host cells have characteristic and specific mechanisms for post-translational processing and modification of proteins and gene products. Appropriate cell lines or host systems familiar to those skilled in the art of molecular biology and/or microbiology can be chosen to ensure the desired and correct modification and processing of the foreign protein produced. E.g., in an embodiment a subtilisin BPN' variant or homologue thereof is initially secreted as a pre-pro-enzyme and the presence of the 77 amino acid pro sequence is important for in vivo production of mature subtilisin but has to be cleaved off to obtain full catalytic activity.

A method of producing an enzyme according to the invention typically comprises cultivating a recombinant host cell e.g. transformed or transfected with an expression vector under conditions to provide for expression of a coding sequence encoding the enzyme and recovering and purifying the produced enzyme from the cell or culture medium. Polynucleotides of the invention can be incorporated into a recombinant replicable vector, e. g. an expression vector or a replication vector. Transcription vectors are used to amplify their insert.

The purpose of a vector which transfers genetic information to another cell is typically to isolate, multiply, or express the insert in the target cell. Vectors called expression_vectors (expression constructs) specifically are for the expression of the transgene in the target cell, and generally have a promoter sequence that drives expression of the transgene. Simpler vectors called transcription vectors are only capable of being transcribed but not translated: they can be replicated in a target cell but not expressed, unlike expression vectors. Transcription vectors are used to amplify their insert. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

Preferably, the enzyme according to the invention is produced as a secreted protein in which case the nucleotide sequence encoding a mature form of the enzyme in the expression construct is operably linked to a nucleotide sequence encoding a signal sequence. Preferably the signal sequence is native (homologous), also referred to herein as "wild type" to the nucleotide sequence encoding the enzyme. Alternatively the signal sequence is foreign (heterologous) to the nucleotide sequence encoding the enzyme, in which case the signal sequence is preferably endogenous to the host cell in which the nucleotide sequence according to the invention is expressed. Examples of suitable signal sequences for bacilli can be found in "van Dijl, J. M. et al. 2001. In: Sonenshein, A. L., Hoch, J. A. and Losick, R., eds. Bacillus subtilis and its closest relatives: from genes to cells. Washington, D.C.: ASM Press, pp. 337-355" and "Degering C et al., Appl Environ Microbiol. 2010 October; 76(19): 6370-6."

Expression of heterologous proteins in yeast is well known. Sherman, F., et al., Methods in Yeast Genetics, Cold Spring Harbor Laboratory (1982) is a well recognized work describing the various methods available to express proteins in yeast. Vectors, strains, and protocols for expression in, e.g. *Saccharomyces* and *Pichia* are generally known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired. More specifically, suitable yeast signal sequences are those from yeast alfa-factor genes. Similarly, a suitable signal sequence for filamentous fungal host cells is e.g. a signal sequence from a filamentous fungal amyloglucosidase (AG) gene, e.g. the *A. niger* g/aA gene. This may be used in combination with the amyloglucosidase (also called (gluco) amylase) promoter itself, as well as in combination with other promoters. Hybrid signal sequences may also be used with the context of the present invention. Preferred heterologous secretion leader sequences are those originating from the fungal amyloglucosidase (AG) gene (g/aA-both 18 and 24 amino acid versions e.g. from *Aspergillus*), the [alpha]-factor gene (yeasts e.g. *Saccharomyces* and *Kluyveromyces*) or the [alpha]-amylase (amyE, amyQ and amyL) and alkaline protease aprE and neutral protease genes (*Bacillus*).

A heterologous host cell may also be chosen wherein the enzyme of the invention is produced in a form which is substantially free of enzymatic activities that might interfere with the applications, e.g. free from peptide degrading or modifying enzymes. In particular in the case of producing variants, the host cell should not produce any wild type enzyme. This may be achieved by choosing a host cell which does not normally produce such enzymes or by deliberately removing the corresponding genes by techniques known in the art.

The invention encompasses processes for the production of the enzyme of the invention by means of recombinant expression of a DNA sequence encoding the enzyme of the invention. For this purpose the DNA sequence of the invention can be used for gene amplification and/or exchange of expression signals, such as promoters, secretion signal sequences, in order to allow economic production of the enzyme in a suitable homologous or heterologous host cell. A homologous host cell is a host cell which is of the same species or which is a variant within the same species as the species from which the DNA sequence is obtained. The host cell may over-express the enzyme, and techniques for engineering over-expression are well known. The host may thus have two or more copies of the encoding polynucleotide (and the vector may thus have two or more copies accordingly). Therefore in one embodiment of the invention the recombinant host cell according to the invention is capable of expressing or overexpressing a polynucleotide or vector according to the invention.

Another aspect of the invention is a method for producing an enzyme of the invention comprising (a) culturing a recombinant host cell according to the invention under conditions such that the enzyme of the invention is produced; and (b) optionally recovering the enzyme of the invention from the cell culture medium. For each combination of a promoter and a host cell, culture conditions are available which are conducive to the expression the DNA sequence encoding the enzyme. After reaching the desired cell density or titer of the enzyme the culture is stopped and the enzyme is recovered. The term "culturing" includes maintaining and/or growing a living recombinant host cell of the present invention, in particular the recombinant host cell according to the invention.

In one aspect, a recombinant host cell of the invention is cultured in liquid media. In another aspect, a recombinant host cell is cultured in solid media or semi-solid media. Preferably, the recombinant host cell of the invention is cultured in liquid media comprising nutrients essential or beneficial to the maintenance and/or growth of the recombinant host cell. The recombinant host cells may be cultured in liquid media either continuously or intermittently, by conventional culturing methods such as standing culture, test tube culture, shaking culture, aeration spinner culture or fermentation. Preferably, the recombinant host cells are cultured in a fermentor. Fermentation processes of the invention include batch, fed-batch and continuous methods of fermentation. A variety of such processes have been developed and are well known in the art.

The recombinant host cells are preferably cultured under controlled pH. In one embodiment, recombinant host cells may be cultured at a pH of between 4.5 and 8.5, preferably 6.0 and 8.5, more preferably at a pH of about 7. The desired pH may be maintained by any method known to those skilled in the art.

Preferably, the recombinant host cells are further cultured under controlled aeration and under controlled temperatures. In one embodiment, the controlled temperatures include temperatures between 15 and 70° C., preferably the temperatures are between 20 and 55° C., more preferably between 30 and 50° C. The appropriate conditions are usually selected based on the choice of the expression host and the protein to be produced.

In a specific embodiment, the enzyme is expressed in *Bacillus* strain GX4935 (see examples). The strain is cultivated under aerobic conditions in a suitable fermentation medium. A suitable medium medium may contain assimilable sources of carbon and nitrogen besides inorganic salts optionally together with growth promoting nutrients, such as yeast extract. Fermentation is typically conducted at 35-40° C. and at a pH of 6.5-7.5 and preferably kept approximately constant by automatic means. The enzyme is excreted into the medium. At the end of fermentation, if required, the production host may be killed by means known by the person skilled in the art. The ensuing fermentation broth may be freed of bacterial cells, debris therefrom together with other solids, for example by filtration or centrifugation. The filtrate or supernatant containing the enzyme may be further clarified, for example by filtration or centrifugation, and then concentrated as required, for example by ultrafiltration or in an evaporator under reduced pressure to give a concentrate which, if desired, may be taken to dryness, for example by lyophilization or spray-drying.

After fermentation, if necessary, the cells can be removed from the fermentation broth by means of centrifugation or filtration. After fermentation has stopped or after removal of the cells, the enzyme of the invention may then be recovered and, if desired, purified and isolated by conventional means, including, but not limited to, treatment with a conventional resin, treatment with a conventional adsorbent, alteration of pH, solvent extraction, dialysis, filtration, concentration, crystallization, recrystallization, pH adjustment, lyophilisation and the like. For example, the enzymes according to the invention can be recovered and purified from recombinant cell cultures by methods known in the art (Protein Purification Protocols, Methods in Molecular Biology series by Paul Cutler, Humana Press, 2004). Usually, the compound is "isolated" when the resulting preparation is substantially free of other components.

In an embodiment, an isolated enzyme preparation is provided having a purity of about 80% (by dry weight) of the enzyme of the invention or more (i.e. less than about 20% of all the media, components or fermentation byproducts). In a specific embodiment, the invention provides the enzyme of the invention in a purity of about 90% or more, preferably in a purity of 95% or more, in particular in a purity of 98% or more. In practice, a minor amount of other components may be present in an isolated enzyme preparation of the invention. Thus, a purified preparation of the enzyme may comprise 99% or less of the enzyme, in particular 98% or less.

Alternatively, however, the enzyme of the invention is not purified from the recombinant host cell or the culture. The entire culture or the culture supernatant may be used as a source of the enzyme. In a specific embodiment, the culture or the culture supernatant comprising the enzyme is used without substantial modification.

It is further noted that it is also possible to make the enzyme of the invention, such as the subtilisin BPN' variant, by known chemical protein synthesis technology, e.g. by solid phase peptide synthesis. However, expression of the subtilisin mutants in microbial host cells will generally be preferred since this will allow for the microbial host cell to produce the subtilisin protein in a proper conformation for enzymatic activity. However, it should be possible to convert improperly folded subtilisin BPN' variants or homologues thereof into an active conformation.

The enzymes of the invention (subtilisin BPN' variants or homologues thereof) may be chemically or biochemically modified, e.g. post-translationally modified. For example, they may be glycosylated or comprise modified amino acid residues. They may also be modified by the addition of a tag, as already mentioned above. Such modified polypeptides and proteins fall within the scope of the term "enzyme" of the invention.

In order to further illustrate the present invention and the advantages thereof, the following specific examples are given, it being understood that the same is intended only as illustrative and in nowise limitative.

EXAMPLES

Production of Enzymes (for use) According to the Invention
Mutagenesis, Cloning and Expression The gene coding for subtilisin BS149 (Ruan et al. 2008) was obtained from Philip N. Bryan (University of Maryland Biotechnology Institute, 9600 Gudelsky Drive, Rockville, Md. 20850). Mutagenesis was performed using a pUB110 based *Escherichia. coli-Bacillus subtilis* (*E. coli-B. subtilis*) shuttle vector harboring the BS149 gene using either the native promotor or alternatively using the aprE promotor and optionally a C-terminal his-tag (pBE-S DNA, http://www.clontech.com/takara). The gene encoding an enzyme according to the invention was constructed by introducing the mutations S221C and P225A into the BS149 gene using the site-directed mutagenesis method (Sambrook et al., 1989). All primers were designed using the Agilent Primer design tool (http://www.genomics.agilent.com). The constructed sequences were verified by DNA sequencing before transformation to *Bacillus subtilis* GX4935.

In order to produce BS149-DM without a His-tag the gene coding for BS149-DM and its natural promoter sequence was cloned into the pBS42 shuttle vector (DSMZ, Germany) at EcoRI/BamHI sites. The ligation mixtures were transformed into competent *Escherichia coli* and transformants were plated on LB plates containing chloramphenicol (34 µg/mL). The plasmid pBS42-S5 was propagated in *E. coli*, isolated and validated by sequencing. The sequence validated plasmid was used to transform *B. subtilis* host.

Figure 12:
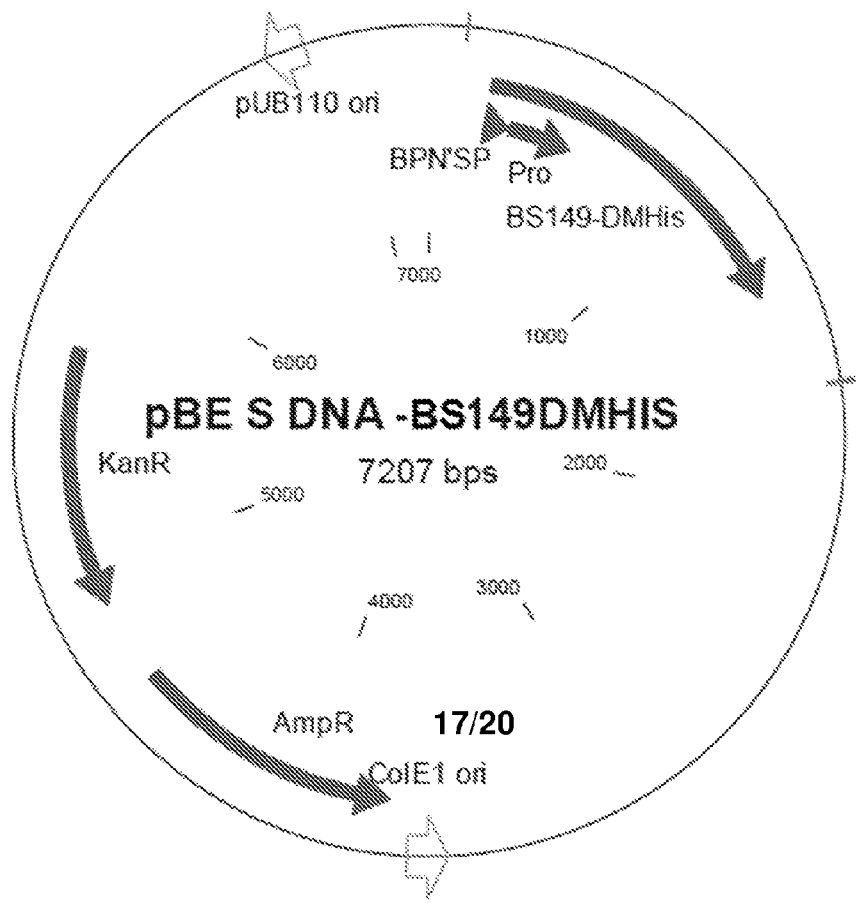

The gene coding for BS149-DM with a His-tag was cloned into a pUB-110 based *E. coli-B. subtilis* shuttle vector (pBES) using the MluI and BamHI site (FIG. 12). The polynucleotide sequence of a gene (BS149-DM) encoding an enzyme (polypeptide) of the invention and the encoded enzyme is shown in SEQUENCE ID NO 5. The corresponding amino acid sequence is numbered according to the subtilisin BPN' numbering scheme. Amino acids −107 to −1 comprise the signal sequence, the pre sequence and a pro sequence which are cleaved off upon full maturation. Amino acids 1-275 comprise the mature enzyme which exhibits the full catalytic activity. In order to enable a fast and efficient purification after amino acid 275 a C-terminal His-tag is attached as shown in SEQUENCE ID NO 5. As a consequence of the removal of a calcium binding site BS149-DM contains a deletion of 9 amino acids compared to subtilisin BPN' comprising the amino acids corresponding to L75, N76, N77, S78, I79, G80, V81, L82 and G83 in subtilisin BPN'. In order to maintain the subtilisin BPN' numbering for BS149-DM the numbering jumps from 74 to 83. In the shuttle vector, the expression of the gene is under the control of aprE promoter. The vector contained the pUB ori of replication for *Bacillus* and a kanamycin resistance marker. The vector also contained the ColE1 ori of replication and an ampicillin resistance marker for maintenance in *E. coli*. The resulting plasmid pBES-BS149DMHIS was propagated in *E. coli* TOP10 and transformed into *B. subtilis* GX4935 (ΔnprEΔaprE).). Using pBES-BS149DMHIS as the template, mutagenesis was carried out by the Quikchange method (Agilent). Alternatively other methods for site directed mutagenesis known in the art may be used (Sambrook et al., 1989.).

Figure 13:
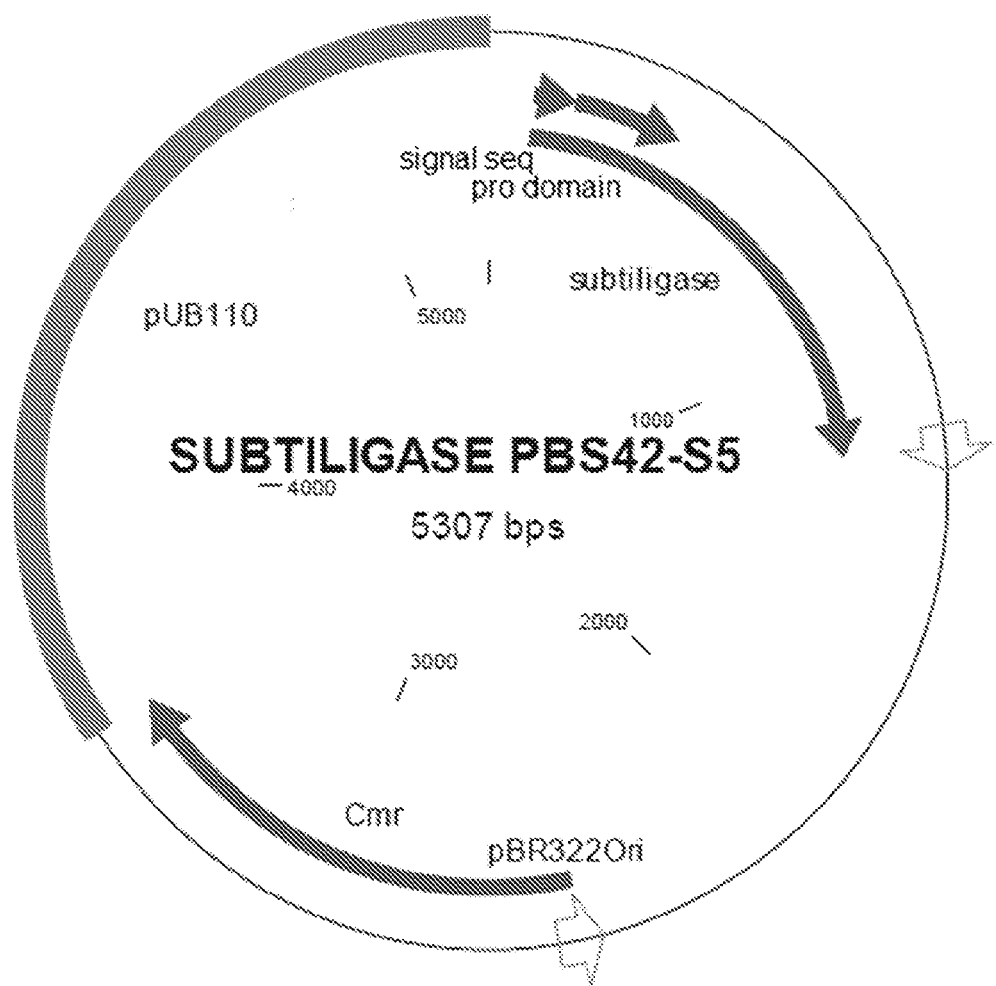

The gene of Subtiligase (Abrahmsen et al. 1991) was ordered at DNA2.0 (https://www.dna20.com/) in a DNA2.0 pJ201 cloning vector and recloned into E. coli-B. subtilis shuttle vector (pBS42 DSM 8748 obtained from DSMZ; pBS42-S5). The pJ201 vector (DNA 2.0) harboring Subtiligase as well as the pBS42 shuttle vector (DSMZ) were digested with EcoRI and BamHI (NEB). Linearized shuttle vector as well as Subtiligase insert were isolated from gel and ligated (LigaFast, Promega). The construct was transformed to E. coli MM294 strain (DSMZ). The plasmid pBS42-S5 was propagated in E. coli, isolated and validated by sequencing (FIG. 13). The validated DNA was used for transformation of either B. subtilis DB104 or B. subtilis GX4935. The B. subtilis GX4935 strain has reduced extracellular proteolytic activity (Kawamura and Doi 1984; Fahnestock and Fisher 1987). The addition of the wild type subtilisin to promote production of the mature form as reported by Abrahmsén et al. 1991 was not necessary.

Except for subtiligase and for the BS149-DM without His-tag in Example 23, in all experiments, enzymes were prepared making use of a C-terminal His-tag.

Production and Purification of Synthetic Subtilisin BPN' Variants:

Transformants in pBS42 shuttle vector were picked and grown on LB plate containing 10 µg/mL chloramphenicol at 37° C. for 16 h, were picked and inoculated into 5 mL of LB broth containing 10 µg/mL chloramphenicol. After 16 h of incubation at 37° C., 1% (v/v) of the cultures were inoculated to 1 liter terrific broth (12 g/l tryptone, 24 g/l yeast extract, 0.4% (v/v) glycerol, 17 mM $KH_2PO_4$ and 72 mM $K_2HPO_4$, 50 mg/L Trp, 50 mg/L Lys, 50 mg/L Met). Cultures were grown at 37° C. with vigorous shaking and incubation was continued for 48 hours. After 48 h expression, cells were isolated from the medium by centrifugation at 6,000 g for 20 min, 4° C. Subsequently, 5 g of $CaCl_2$ were added to the medium and the pH was adjusted back to 7.5. The precipitate was pelleted by centrifugation at 6,000 g for 20 min, 4° C. Ammoniumsulfate was added to the supernatant to a final concentration of 45% (w/v) to precipitate the enzyme. The precipitated enzyme was harvested by centrifugation at 8,000 g for 40 min, 4° C. The pellet was washed with 80% acetone, and resuspended in 15 mL water. The protein sample was desalted using a HiPrep 26/10 desalting column (GE healthcare) in buffer (20 mM Tricine, 1 mM $CaCl_2$ pH 7.5). The desalted proteins were loaded on a HiTrap Q HP column (GE healthcare). Flow through, which contains the enzyme, was collected and concentrated. The purity of the protein was analyzed by SDS-PAGE and enzyme concentration was determined by measuring the absorbtion at 280 nm (Stoscheck, C M. Quantitation of Protein. Methods in Enzymology 182: 50-69. 1990) e.g. by NanoDrop spectrophotometer (Thermo Fisher Scientific Inc). The specific extinction coefficient can be calculated at http://web.expasy.org/protparam/ according to Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607. Purity of about 90% or more was feasible. The obtained enzyme was provided at a concentration of about 2 mg/mL in an aqueous solution in 20 mM Tricine, 1 mM $CaCl_2$ pH 7.5. This enzyme solution was used as such for the (oligo)peptide fragment condensations and cyclisations.

Production and Purification of Synthetic Subtilisin BPN' Variants which Carry a His-tag:

A single microbial colony of B. subtilis containing a plasmid with the subtilisin variant gene of interest was inoculated in 5 mL LB with kanamycin (10 µg/mL) at 37° C. in a shaking incubator. To the 30 mL Terrific Broth supplemented with antibiotic (kanamycin 10 µg/mL) and amino acids (100 mg/L Trp, 100 mg/L Met and 100 mg/L Lys) 0.6 mL of the overnight culture was added. The cells were grown 48 h at 37° C. in a shaking incubator (200 rpm). The cells were harvested by centrifugation (15 min, 4,000 rpm, 4° C.). The medium (30 mL) was decanted and concentrated on Amicon-centrifugal unit (15 ml, 10 kDa MW cut-off) in two centrifugation steps (15 min, 4000 rpm, 4° C.). The concentrated medium (0.5 ml) was then exchanged for buffer A (25 mM Tricine, pH 7.5, 0.5M NaCl, 20 mM imidazole) in three washing/concentrating steps (14 ml buffer A, 10 min, 4,000 rpm, 4° C.). For His-tag purification Talon resin (2.5 ml, Clonetech) was added to a plastic column cartridge. The resin was washed with 5 mL MilliQ water and equilibrated with 5 mL of buffer A. The crude enzyme was loaded on the column and washed with 5 mL buffer A. The enzyme was eluted with 5 mL buffer B (25 mM Tricine, pH 7.5, 0.5M NaCl, 200 mM imidazole). The elute was concentrated on a Amicon-centrifugal unit (5 ml, 10 kDa MW cut-off) by centrifugation (15 min, 4000 rpm, 4° C.) and the buffer was exchanged to 25 mM Tricine, pH 7.5 in three washing/concentrating steps (5 ml buffer, 10 min, 4,000 rpm, 4° C.).

The purity and enzyme concentration was determined as described above Purity was more than 90%, The obtained aqueous solution (25 mM Tricine, pH 7.5) containing about 2 mg/ml of the obtained enzyme was used as such for the (oligo)peptide fragment condensations and cyclisations.

REFERENCES

Abrahmsén, L, J Tom, J Burnier, K A Butcher, A Kossiakoff, and J A Wells. 1991. "Engineering Subtilisin and Its Substrates for Efficient Ligation of Peptide Bonds in Aqueous Solution." Biochemistry 30 (17) (April 30): 4151-9. http://www.ncbi.nlm.nih.gov/pubmed/2021606.

Fahnestock S R, Fisher K E: Expression of the staphylococcal protein A gene in Bacillus subtilis by gene fusions utilizing the promoter from a Bacillus amyloliquefaciens alpha-amylase gene. J Bacteriol. 1986 March; 165(3): 796-804

Kawamura, Fujio, and Roy H. Doi. Construction of a Bacillus subtilis double mutant deficient in extracellular alkaline and neutral proteases. J Bacteriol. 1984 October; 160(1): 442-4

Ruan, Biao, Viktoriya London, Kathryn E Fisher, D Travis Gallagher, and Philip N Bryan. Engineering substrate preference in subtilisin: structural and kinetic analysis of a specificity mutant. Biochemistry. 2008 Jun. 24; 47(25): 6628-36.

Sambrook J, Fritsch E F, Maniatis T. 1989. Molecular Cloning: A Laboratory Manual. 2nd edition. Cold Spring Harbor Laboratory Press, Cold Spring Harbor, N.Y.

Wells, James A, Eugenio Ferrari, Dennis J Henner, David A Estell, and Ellson Y Chen. Cloning, sequencing, and secretion of Bacillus amyloliquefaciens subtilisin in Bacillus subtilis. Nucleic Acids Res. 1983 Nov. 25; 11(22):7911-25.

Enzymatic Fragment Condensation and Cyclisation Examples

Materials and Methods

Unless stated otherwise, chemicals were obtained from commercial sources and used without further purification. Analytical HPLC was performed on an HP1090 Liquid Chromatograph, using a reversed-phase column (Phenomenex, C18, 5 µm particle size, 150×4.6 mm) at 40° C. UV detection was performed at 220 nm using a UV-VIS 204 Linear spectrometer. The gradient program was: 0-25 min linear gradient ramp from 5% to 98% eluent B and from 25.1-30 min 5% eluent B (eluent A: 0.5 mL/L methane sulfonic acid (MSA) in H2O, eluent B 0.5 mL/L MSA in acetonitrile). The flow was 1 mL/min from 0-25.1 min and 2 mL/min from 25.2-29.8 min, then back to 1 mL/min until stop at 30 min. Injection volumes were 20 µL. Preparative HPLC was performed on a Varian PrepStar system using a stationary-phase column (Pursuit XRs, C18, 10 µm particle size, 500×41.4 mm). LC-MS was performed on an Agilent 1200 series Liquid Chromatograph, using a reversed-phase column (Phenomenex, C18, 5 µm particle size, 150×4.6 mm) at 40° C. UV detection and gradient program were as described for analytical HPLC. The molecular weights were determined using an Agilent 6130 quadrupole LC/MS system.

Protocol 1: N-Fmoc-Protected (oligo)peptide-OCam Esters were Synthesized as Described Below:

1 gram of Rink resin (4-((2,4-dimethoxyphenyl)(Fmoc amino)methyl)phenoxyalkyl linker, with a loading of 0.64 mmol/gram) was washed with dichloromethane (DCM, 2×2 min, 10 mL) and 1-methyl-2-pyrrolidone (NMP, 2×2 min, 10 mL) and Fmoc-deprotected using piperidine/NMP (1/4, v/v, 2×8 min, 10 mL). After washing with NMP (2×2 min, 10 mL), DCM (2×2 min, 10 mL) and NMP (2×2 min, 10 mL), iodoacetic acid (4 equiv.) was coupled to the resin using DCC (4 equiv.) and HOAt (4 equiv.) in DCM (45 min, 10 mL). After washing with NMP (2×2 min, 10 mL), DCM (2×2 min, 10 mL) and THF (2×2 min, 10 mL), the resin was loaded with an Fmoc-protected amino acid using 4 equiv. Fmoc-Xxx-OH and 10 equiv. DiPEA in DMF/THF (1/1, v/v, 10 mL) at 50° C. for 20 h. Here and in other parts of this disclosure 'Xxx' stands for one amino acid (variable as indicated in the Figures belonging to the examples below).

After washing with DMF (2×2 min, 10 mL), DCM (2×2 min, 10 mL) and NMP (2×2 min, 10 mL), standard SPPS protocols were followed to elongate the peptide (Weng C. Chan and Peter White, OUP Oxford, 2000). Cleavage from the resin and side-chain deprotection was performed using a mixture of trifluoroacetic acid (TFA), triisopropylsilane (TIS) and water (95/2.5/2.5, v/v/v, 15 mL) for 120 min. The crude peptide was precipitated using methyl tert-butyl ether (MTBE)/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Protocol 2: N-Fmoc-Protected (oligo)peptide-OCam-Xxx-NH$_2$ Esters were Synthesized as Described Below:

1 gram of Rink resin was washed with DCM (2×2 min, 10 mL) and NMP (2×2 min, 10 mL) and Fmoc-deprotected using piperidine/NMP (1/4, v/v, 2×8 min, 10 mL). After washing with NMP (2×2 min, 10 mL), DCM (2×2 min, 10 mL) and NMP (2×2 min, 10 mL), Fmoc-Xxx-OH (4 equiv.) was coupled to the resin using HBTU (4 equiv.), HOBt (4 equiv.) and DiPEA (8 equiv.) in NMP (45 min, 10 mL). After washing with NMP (2×2 min, 10 mL), DCM (2×2 min, 10 mL) and NMP (2×2 min, 10 mL), the resin was Fmoc-deprotected using piperidine/NMP (1/4, v/v, 2×8 min, 10 mL). After washing with NMP (2×2 min, 10 mL), DCM (2×2 min, 10 mL) and NMP (2×2 min, 10 mL), iodoacetic acid (4 equiv.) was coupled using DCC (4 equiv.) and HOAt (4 equiv.) in DCM (45 min, 10 mL). After washing with NMP (2×2 min, 10 mL), DCM (2×2 min, 10 mL) and THF (2×2 min, 10 mL), an Fmoc-protected amino acid was coupled using 4 equiv. Fmoc-Xxx-OH and 10 equiv. DiPEA in DMF/THF (1/1, v/v, 10 mL) at 50° C. for 20 h. After washing with DMF (2×2 min, 10 mL), DCM (2×2 min, 10 mL) and NMP (2×2 min, 10 mL), standard SPPS protocols were followed to elongate the peptide (Weng C. Chan and Peter White, OUP Oxford, 2000). Cleavage from the resin and side-chain deprotection was performed using a mixture of TFA/TIS/water (95/2.5/2.5, v/v/v, 15 mL) for 120 min. The crude peptide was precipitated using MTBE/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Protocol 3: N-Fmoc-Protected (oligo)peptide-OCam-Xxx-OH Esters were Synthesized as Described Below:

1 gram of Trityl resin (2-chloro-chlorotrityl linker, with a loading of 1.0 mmol/gram) was washed with DCM (2×2 min, 10 mL) and Fmoc-Xxx-OH (2 equiv.) was coupled to the resin using DiPEA (5 equiv.) in DCM (30 min, 10 mL). After washing with DMF (2×2 min, 10 mL), the unreacted chlorotrityl groups were capped using DCM/MeOH/DiPEA (80/15/5, v/v/v, 2×10 min, 10 mL). The resin was washed with NMP (2×2 min, 10 mL), DCM (2×2 min, 10 mL) and NMP (2×2 min, 10 mL) and Fmoc-deprotected using piperidine/NMP (1/4, v/v, 2×8 min, 10 mL). After washing with NMP (2×2 min, 10 mL), DCM (2×2 min, 10 mL) and NMP (2×2 min, 10 mL), iodoacetic acid (4 equiv.) was coupled using DCC (4 equiv.) and HOAt (4 equiv.) in DCM (45 min, 10 mL). After washing with NMP (2×2 min, 10 mL), DCM (2×2 min, 10 mL) and THF (2×2 min, 10 mL), an Fmoc-protected amino acid was coupled using 4 equiv. Fmoc-Xxx-OH and 10 equiv. DiPEA in DMF/THF (1/1, v/v, 10 mL) at 50° C. for 20h. After washing with DMF (2×2 min, 10 mL), DCM (2×2 min, 10 mL) and NMP (2×2 min, 10 mL), standard SPPS protocols were followed to elongate the peptide (Weng C. Chan and Peter White, OUP Oxford, 2000). Cleavage from the resin and side-chain deprotection was performed using a mixture of TFA/TIS/water (95/2.5/2.5, v/v/v, 15 mL) for 120 min. The crude peptide was precipitated using MTBE/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Protocol 4: (oligo)peptide C-Terminal Amide Nucleophiles were Synthesized as Described Below:

1 gram of Rink resin (4-((2,4-dimethoxyphenyl)(Fmoc-amino)methyl)-phenoxyalkyl linker, with aloading of 0.64 mmol/gram) was washed with DCM (2×2 min, 10 mL) and NMP (2×2 min, 10 mL) and Fmoc-deprotected using piperidine/NMP (1/4, v/v, 2×8 min, 10 mL). Standard SPPS protocols were followed to elongate the peptide (Weng C. Chan and Peter White, OUP Oxford, 2000). Cleavage from the resin and side-chain deprotection was performed using a mixture of TFA/TIS/water (95/2.5/2.5, v/v/v, 15 mL) for 120 min. The crude peptide was precipitated using MTBE/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Protocol 5: N-Acetyl-Protected (oligo)peptide Activated Esters were Synthesized as Described Below:

After SPPS of the desired sequence according to one of the protocols 1-3, the resin bound peptide was Fmoc-deprotected using piperidine/NMP (1/4, v/v, 2×8 min, 10 mL). The resin was washed with NMP (2×2 min, 10 mL), DCM (2×2 min, 10 mL) and NMP (2×2 min, 10 mL) and the peptide N-terminal amine function was acetylated using a mixture of Ac$_2$O (10 vol %), DiPEA (5 vol %), HOBt (0.2 wt %) in NMP (2×10 min, 10 mL). The resin was washed with NMP (3×2 min, 10 mL) and DCM (3×2 min, 10 mL). Cleavage from the resin and side-chain deprotection was performed using a mixture of TFA/TIS/water (95/2.5/2.5, v/v/v, 15 mL) for 120 min. The crude peptide was precipitated using MTBE/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Protocol 6: (oligo)peptide C-Terminal Acids were Synthesized as Described Below:

1 gram of Trityl resin (2-chloro-chlorotrityl linker, with a loading of 1.0 mmol/gram) was washed with DCM (2×2 min, 10 mL) and Fmoc-Xxx-OH (2 equiv.) was coupled to the resin using DiPEA (5 equiv.) in DCM (30 min, 10 mL). After washing with DMF (2×2 min, 10 mL), the unreacted chlorotrityl groups were capped using DCM/MeOH/DiPEA (80/15/5, v/v/v, 2×10 min, 10 mL). The resin was washed with NMP (2×2 min, 10 mL), DCM (2×2 min, 10 mL) and NMP (2×2 min, 10 mL) and standard SPPS protocols were followed to elongate the peptide (Weng C. Chan and Peter White, OUP Oxford, 2000). Cleavage from the resin and side-chain deprotection was performed using a mixture of TFA/TIS/water (95/2.5/2.5, v/v/v, 15 mL) for 120 min. The crude peptide was precipitated using MTBE/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Protocol 7: Synthesis Partially Protected (oligo)peptide Fragments

During SPPS of the peptide sequence according to one of the protocols 1-6, at the desired position a differently (TFA stable) protected amino acid was coupled such as Fmoc-Asp(OcHex)-OH, Fmoc-Glu(OBn)-OH or Fmoc-Lys(Alloc)-OH. Cleavage from the resin and side-chain deprotection, except for the TFA stable cHex, Bn or Alloc group which remained unaffected, was performed using a mixture of TFA/TIS/water (95/2.5/2.5, v/v/v, 15 mL) for 120 min. The crude peptide was precipitated using MTBE/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

COUPLING EXAMPLES

Note: The enzyme denoted as BS149-DM (SEQUENCE ID NO:5) contains a deletion of amino acids 75-83 and mutations Q2K, S3C, P5S, S9A, I31L, K43N, M50F, A73L, E156S, G166S, G169A, S188P, Q206C, N212G, Y217L, N218S, S221C, P225A, T254A and Q271E compared to SEQUENCE ID NO:2. On the basis of the present disclosure, common general knowledge and optionally a limited amount of route testing, the skilled person in the art may revert one or more of mutations Q2K, S3C, PSS, S9A, I31L, K43N, M50F, A73L, E156S, G166S, G169A, S188P, Q206C, N212G, Y217L, N218S, T254A and Q271E or make different substitutions at one or more of the positions Q2, S3, P5, S9, I31, K43, M50, A73, E156, G166, G169, S188, Q206, N212, N218S, T254, Q271 while still having significantly improved properties compared to Subtiligase (see for instance example 24).

The enzyme denoted as Subtiligase contains the mutations S221C and P225A compared to SEQUENCE ID NO:2.

The enzymes of the invention used in the Examples 1-23 have all the mutations of BS149-DM, plus optional additional mutations as mentioned in the Examples.

As indicated below, enzymes with further mutations were made using the technology described above.

Example 1: Enzymatic Oligopeptide Fragment Coupling Using Different BS149-DM Mutants To test the activity and S/H ratio of the different mutants, the following standard reaction was performed. 800 µL of phosphate buffer (100 mM, pH 8.0) was added to a mixture of 100 µL tripeptide C-terminal amide stock solution (0.01 mmol H-Ala-Leu-Arg-NH$_2$.2TFA in 300 µL water) and 100 µL pentapeptide C-terminal Cam-ester stock solution (0.01 mmol Ac-Asp-Phe-Ser-Lys-Leu-OCam.TFA in 1200 µL water). To this mixture 5.5 µg enzyme was added and the reaction mixture was shaken (150 rpm) at room temperature. After 30 min a 500 µL aliquot of the reaction mixture was withdrawn and quenched with 500 µL MSA/water (1/99, v/v) and analyzed by LC-MS. The product, hydrolysed pentapeptide C-terminal Cam-ester and remaining pentapeptide C-terminal Cam-ester peaks were integrated.

Figure 1B:
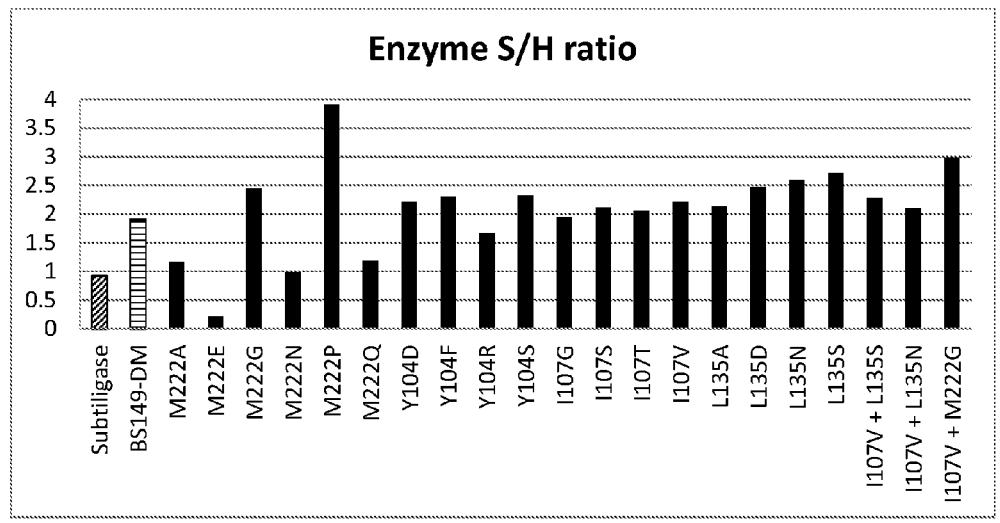

The activity of the different BS149-DM mutants is defined as the total of the amount of product and the amount of hydrolysed pentapeptide C-terminal Cam-ester divided by the total of the amount of product, hydrolysed pentapeptide C-terminal Cam-ester and remaining Cam-ester, within the specified reaction time. The most active mutant was set to 100% (see FIG. 1A). The S/H ratio of the different BS149-DM mutants is defined as the amount of product divided by the amount of hydrolysed pentapeptide C-terminal Cam-ester, within the specified time (see FIG. 1B).

Activity and S/H ratio in other examples were determined in the same way, unless specified otherwise.

Conclusions: clearly, BS149-DM has a twice higher activity and an improved S/H ratio (1.8 versus 0.9) as compared to subtiligase. The M222 position proved very important for the S/H ratio of the enzyme. Especially good results were obtained with the M222G and M222P mutants of BS149-DM. All BS149-DM variants containing a P4 pocket mutation (positions Y104, I107 and L135) have a comparable S/H ratio to BS149-DM. However, for certain mutations, the activity of the BS149-DM variants was drastically improved. Particularly good results were obtained with the mutations Y104S, I107V, L135D, L135N and L135S. When combining P4 pocket mutations, BS149-DM variants with even higher activity were obtained, i.e. I107V+L135S and I107V+L135N. When P4 pocket mutations were combined with P1' pocket mutations, a very active BS149-DM variant with an increased S/H ratio as compared to BS149-DM was obtained, e.g. I107V+M222G.

Figure 2A:
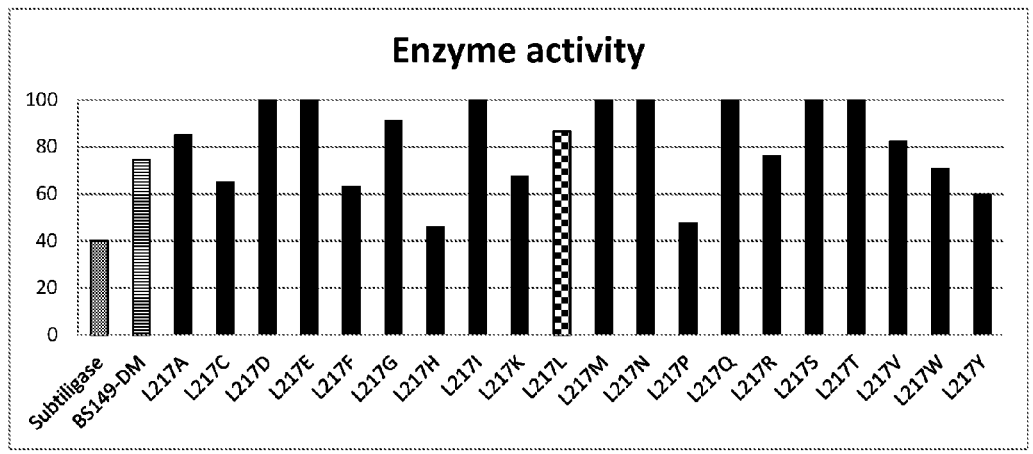
FIGS. 2A and 2B show activity respectively S/H ratio of different BS149-DM+M222P+L217 mutants; all indicated mutations on L217 are additional to those of BS149-DM+M222P.
Figure 2B:
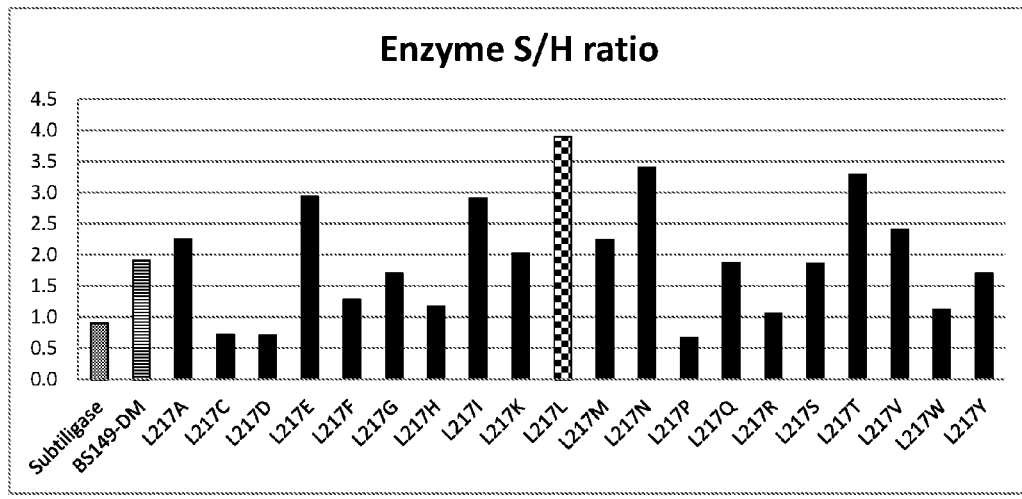

Example 2: Enzymatic Oligopeptide Fragment Coupling Using Different BS149-DM+M222P+L217 Mutants To test the activity and S/H ratio of the different mutants, the same reaction as described in Example 1 was performed. The activity of the different BS149-DM+M222P+L217 mutants is defined as the total of the amount of product and the amount of hydrolysed oligopeptide C-terminal Cam-ester divided by the total of the amount of product, hydrolysed oligopeptide C-terminal Cam-ester and remaining Cam-ester. The most active mutant was set to 100% (see FIG. 2A). The S/H ratio of the different BS149-DM+M222P+L217 mutants is defined as the amount of product divided by the amount of hydrolysed C-terminal Cam-ester (see FIG. 2B).

Conclusions: clearly, all BS149-DM+M222P+L217 mutants have an improved S/H and similar or improved activity as compared to subtiligase and some of them have an increased activity compared to BS149-DM+M222P. Particularly good results were obtained with the mutations L217N, L217T, L217E, L2171, L217V and L217A. The L217 position proved not only very important for activity and S/H ratio but is even more important for the substrates scope, as described in Example 5.

Example 3: Mapping the P4 Pocket Substrate Specificity of Different BS149-DM Mutants Containing a P4 Pocket Mutation (Positions Y104, I107 and L135)

To determine the P4 pocket substrate specificity of the different mutants, the following standard reaction was performed. 800 μL of phosphate buffer (100 mM, pH 8.0) was added to a mixture of 100 μL tripeptide C-terminal amide stock solution (0.01 mmol H-Ala-Leu-Arg-NH$_2$.2TFA in 300 μL water) and 200 μL pentapeptide C-terminal Cam-ester stock solution (0.01 mmol Ac-Asp-Xxx-Ser-Lys-Leu-OCam.TFA in 1.2 mL water+1 mL Acn). Couplings with all these peptide esters were performed, differing in the amino acid at this position, as indicated in FIGS. 3A-3C.

To this mixture 5.5 μg enzyme was added and the reaction mixture was shaken (150 rpm) at room temperature. After 30 min a 550 μL aliquot of the reaction mixture was withdrawn and quenched with 500 μL MSA/water (1/99, v/v) and analyzed by LC-MS. The product, hydrolysed pentapeptide C-terminal Cam-ester and remaining pentapeptide C-terminal Cam-ester peaks were integrated. The activity is defined as the amount of product divided by the total of the amount of product, hydrolysed pentapeptide C-terminal Cam-ester and remaining pentapeptide C-terminal Cam-ester, within the specified reaction time. The most active substrate was set to 100%, see FIGS. 3A-C.

Figure 3A:
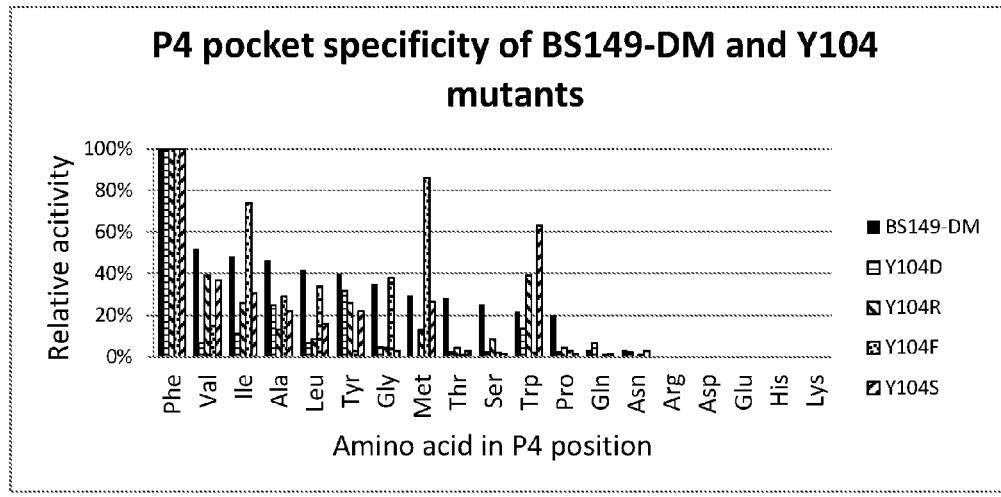
FIG. 3A: The P4 pocket specificity of BS149-DM and BS149-DM+Y104 mutants.
Figure 3B:
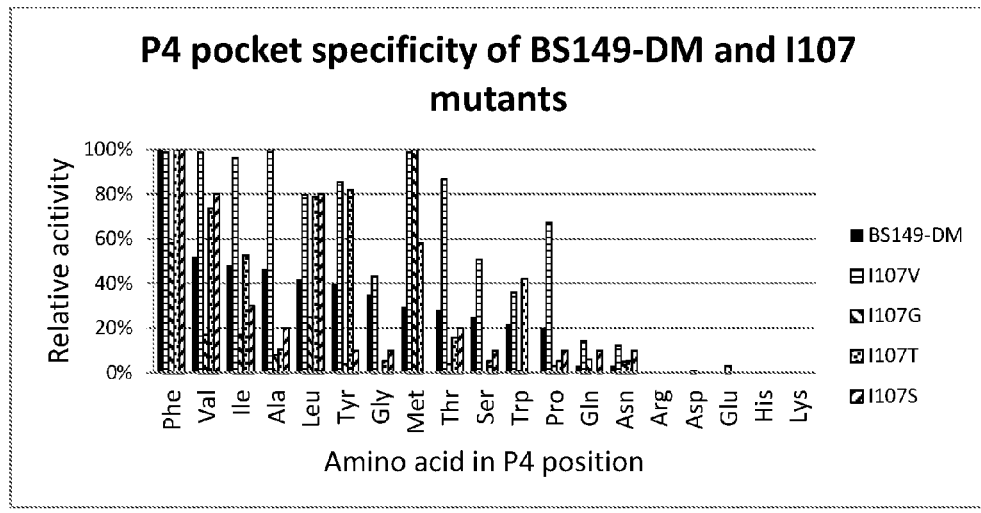
FIG. 3B: The P4 pocket specificity of BS149-DM and BS149-DM+I107 mutants.
Figure 3C:
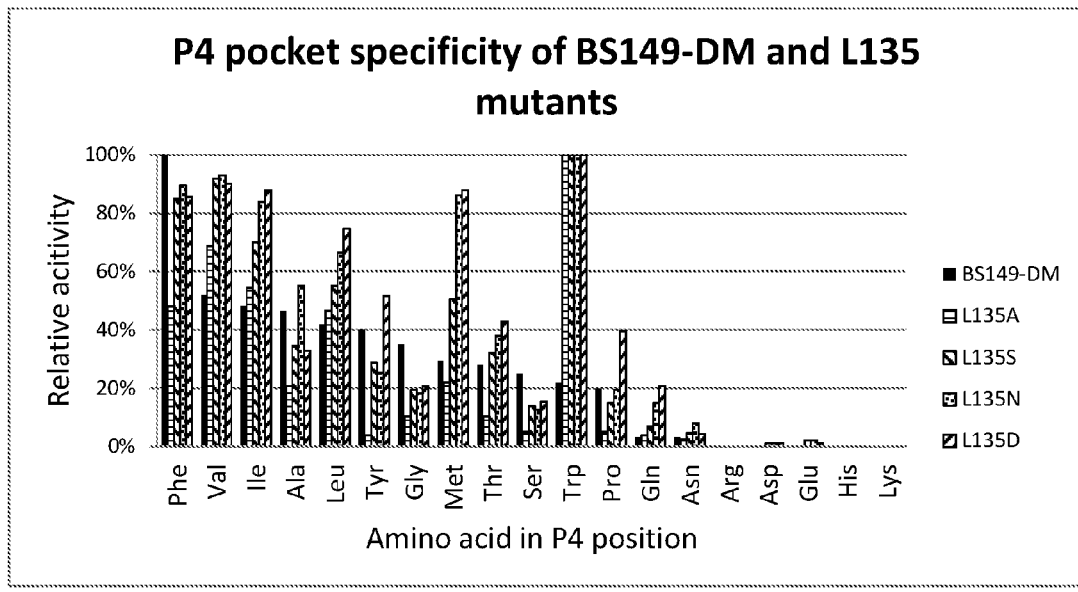
FIG. 3C: The P4 pocket specificity of BS149-DM and BS149-DM+L135 mutants
Figure 4A:
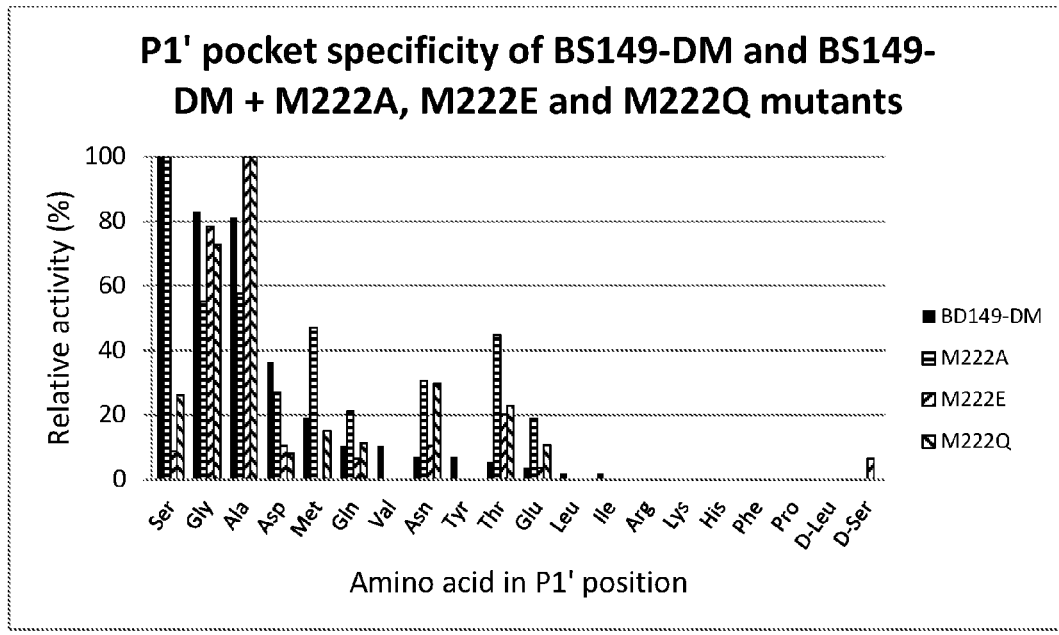
FIG. 4A: The P1' pocket specificity of BS149-DM and BS149-DM+M222A, M222E and M222Q mutants
Figure 4B:
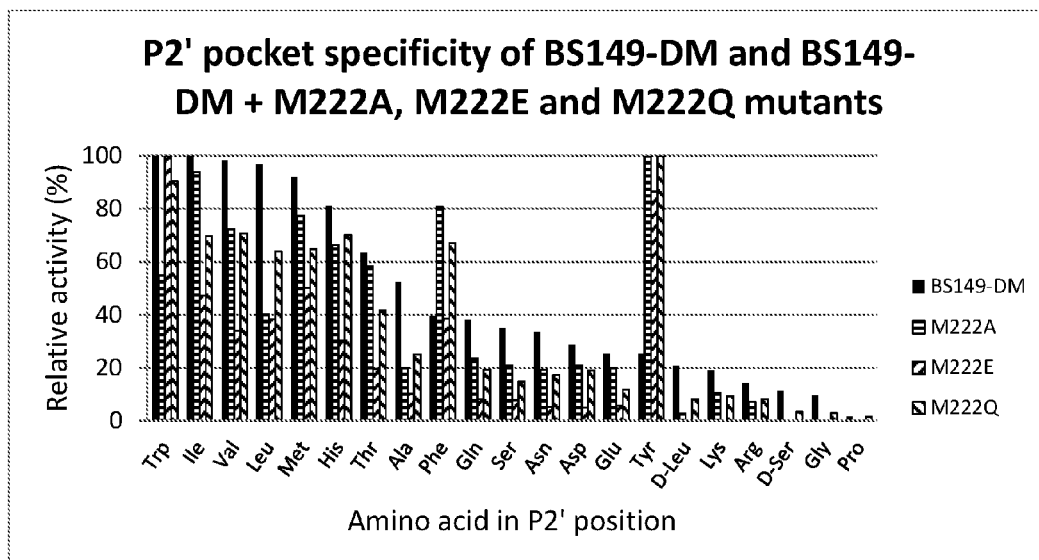
FIG. 4B: The P2' pocket specificity of BS149-DM and BS149-DM+M222A, M222E and M222Q mutants
Figure 4C:
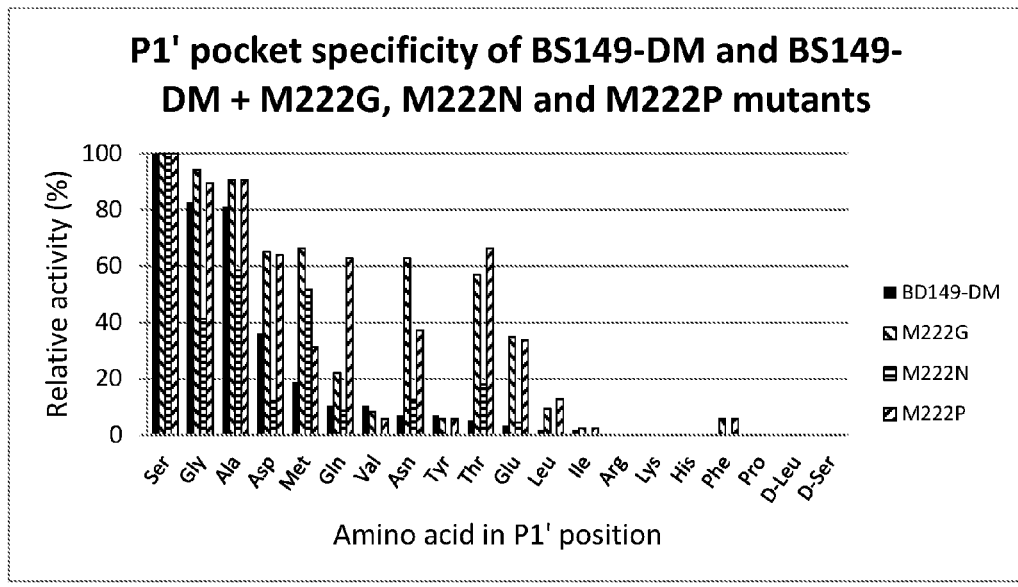
FIG. 4C: The P1' pocket specificity of BS149-DM and BS149-DM+M222G, M222N and M222P mutants
Figure 4D:
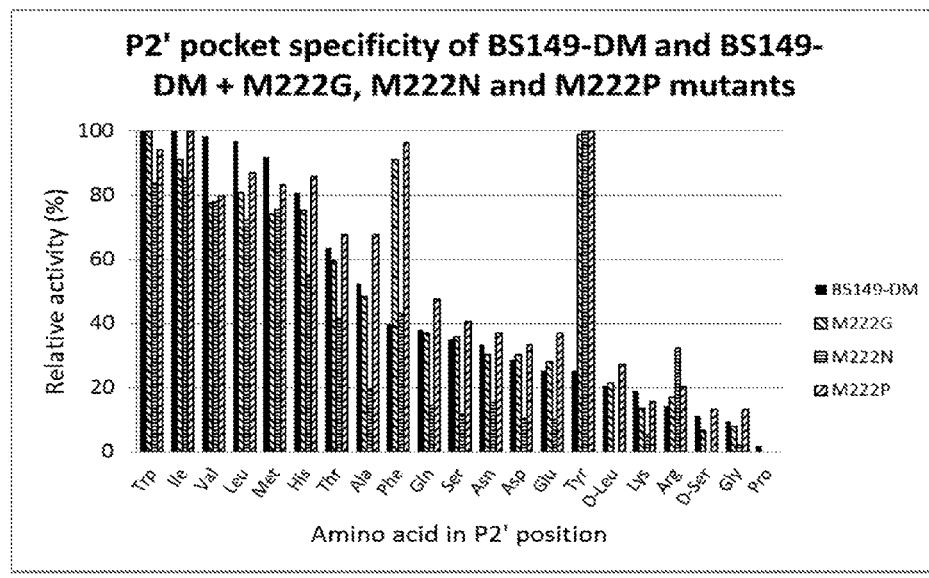
FIG. 4D: The P2' pocket specificity of BS149-DM and BS149-DM+M222G, M222N and M222P mutants
Figure 5A:
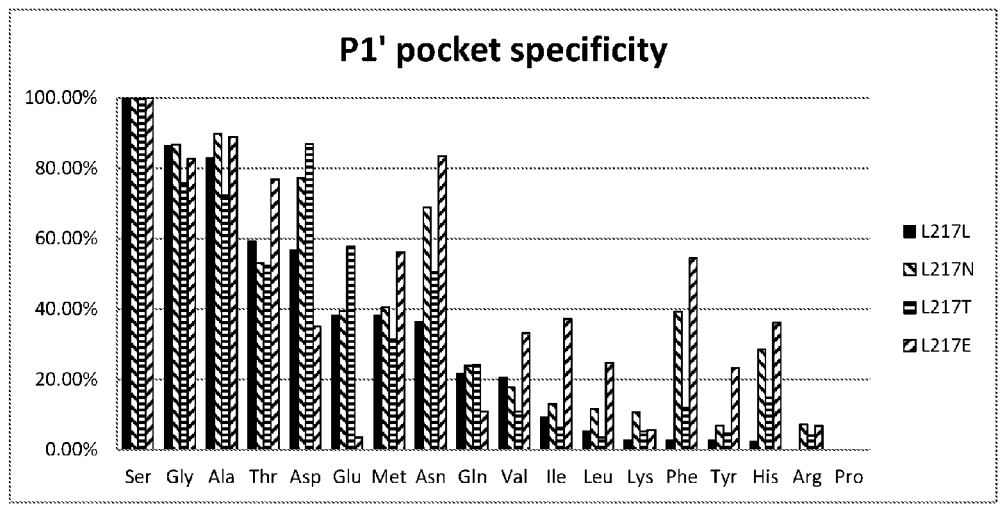
FIG. 5A: The P1' pocket specificity of BS149-DM+M222P+L217N, L217T and L217E mutants
Figure 5B:
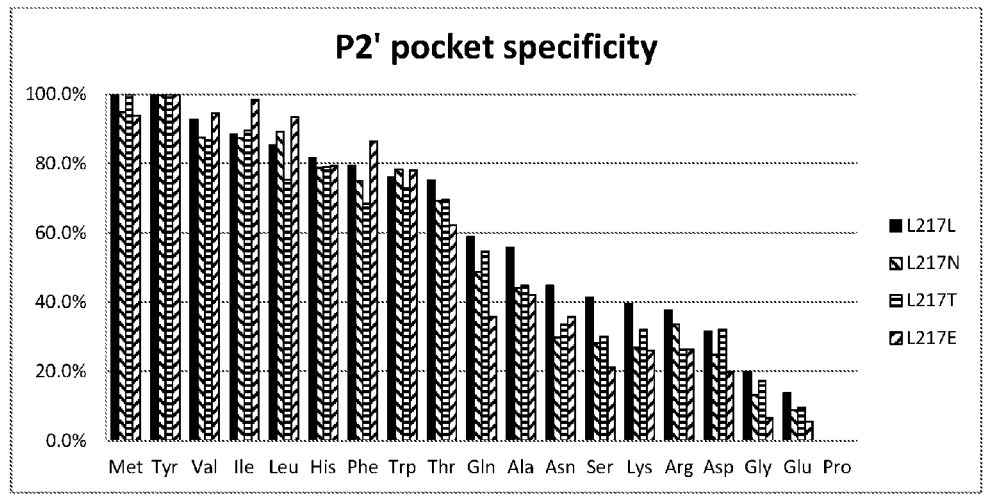
FIG. 5B: The P2' pocket specificity of BS149-DM+M222P+L217N, L217T and L217E mutants
Figure 5C:
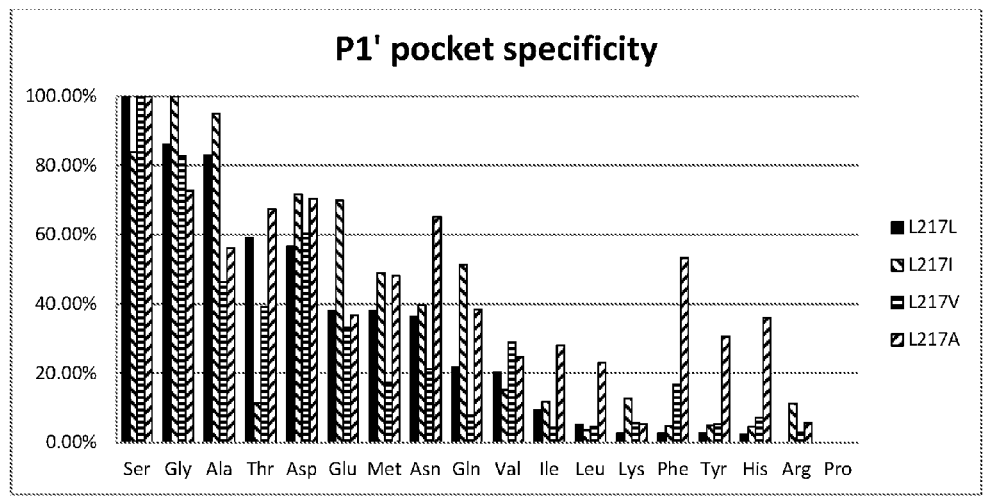
FIG. 5C: The P1' pocket specificity of BS149-DM+M222P+L2171, L217V and L217A mutants
Figure 5D:
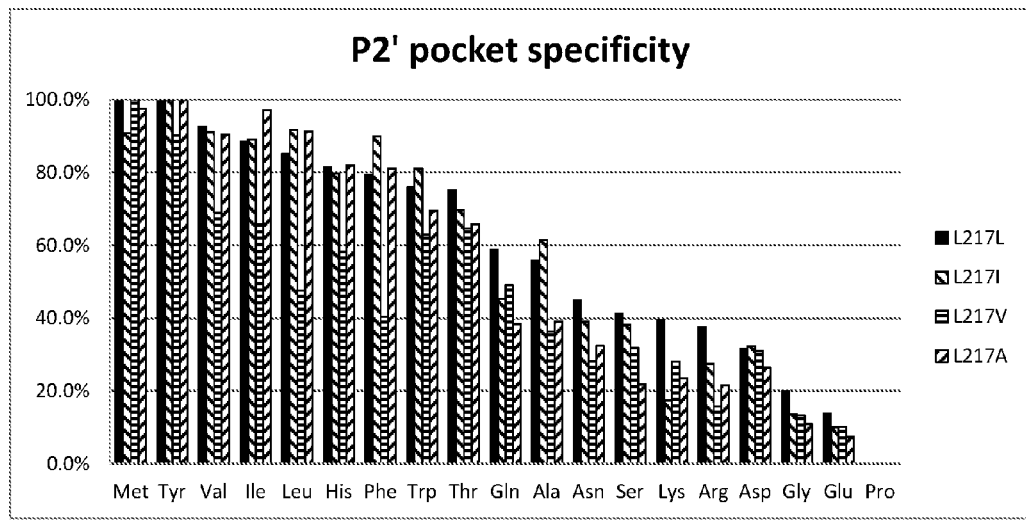
FIG. 5D: The P2' pocket specificity of BS149-DM+M222P+L2171, L217V and L217A mutants
Figure 5E:
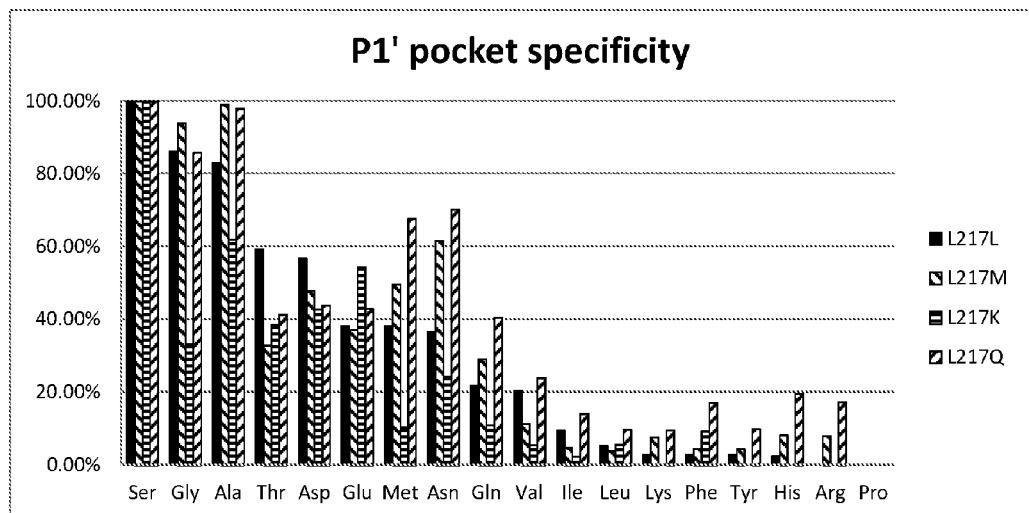
FIG. 5E: The P1' pocket specificity of BS149-DM+M222P+L217M, L217K and L217Q mutants
Figure 5F:
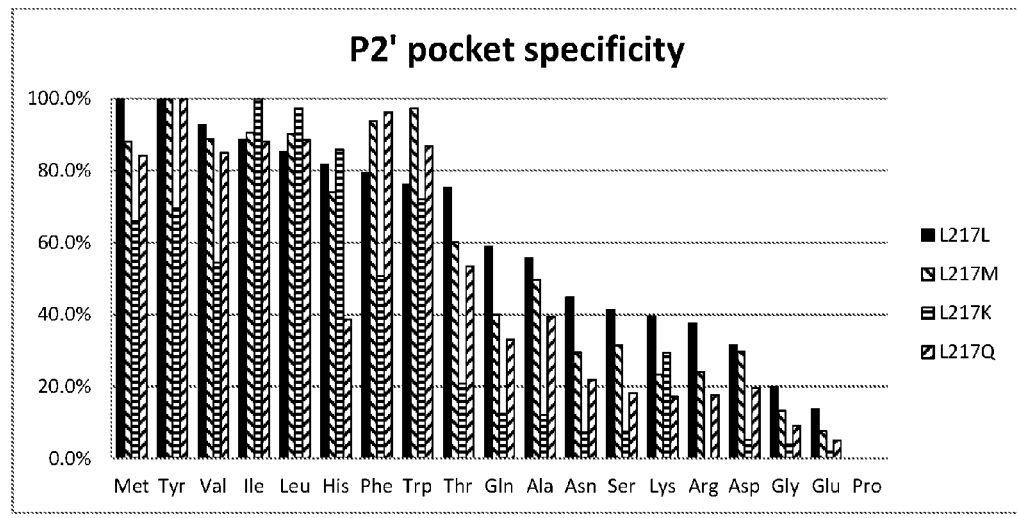
FIG. 5F: The P2' pocket specificity of BS149-DM+M222P+L217M, L217K and L217Q mutants
Figure 5G:
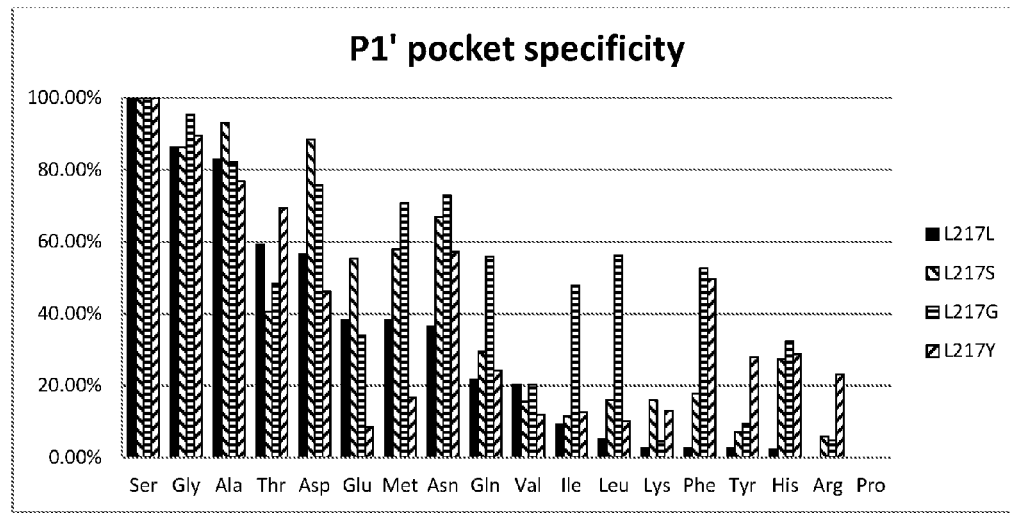
FIG. 5G: The P1' pocket specificity of BS149-DM+M222P+L217S, L217G and L217Y mutants
Figure 5H:
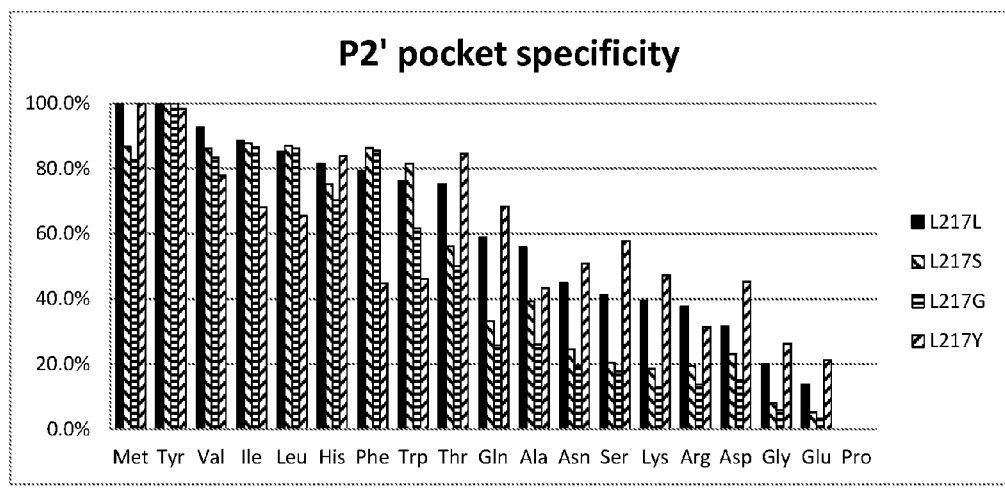
FIG. 5H: The P2' pocket specificity of BS149-DM+M222P+L217S, L217G and L217Y m When referring to a noun (e.g. a compound, an additive, etc.) in the singular, the plural is meant to be included, unless it follows from the context that it should refer to the singular only.
Figure 5I:
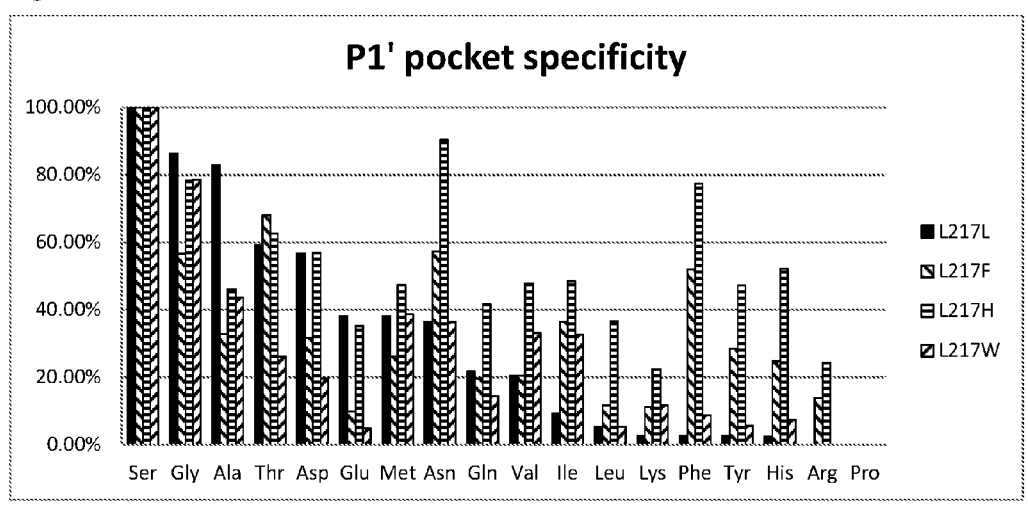
Figure 5J:
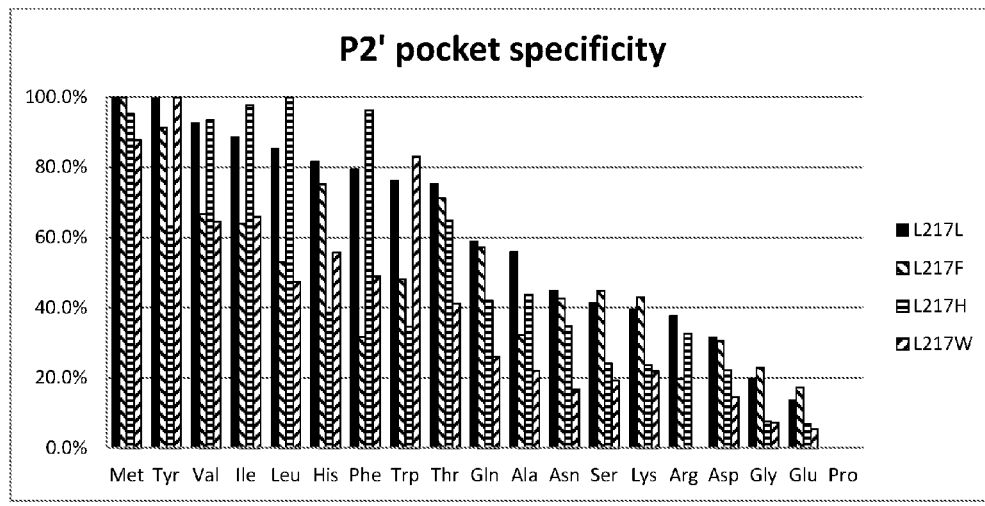
Figure 5K:
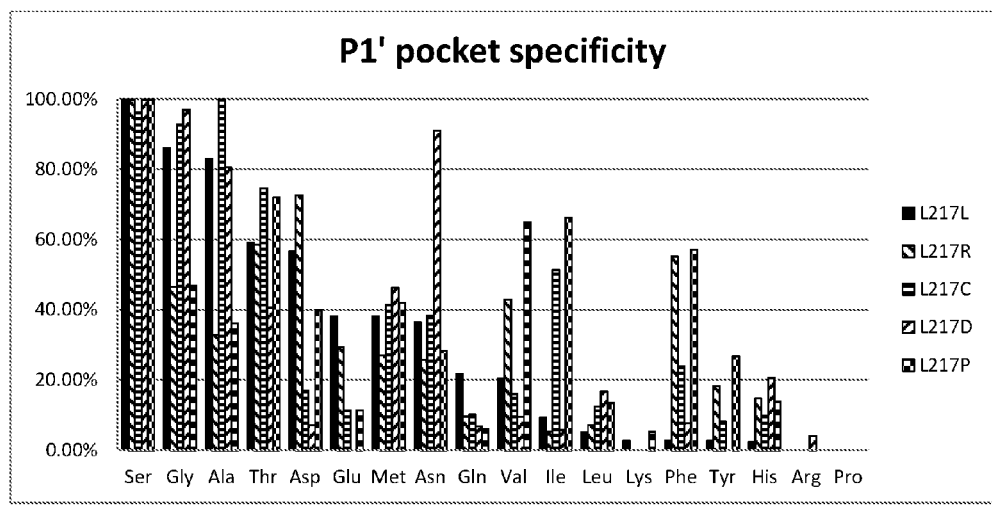
Figure 5L:
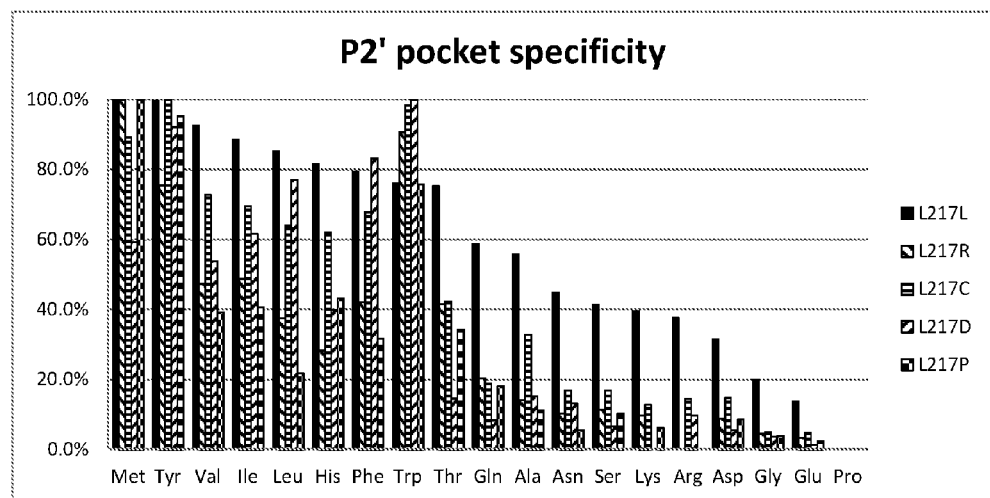
Figure 6A:
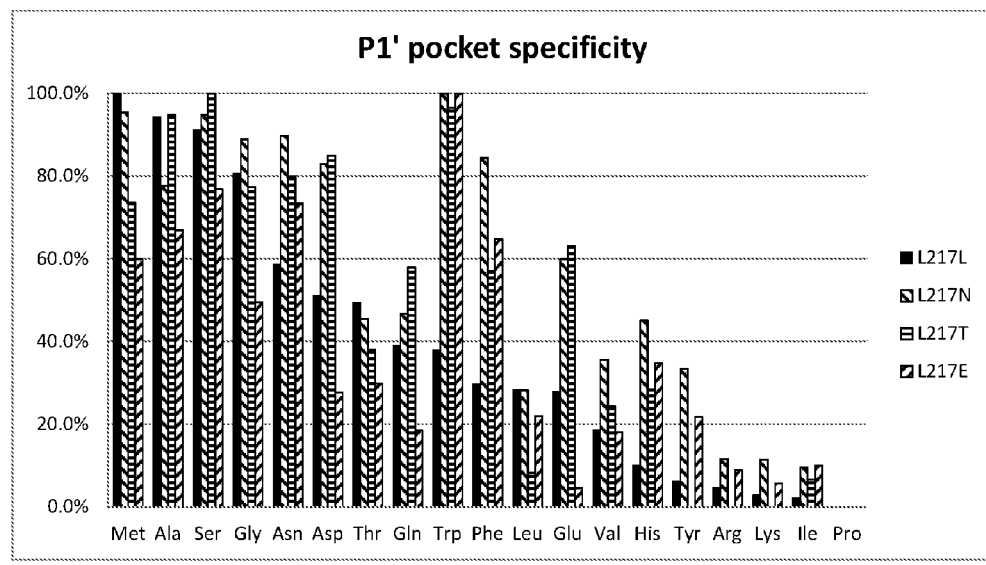
Figure 6B:
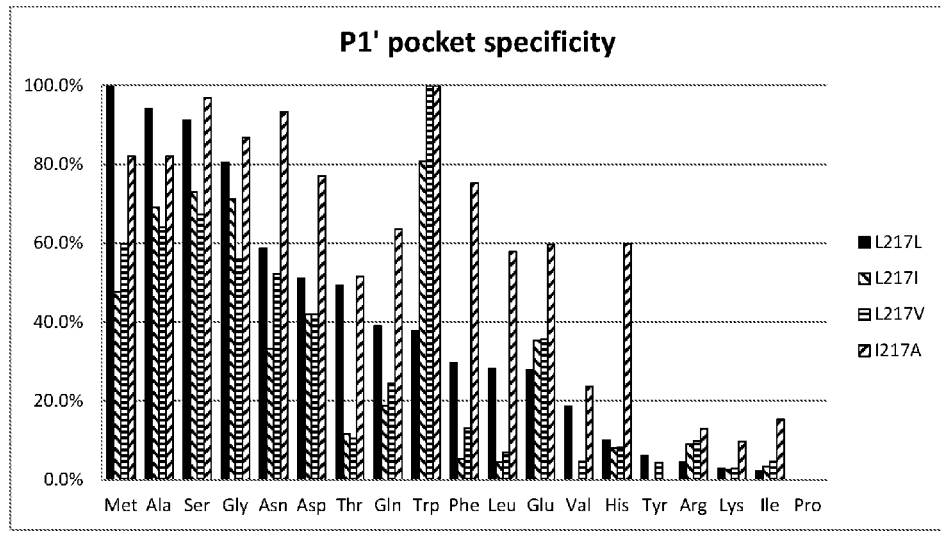
Figure 6C:
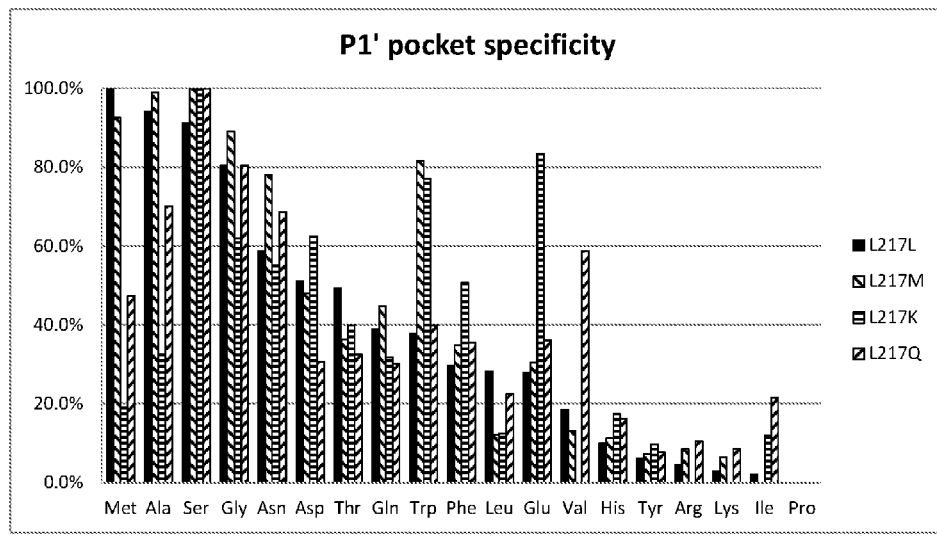
Figure 6D:
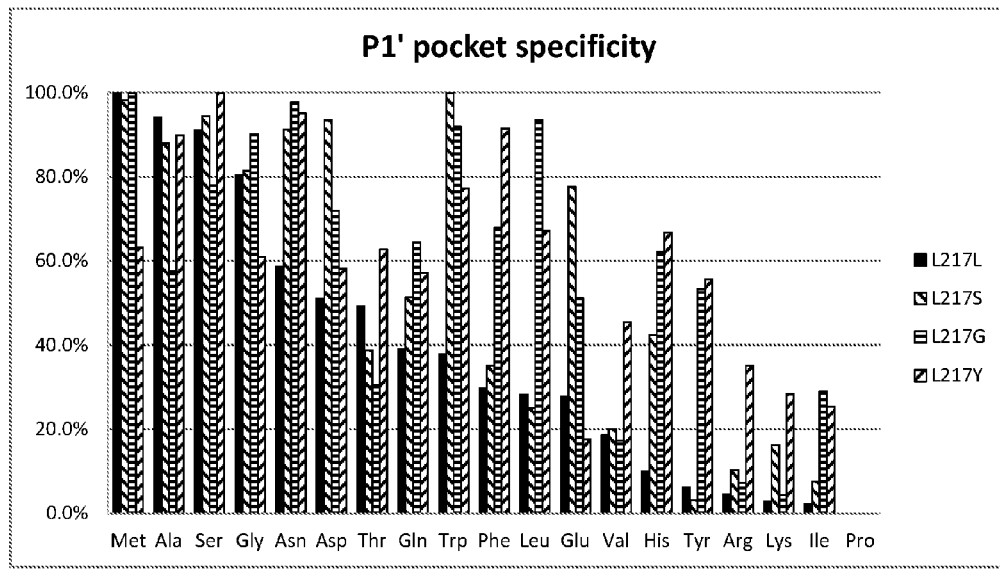
Figure 6E:
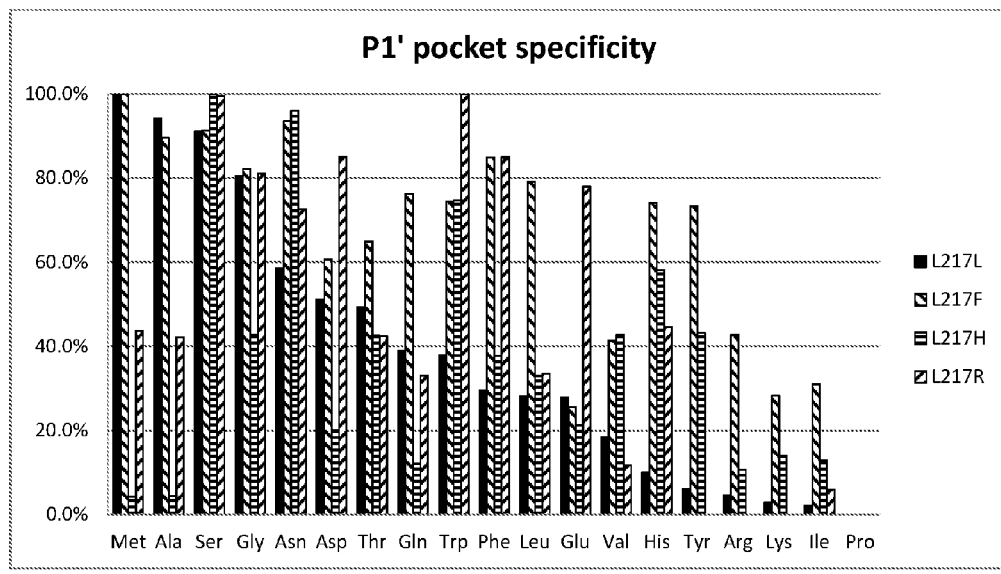
Figure 6F:
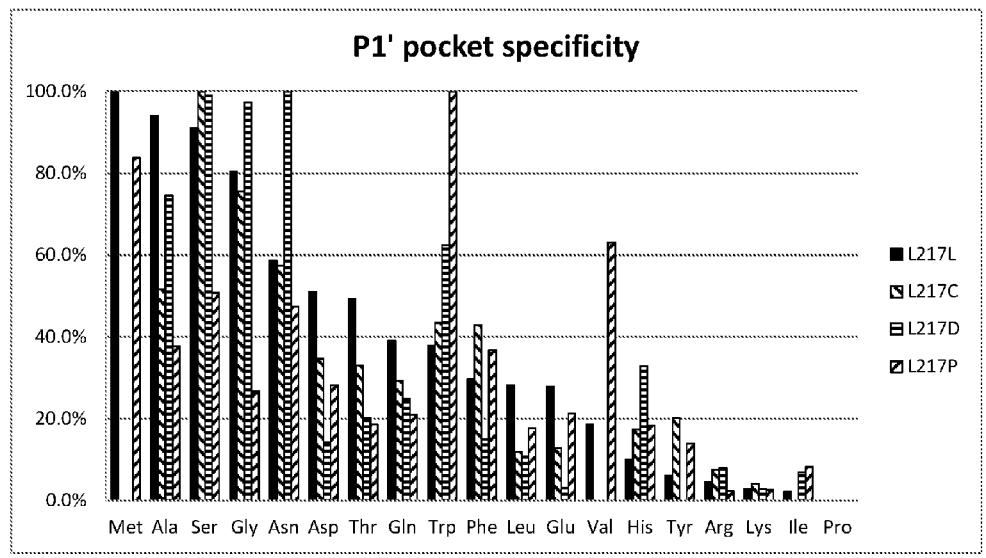

Conclusions: as evident from FIGS. 3A-C, the P4 substrate scope of the BS149-DM mutants with a P4 mutation (on positions Y104, I107 and/or L135) clearly differs from that of BS149-DM which may be advantageous for various particular peptide sequences. Several mutants show a much broader P4 substrate scope than BS149-DM. This is in particular the case with mutations I107V, L135D, L135N and L135S.

Example 4: Mapping the P1' and P2' Pocket Substrate Specificity of Different BS149-DM+M222 Mutants To determine the P1' and P2' pocket substrate specificity of the different mutants, the following two standard reactions were performed. 800 μL of phosphate buffer (100 mM, pH 8.0) was added to a mixture of 100 μL tripeptide C-terminal amide stock solution (0.01 mmol H-Xxx-Leu-Arg-NH$_2$.2TFA for P1' and H-Ala-Xxx-Arg-NH$_2$.2TFA for P2' in 300 μL water) and 100 μL pentapeptide C-terminal Cam-ester stock solution (0.01 mmol Ac-Asp-Phe-Ser-Lys-Leu-OCam.TFA in 1200 μL water). To this mixture 5.5 μg enzyme was added and the reaction mixture was shaken (150 rpm) at room temperature. After 30 min a 550 μL aliquot of the reaction mixture was withdrawn and quenched with 500 μL MSA/water (1/99, v/v) and analyzed by LC-MS. The product, hydrolysed pentapeptide C-terminal Cam-ester and remaining pentapeptide C-terminal Cam-ester peaks were integrated. The activity is defined as the amount of product divided by the total of the amount of product, hydrolysed pentapeptide C-terminal Cam-ester and remaining pentapeptide C-terminal Cam-ester, within the specified reaction time. The most active substrate was set to 100%, The P1' and P2' pocket substrate specificities of different BS149-DM+M222 mutants are shown in FIGS. 4 A-D. The coupling with tryptophan in P1' position was not determined due to overlap in the LC-MS peaks.

Conclusions: as evident from FIGS. 4A-D, the P1' and P2' substrate scopes of the BS149-DM mutants with a P1' mutation on position M222 clearly differs from that of BS149-DM which may be advantageous for various particular peptide sequences. Several mutants show a much broader P1' and P2' substrate scope than BS149-DM. This is in particular the case with mutations M222G and M222P.

Example 5: Mapping the P1' and P2' Pocket Substrate Specificity of Different BS149-DM+M222P+L217 Mutants To determine the P1' and P2' pocket substrate specificity of the different mutants, the same reactions and analyses were performed as described in Example 4. The P1' and P2' pocket substrate specificities of different BS149-DM+M222P+L217 mutants are shown in FIGS. 5A-L.

Figure 7A:
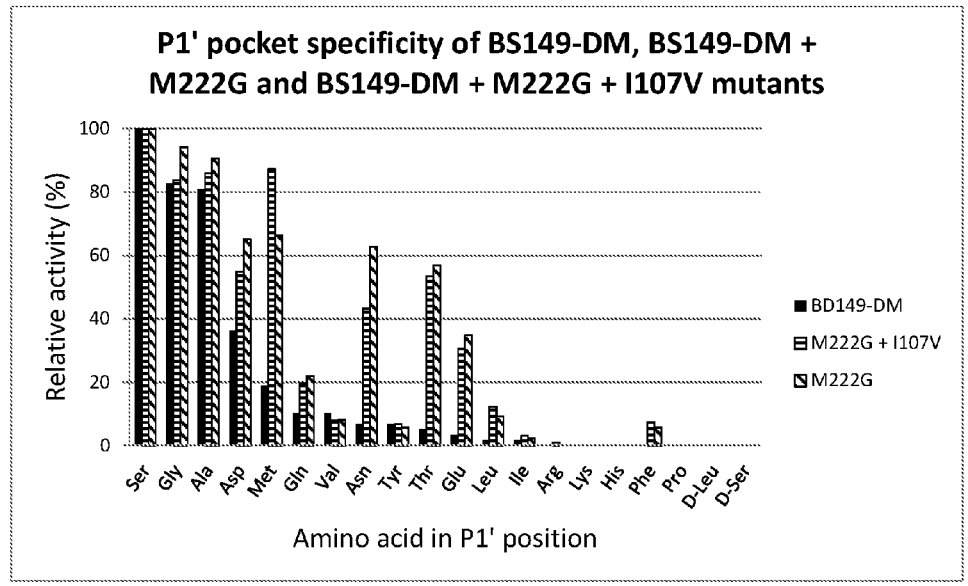
Figure 7B:
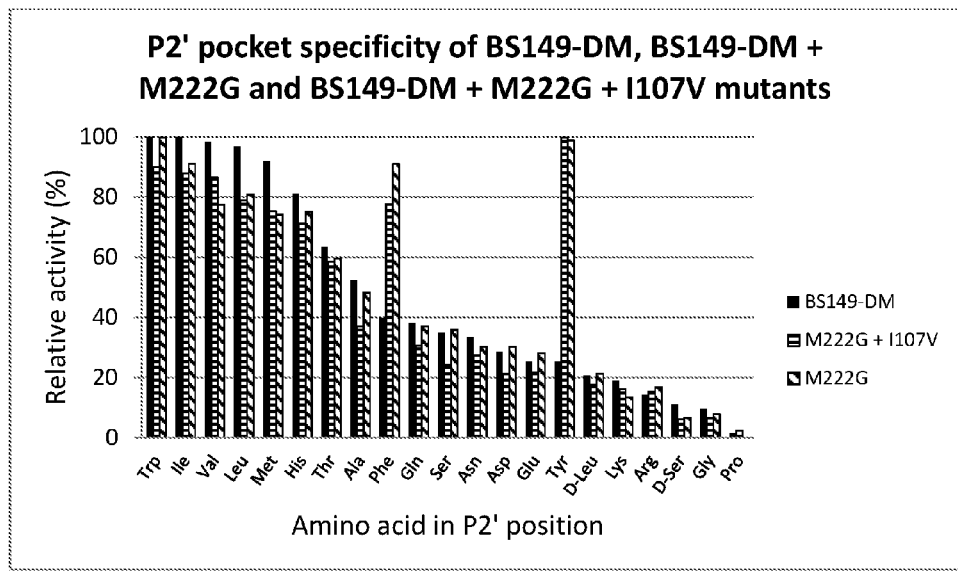
Figure 7C:
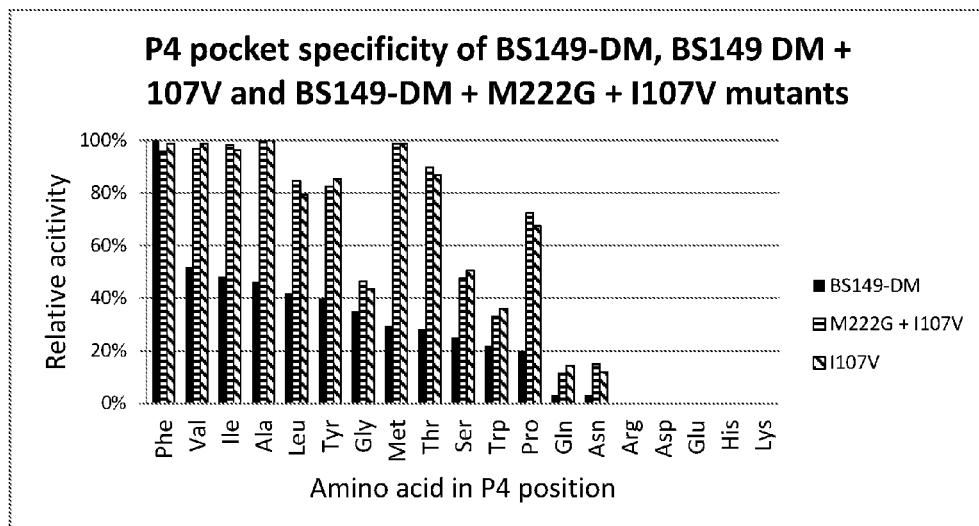

Conclusions: as evident from FIGS. 5A-L, the P1' and P2' substrate scopes of the BS149-DM+M222P mutants with a P1' mutation on position L217 clearly differs from that of BS149-DM+M222P which may be advantageous for various particular peptide sequences. Several mutants show a much broader P1' and P2' substrate scope than BS149-DM. This is in particular the case with mutations L217G and L217H. Several mutants show a drastically improved activity for certain particular substrates. For instance improved activity for Phe in the P1' pocket for mutations BS149-DM+M222P+L217N, E, G, Y, F or II. The mutant BS149-DM+M222P+L217H also shows a much increased activity for Asn in the P1' pocket. The mutants BS149-DM+M222P+L217E and A have an improved activity for Leu, Ile and Val in the P1' pocket. The mutants BS149-DM+M222P+L217T and S have an improved activity for Asp in the P1' pocket.

Example 6: Mapping the P1' Pocket Substrate Specificity of Different BS149-DM+M222G+L217 Mutants To determine the P1' pocket substrate specificity of the different mutants, the same reactions and analyses were performed as described in Example 4. The P1' pocket substrate specificities of different BS149-DM+M222G+L217 mutants are shown in FIGS. 6A-F.

Conclusions: as evident from FIGS. 6A-F, the P1' substrate scopes of the BS149-DM+M222G mutants with a P1' mutation on position L217 clearly differs from that of BS149-DM+M222G which may be advantageous for various particular peptide sequences. Several mutants show a much broader P1' substrate scope than BS149-DM. This is in particular the case with mutations L217G and L217F. Several mutants show a drastically improved activity for certain particular substrates. For instance improved activity for Phe in the P1' pocket for mutations BS149-DM+M222G+L217N, E, G, Y, F, I or II. The mutant BS149-DM+M222G+L217F also shows a much increased activity for Asn in the P1' pocket. The mutants BS149-DM+M222G+L217F, G, A and Y have an improved activity for Leu, Ile and Val in the P1' pocket. The mutants BS149-DM+M222G+L217R, T and S have an improved activity for Asp in the P1' pocket.

Example 7: Mapping the P1', P2' and P4 Pocket Substrate Specificity of BS149-DM+M222G+I107V Mutant To determine the P1' and P2' pocket substrate specificity of BS149-DM+M222G+I107V, the same reactions and analyses were performed as described in Example 4. The P1' and P2' pocket substrate specificities of the BS149-DM+M222G+I107V mutant are shown in FIGS. 67A and B, respectively. To determine the P4 pocket substrate specificity of BS149-DM+M222G+I107V, the same reactions and analyses were performed as described in Example 3. The P4 pocket substrate specificity of the BS149-DM+M222G+I107V mutant is shown in FIG. 7C.

Conclusions: as evident from FIGS. 7A-C, the P1' and P2' substrate scope as well as the P4 substrate scope of the BS149-DM+M222G+I107V mutant are broader as compared to BS149-DM. Clearly, the advantageous mutations for the P1' and P2' pockets (i.e. M222G) and for the P4 pocket (i.e. I107V) can be successfully combined since the substrate broadness is comparable to the BS149-DM+M222G mutant but the S/H ratio is significantly higher (see Example 1).

Example 8: Enzymatic Coupling Reactions Using Different N-acetyl Protected Oligopeptide C-Terminal Cam-ester Acyl Donors Peptide ligation reactions were performed at 25° C. in 100 mM Tricine buffer (pH 8.0), containing 15 μM BS149-DM, 10 mM peptide C-terminal Cam-ester (Ac-Asp-Leu-Ser-Lys-Gln-OCam.TFA, Ac-Thr-Ser-Asp-Leu-Ser-Lys-Gln-OCam.TFA, Ac-Thr-Phe-Thr-Ser-Asp-Leu-Ser-Lys-Gln-OCam.TFA or Ac-Glu-Gly-Thr-Phe-Thr-Ser-Asp-Leu-Ser-Lys-Gln-OCam.TFA) and 15 mM dipeptide C-terminal amide (H-Ala-Phe-NH$_2$). After 180 min the reaction mixtures were analyzed by LC-MS. The product, hydrolysed C-terminal Cam-ester and remaining Cam-ester peaks were integrated. The S/H ratio of the different reactions is defined as the amount of product divided by the amount of hydrolysed C-terminal Cam-ester, within the specified reaction time.

TABLE 1

Coupling of different acyl donors with H-Ala-Phe-NH2

| Peptide C-terminal Cam-ester | Peptide amine nucleophile | S/H ratio |
|---|---|---|
| Ac-Asp-Leu-Ser-Lys-Gln-Ocam | H-Ala-Phe-NH$_2$ | 12 |
| Ac-Thr-Ser-Asp-Leu-Ser-Lys-Gln-Ocam | H-Ala-Phe-NH$_2$ | 59 |
| Ac-Thr-Phe-Thr-Ser-Asp-Leu-Ser-Lys-Gln-OCam | H-Ala-Phe-NH$_2$ | 41 |
| Ac-Glu-Gly-Thr-Phe-Thr-Ser-Asp-Leu-Ser-Lys-Gln-OCam | H-Ala-Phe-NH$_2$ | 80 |

Conclusions: different lengths of oligopeptide acyl donors can be used. The S/H ratio increases with the length of the oligopeptide acyl donor.

Example 9: Enzymatic Coupling Reactions Using Different Oligopeptide C-Terminal Amide Nucleophiles Peptide ligation reactions were performed at 25° C. in 100 mM Tricine buffer (pH 8.0), containing 15 μM BS149-DM, 1 mM pentapeptide C-terminal Cam-ester (Ac-Phe-Ile-Glu-Trp-Leu-OCam) and 3 mM peptide amine nucleophile (H-Ala-Phe-NH$_2$, H-Ala-Phe-Ala-NH$_2$ or H-Ala-Phe-Ala-Tyr-NH$_2$). After 60 min the reaction mixtures were analyzed by LC-MS. The product, hydrolysed pentapeptide C-terminal Cam-ester and remaining pentapeptide C-terminal Cam-ester peaks were integrated. The S/H ratio of the different reactions is defined as the amount of product divided by the amount of hydrolysed pentapeptide C-terminal Cam-ester, within the specified reaction time.

TABLE 2

Coupling of different oligopeptide nucleophiles with Ac-Phe-Ile-Glu-Trp-Leu-OCam

| Peptide C-terminal Cam-ester | Peptide amine nucleophile | S/H ratio |
|---|---|---|
| Ac-Phe-Ile-Glu-Trp-Leu-OCam | H-Ala-Phe-NH$_2$ | 1.5 |
| Ac-Phe-Ile-Glu-Trp-Leu-OCam | H-Ala-Phe-Ala-NH$_2$ | 1.7 |
| Ac-Phe-Ile-Glu-Trp-Leu-OCam | H-Ala-Phe-Ala-TyrNH$_2$ | 1.9 |

Conclusions: different lengths of oligopeptide nucleophiles can be used. The S/H ratio increases with the length of the oligopeptide nucleophile.

Example 10: Effect of the pH on the S/H Ratio of BS149-DM+M222G Mutant

Figure 8:
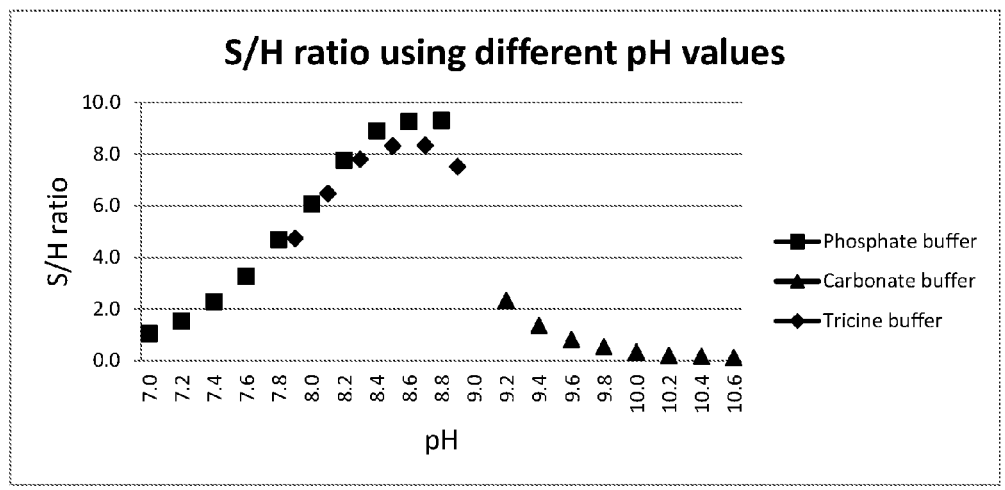

To examine the effect of pH on the S/H ratio of the BS149-DM+M222G mutant, the following standard reaction was performed. 800 μL of phosphate buffer (1M, pH 7.0-8.8), or tricine buffer (1M, pH 7.9-8.9) or carbonate buffer (1M, pH 9.2-10.6) was added to a mixture of 100 μL tripeptide C-terminal amide stock solution (0.01 mmol H-Ala-Leu-Arg-NH$_2$.2TFA in 300 μL water) and 100 μL pentapeptide C-terminal Cam-ester stock solution (0.01 mmol Ac-Asp-Phe-Ser-Lys-Leu-OCam.TFA in 1.2 mL water). To this mixture 5.5 μg enzyme was added and the reaction mixture was shaken (150 rpm) at room temperature. After 30 min a 550 μL aliquot of the reaction mixture was withdrawn and quenched with 50 μL MSA and analyzed by LC-MS. The product, hydrolysed pentapeptide C-terminal Cam-ester and remaining pentapeptide C-terminal Cam-ester peaks were integrated and the S/H ratio is defined as the amount of product divided by the amount of hydrolysed pentapeptide C-terminal Cam-ester, within the specified reaction time, see FIG. 8.

Conclusions: the S/H ratio of BS149-DM+M222G is dependent on the pH and there is a clear optimum between pH 8 and pH 9, but lower or higher pH can also be used depending on the solubility and stability properties of the oligopeptides.

Figure 9A:
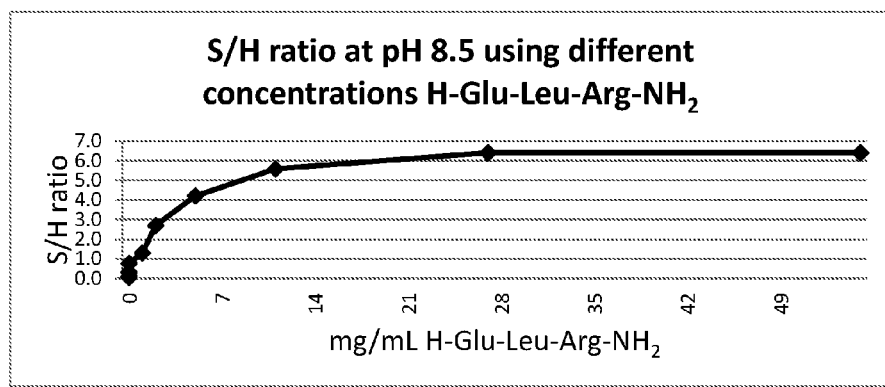
Figure 9B:
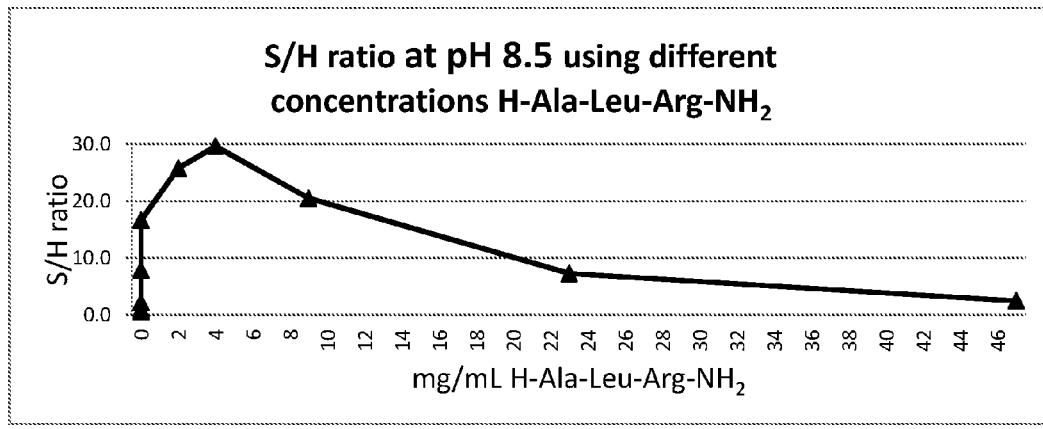

Example 11: Effect of the Concentration of Acyl Donors and Nucleophiles on the S/H Ratio of BS149-DM+M222G To examine the effect of substrate concentration on the S/H ratio of mutant BS149-DM+M222G, the following reactions were performed. A stock solution of tripeptide C-terminal amide (12.9 mg H-Glu-Leu-Arg-NH$_2$.2TFA or 11.7 mg H-Ala-Leu-Arg-NH$_2$.2TFA) and C-terminal pentapeptide Cam-ester (4.2 mg Ac-Asp-Phe-Ser-Lys-Leu-OCam.TFA) in 150 μL water was prepared. The mixtures were brought to neutral pH with 5.1 μL NaOH (32 wt % in water). To prepare reaction mixtures with different concentration of substrates, 10 μL of one of the above stock solutions was diluted with 10, 20, 50, 100, 200, 500, 1000, 2000, 5000 and 10000 μL phosphate buffer (1M, pH 8.5). To these reaction mixtures 11 μg of BS149-DM+M222G was added and the reaction mixture was shaken (150 rpm) at room temperature. After 30 min a 550 μL aliquot of the reaction mixture was withdrawn and quenched with 50 μL MSA and analyzed by LC-MS. The product, hydrolysed pentapeptide C-terminal Cam-ester and remaining pentapeptide C-terminal Cam-ester peaks were integrated and the S/H ratio is defined as the amount of product divided by the amount of hydrolysed pentapeptide C-terminal Cam-ester, within the specified reaction time, see FIGS. 9A and B.

Conclusions: the S/H ratio is dependent on the substrate concentrations. There is an optimal substrate concentration for each individual substrate depending on the affinity of the nucleophile for the enzyme and on the solubility and stability properties of the oligopeptides.

Example 12: Effect of Dosing of the Acyl Donor on the S/H Ratio Using BS149-DM+M222G To examine the effect of dosing of the acyl donor on the S/H ratio of mutant BS149-DM+M222G, the following two reactions were performed. In two-fold, 800 μL of phosphate buffer (100 mM, pH 8.0) was added to 100 μL tripeptide C-terminal amide stock solution (0.01 mmol H-Ala-Leu-Arg-NH$_2$.2TFA in 300 μL water) and 5.5 μg BS149-DM+M222G. To one of these mixtures, 100 μL pentapeptide C-terminal Cam-ester stock solution (0.01 mmol Ac-Asp-Phe-Ser-Lys-Leu-OCam.TFA in 1.2 mL water) was added and the reaction mixture was shaken (150 rpm) at room temperature. To the other mixture 100 μL pentapeptide C-terminal Cam-ester stock solution (0.01 mmol Ac-Asp-Phe-Ser-Lys-Leu-OCam.TFA in 1.2 mL water) was dosed in portions of 3.5 μL every minute while shaking the reaction mixture (150 rpm) at room temperature. After 30 min a 550 μL aliquot of both reaction mixtures was withdrawn and quenched with 50 μL MSA and analyzed by LC-MS. For both reactions the conversion of the pentapeptide C-terminal Cam-ester starting material was 100%. The product and hydrolysed pentapeptide C-terminal Cam-ester peaks were integrated and the S/H ratio is defined as the amount of product divided by the amount of hydrolysed pentapeptide C-terminal Cam-ester, within the specified reaction time. The S/H ratio for the reaction where all acyl donor was added at t=0 was 2.45 and the S/H ratio for the reaction where the acyl donor was dosed every minute was 2.73.

Conclusions: by dosing the oligopeptide C-terminal Cam-ester in time the S/H ratio can be improved.

Example 13: Cyclization of Oligopeptide C-Terminal Cam-Esters Using Different Enzymes The following experiments were performed to determine the S/H ratio of Subtiligase, BS149-DM and BS149-DM+M222G for the cyclization of an oligopeptide C-terminal Cam-ester.

Figure 10:
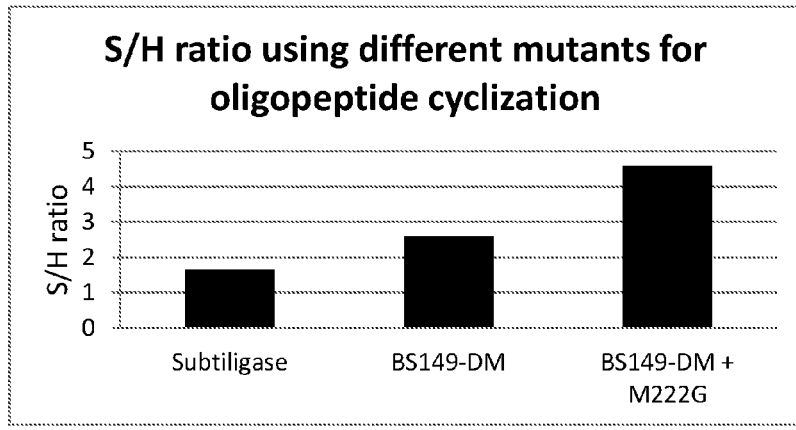

800 μL of phosphate buffer (100 mM, pH 8.0) was added to a 100 μL stock solution of an oligopeptide C-terminal Cam-ester with an N-terminal free amine (0.01 mmol H-Ala-Cys-Lys-Asn-Gly-Gln-Thr-Asn-Cys-Tyr-Gln-Ser-Tyr-OCam.2TFA in 1 mL water) containing 5 mg/mL dithiotreitol. To this mixture 5.5 μg enzyme was added and the reaction mixtures were shaken (150 rpm) at room temperature. After 30 min a 550 μL aliquot of the reaction mixtures was withdrawn and quenched with 500 μL MSA/water (1/99, v/v) and analyzed by LC-MS. The product, hydrolysed C-terminal Cam-esterand remaining Cam-ester starting material peaks were integrated and the S/H ratio of the different enzymes is defined as the amount of product divided by the amount of hydrolysed C-terminal Cam-ester, within the specified reaction time, see FIG. 10.

Conclusions: evidently, also for peptide cyclisation, BS149-DM has an improved S/H ratio as compared to Subtiligase. The BS-149-DM+M222G mutant has an even higher S/H ratio.

Example 14: Effect of the pH on the S/H Ratio During Cyclisation of an Oligopeptide C-Terminal Cam-Ester Using BS149-DM+M222G To determine the effect of the pH on the S/H ratio of BS149-DM+M222G during the cyclisation of an oligopeptide C-terminal Cam-ester, the following standard reactions were performed. 800 μL of phosphate buffer (1M, pH 5, 6, 7, 8 and 9) was added to 100 μL stock solution of a tridecapeptide C-terminal Cam-ester with an N-terminal free amine (0.01 mmol H-Ala-Cys-Lys-Asn-Gly-Gln-Thr-Asn-Cys-Tyr-Gln-Ser-Tyr-OCam.2TFA in 1 mL water) containing 5 mg/mL dithiotreitol. To this mixture 5.5 μg BS149-

Figure 11:
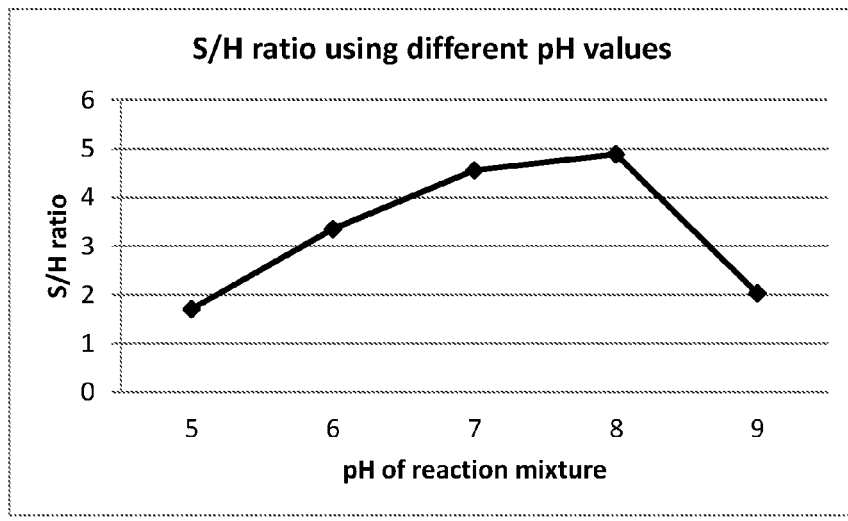

DM+M222G was added and the reaction mixture was shaken (150 rpm) at room temperature. After 30 min a 550 µL aliquot of the reaction mixture was withdrawn and quenched with 50 µL MSA and analyzed by LC-MS. The product, hydrolysed C-terminal Cam-ester and remaining C-terminal Cam-ester starting material peaks were integrated and the S/H ratio is defined as the amount of product divided by the amount of hydrolysed C-terminal Cam-ester, within the specified reaction time, see FIG. 11.

Conclusions: the S/H ratio of BS149-DM+M222G used for enzymatic oligopeptide cyclisation is dependent on the pH, albeit to a lesser extent than for enzymatic oligopeptide fragment condensation.

Example 15: Fragment Condensation with Oligopeptides Over 10 Amino Acids Long To examine whether enzymatic fragment condensation with longer oligopeptides in aqueous solution is feasible, the following standard reaction was performed. 800 µL of phosphate buffer (1M, pH 8.0) was added to a mixture of 100 µL decapeptide C-terminal amide stock solution (0.01 mmol H-Ala-Leu-Met-Lys-Tyr-Asn-Ser-Thr-Glu-Val-NH$_2$.2TFA in 300 µL water) and 200 µL tridecapeptide C-terminal Cam-ester stock solution (0.01 mmol Fmoc-His-Ala-Glu-Gly-Thr-Phe-Thr-Ser-Asp-Leu-Ser-Lys-Gln-OCam.2TFA in 1.2 mL water+1 mL DMF). To this mixture 5.5 µg BS149-DM+M222G was added and the reaction mixture was shaken (150 rpm) at room temperature. After 30 min a 550 µL aliquot of the reaction mixture was withdrawn and quenched with 50 µL MSA and analyzed by LC-MS. The product, hydrolysed C-terminal Cam-ester and remaining C-terminal Cam-ester peaks were integrated. The amount of product (Fmoc-His-Ala-Glu-Gly-Thr-Phe-Thr-Ser-Asp-Leu-Ser-Lys-Gln-Ala-Leu-Met-Lys-Tyr-Asn-Ser-Thr-Glu-Val-NH$_2$), within the specified reaction time, was 68 area %.

Conclusion: Fragment condensations with longer peptides are well-feasible.

Example 16: Fragment Condensation Using Oligopeptides without N- or C-Terminal Protecting Group To examine whether enzymatic fragment condensation without N- or C-terminal protecting group is feasible without significant side-product formation, the following standard reaction was performed. 800 µL of phosphate buffer (1M, pH 8.0) was added to a mixture of 100 µL tripeptide C-terminal carboxylic acid stock solution (0.01 mmol H-Ala-Leu-Arg-OH.2TFA in 300 µL water) and 100 µL N-terminal free amine pentapeptide C-terminal Cam-ester stock solution (0.01 mmol H-His-Ala-Glu-Gly-Thr-OCam.TFA in 1.2 mL water). To this mixture 5.5 µg of BS149-DM+M222G was added and the reaction mixture was shaken (150 rpm) at room temperature. After 30 min a 550 µL aliquot of the reaction mixture was withdrawn and quenched with 50 µL MSA and analyzed by LC-MS. The product, hydrolysed pentapeptide C-terminal Cam-ester and remaining pentapeptide C-terminal Cam-ester peaks were integrated. The amount of product (H-His-Ala-Glu-Gly-Thr-Ala-Leu-Arg-OH), within the specified reaction time, was 74 area %. No side-products were observed indicating that no side-reactions had occurred at the C-terminal carboxylic acid function of H-Ala-Leu-Arg-OH.2TFA nor at the N-terminal amine function of H-His-Ala-Glu-Gly-Thr-OCam.

Conclusion: some oligopeptide sequences can be successfully enzymatically ligated without using N- or C-terminal protecting groups.

Example 17: Fragment Condensations Using Oligopeptide C-Terminal Cam-Xxx-NH$_2$ or Cam-Xxx-OH Esters To examine whether enzymatic fragment condensations with Cam-Xxx-NH$_2$ or Cam-Xxx-OH esters are feasible, the following standard reactions were performed. 800 µL of phosphate buffer (1M, pH 8.0) was added to a mixture of 100 µL tripeptide C-terminal amide stock solution (0.01 mmol H-Ala-Leu-Arg-NH$_2$.2TFA in 300 µL water) and 100 µL pentapeptide C-terminal Cam-ester stock solution (0.01 mmol Ac-Asp-Phe-Ser-Lys-Leu-OCam-Leu-OH.TFA, Ac-Asp-Phe-Ser-Lys-Leu-OCam-Leu-NH$_2$.TFA, Ac-Asp-Phe-Ser-Lys-Leu-OCam-Lys-NH$_2$.2TFA or Ac-Asp-Phe-Ser-Lys-Leu-OCam-Glu-NH2.TFA in 1.2 mL water). To each of these 4 mixtures 5.5 µg of BS149-DM+M222G was added and the reaction mixtures were shaken (150 rpm) at room temperature. After 30 min a 550 µL aliquot of the reaction mixtures was withdrawn and quenched with 50 µL MSA and analyzed by LC-MS. The product, hydrolysed pentapeptide C-terminal Cam-ester and remaining tetrapeptide C-terminal Cam-ester peaks were integrated. The amount of product (Ac-Asp-Phe-Ser-Lys-Leu-Ala-Leu-Arg-NH$_2$), within the specified reaction time, was 86 area % for Ac-Asp-Phe-Ser-Lys-Leu-OCam-Leu-OH, 83 area % for Ac-Asp-Phe-Ser-Lys-Leu-OCam-Leu-NH$_2$, 78 area % for Ac-Asp-Phe-Ser-Lys-Leu-OCam-Lys-NH$_2$ and 83 area % for Ac-Asp-Phe-Ser-Lys-Leu-OCam-Glu-NH$_2$.

Conclusions: this example shows that Cam-Xxx-NH$_2$ and Cam-Xxx-OH esters can be used successfully for enzymatic oligopeptide fragment condensation.

Example 18: Fragment Condensation Using a C-Terminal Oligopeptide Thioester and BS149DM+I107V+M222G To examine whether enzymatic oligopeptide fragment condensations using C-terminal thioesters are feasible, the following standard reaction was performed. 1 mL of Tricine buffer (100 mM, pH 7.5), containing 2.5 mM pentapeptide C-terminal thio-ester (Suc-Ala-Ala-Pro-Phe-SBzl), 25 mM dipeptide C-terminal amide (H-Gly-Phe-NH$_2$), and 5 µg BS149-DM+L107V+M222G, was shaken (150 rpm) at 25° C. After 30 min a 550 µL aliquot of the reaction mixture was withdrawn and quenched with 50 µL MSA and analyzed by LC-MS. The product, hydrolysed tetrapeptide C-terminal thio-ester and remaining tetrapeptide C-terminal thio-ester peaks were integrated. The amount of product (Suc-Ala-Ala-Pro-Phe-Gly-Phe-NH$_2$), within the specified reaction time, was 85 area %.

Conclusions: this example shows that oligopeptide C-terminal thioesters can be used successfully for enzymatic oligopeptide fragment condensation.

Example 19: Fragment Condensation Using a C-Terminal Oligopeptide Alkyl Ester and BS149-DM+I107V+M222G To examine whether enzymatic oligopeptide fragment condensations using C-terminal alkyl esters are feasible the following standard reaction was performed. 1 mL of Tricine buffer (100 mM, pH 7.5), containing 2.5 mM pentapeptide C-terminal alkyl ester (Ac-Asp-Phe-Ser-Lys-Leu-OTFE (TFE=2,2,2-trifluoroethyl)), 25 mM tripeptide C-terminal amide (H-Ala-Leu-Arg-NH$_2$), and 5 µg BS149-DM+I107V+M222G, was shaken (150 rpm) at 25° C. After 30 min a 550 µL aliquot of the reaction mixture was withdrawn and quenched with 50 µL. MSA and analyzed by LC-MS. The product, hydrolysed pentapeptide C-terminal alkyl-ester and remaining pentapeptide alkyl-ester peaks were integrated. The amount of product (Ac-Asp-Phe-Ser-Lys-Leu-Ala-Leu-Arg-NH$_2$), within the specified reaction time, was 55 area %.

Conclusions: this example shows that oligopeptide C-terminal alkyl esters can be used successfully for enzymatic oligopeptide fragment condensation.

Example 20: Enzymatic Oligopeptide Fragment Condensation Using Partial Side-Chain Protection To demonstrate that partial P1' side-chain protection can be beneficial, the following reaction was performed. 800 µL of phosphate buffer (100 mM, pH 8.0) was added to a mixture of 100 µL tripeptide C-terminal amide stock solution (0.01 mmol H-Asp-Leu-Arg-NH$_2$.2TFA or 0.01 mmol H-Asp(OcHex)-Leu-Arg-NH$_2$.2TFA in 300 µL water) and 100 µL pentapeptide C-terminal Cam-ester stock solution (0.01 mmol Ac-Asp-Phe-Ser-Lys-Leu-OCam.TFA in 1200 µL water). To this mixture 5.5 µg BS149-DM+M222G was added and the reaction mixture was shaken (150 rpm) at room temperature. After 30 min a 500 µL aliquot of the reaction mixture was withdrawn and quenched with 500 µL MSA/water (1/99, v/v) and analyzed by LC-MS. The product, hydrolysed pentapeptide C-terminal Cam-ester and remaining peptapeptide Cam-ester peaks were integrated. The amount of product using the unprotected substrate (H-Asp-Leu-Arg-NH$_2$), within the specified reaction time, was 18 area %, the amount of product using the partially side-chain protected substrate (H-Asp(OcHex)-Leu-Arg-NH$_2$), within the specified reaction time, was 73 area %.

To demonstrate that partial P2' side-chain protection can be beneficial, the following reaction was performed. 800 µL of phosphate buffer (100 mM, pH 8.0) was added to a mixture of 100 µL tripeptide C-terminal amide stock solution (0.01 mmol H-Asp-Glu(OBn)-Arg-NH$_2$.2TFA or 0.01 mmol H-Asp-Glu-Arg-NH$_2$.2TFA in 300 µL water) and 100 µL pentapeptide C-terminal Cam-ester stock solution (0.01 mmol Ac-Asp-Phe-Ser-Lys-Leu-OCam.TFA in 1200 µL water). To this mixture 5.5 µg BS149-DM+M222G was added and the reaction mixture was shaken (150 rpm) at room temperature. After 30 min a 500 µL aliquot of the reaction mixture was withdrawn and quenched with 500 µL MSA/water (1/99, v/v) and analyzed by LC-MS. The product, hydrolysed pentapeptide C-terminal Cam-ester and remaining peptapeptide Cam-ester peaks were integrated. The amount of product using the unprotected substrate (H-Asp-Glu-Arg-NH$_2$), within the specified reaction time, was 15 area %, the amount of product using the partially side-chain protected substrate (H-Asp-Glu(OBn)-Arg-NH$_2$), within the specified reaction time, was 58 area %.

To demonstrate that partial P1 side-chain protection can be beneficial, the following reaction was performed. 800 µL of phosphate buffer (100 mM, pH 8.0) was added to a mixture of 100 µL tripeptide C-terminal amide stock solution (0.01 mmol H-Asp-Leu-Arg-NH$_2$.2TFA) and 100 µL pentapeptide C-terminal Cam-ester stock solution (0.01 mmol Ac-Asp-Phe-Ser-Lys-Leu-OCam.TFA or 0.01 mmol Ac-Asp-Phe-Ser-Leu-Lys(Alloc)-OCam in 1200 µL water). To this mixture 5.5 µg BS149-DM+M222G was added and the reaction mixture was shaken (150 rpm) at room temperature. After 30 min a 500 µL aliquot of the reaction mixture was withdrawn and quenched with 500 µL MSA/water (1/99, v/v) and analyzed by LC-MS. The product, hydrolysed pentapeptide C-terminal Cam-ester and remaining peptapeptide Cam-ester peaks were integrated. The amount of product using the unprotected substrate (Ac-Asp-Phe-Ser-Leu-Lys-OCam.TFA), within the specified reaction time, was 5 area %, the amount of product using the partially side-chain protected substrate (Ac-Asp-Phe-Ser-Leu-Lys (Alloc)-OCam) was 84 area %.

To demonstrate that partial P4 side-chain protection can be beneficial, the following reaction was performed. 800 µL of phosphate buffer (100 mM, pH 8.0) was added to a mixture of 100 µL tripeptide C-terminal amide stock solution (0.01 mmol H-Ala-Leu-Arg-NH$_2$.2TFA) and 100 µL tetrapeptide C-terminal Cam-ester stock solution (0.01 mmol Ac-Asp-Ser-Lys-Leu-OCam.TFA or 0.01 mmol Ac-Asp(OBn)-Ser-Lys-Leu-OCam.TFA in 1200 µL water). To this mixture 5.5 µg BS149-DM+M222G was added and the reaction mixture was shaken (150 rpm) at room temperature. After 30 min a 500 µL aliquot of the reaction mixture was withdrawn and quenched with 500 µL MSA/water (1/99, v/v) and analyzed by LC-MS. The product, hydrolysed tetrapeptide C-terminal Cam-ester and remaining tetrapeptide Cam-ester peaks were integrated. The amount of product using the unprotected substrate (mmol Ac-Asp-Ser-Lys-Leu-OCam.TFA), within the specified reaction time, was 32 area %, the amount of product using the partially side-chain protected substrate (Ac-Asp(OBn)-Ser-Lys-Leu-OCam.TFA) was 78 area %.

Conclusions: this example shows that partial side-chain protection can improve the yield and/or reaction rate of enzymatic oligopeptide fragment condensations

Example 21: Thermostability of BS149-DM

The fluorescence-based thermal stability assay was used to determine the apparent melting temperature of BS149-DM and subtiligase. A sample of 20 µL of protein solution in buffer (20 mM Tricine buffer, pH 7.5) and metal ions (10 mM) or EDTA (10 mM) was mixed with 5 µL of 100 times diluted Sypro Orange (Molecular Probes, Life Technologies, USA) dye in a thin wall 96-well PCR plate. The plate was sealed with Optical-Quality Sealing Tape and heated in an CFX 96 Real Time PCR System (BioRad, Hercules, Calif., USA) from 20 to 99° C. at a heating rate of 1.75° C./min. Fluorescence changes were monitored with a charge-coupled device (CCD) camera. The wavelengths for excitation and emission were 490 and 575 nm, respectively. The thermostability of the purified BS149-DM was determined as described above. The thermostability was also determined after the addition of different metal ions and chelating agents, see Table 3 below. An apparent transition temperature (Tm) of 66° C. was observed, indicating that the enzyme BS149-DM well preserves the thermostability from BS149. In contrast, the Tm value of Subtiligase was determined to be 59° C.

TABLE 3

Effect of metal ions (10 mM) and the chelating agent EDTA (10 mM) on the thermostability of BS149-DM.

| | $T_m$ (° C.) |
|---|---|
| Control | 66 |
| $Ca^{2+}$ | 65.5 |

TABLE 3-continued

Effect of metal ions (10 mM) and the chelating agent EDTA (10 mM) on the thermostability of BS149-DM.

| | $T_m$ (° C.) |
|---|---|
| $Mg^{2+}$ | 65 |
| $Mn^{2+}$ | 64.5 |
| $Ni^{2+}$ | 62 |
| EDTA | 66.5 |

Conclusions: clearly, BS149-DM has an improved thermostability as compared to Subtiligase. The enzyme BS149-DM is also resistant to metal ions and chelating agents, since in their presence the Tm value remains virtually unaffected.

Example 22: Effect of Organic Solvents and Different Additives on BS149-DM Activity Peptide ligation reactions were performed at 25° C. in 100 mM Tricine buffer (pH 8.0), containing 15 μM BS149-DM, 1 mM pentapeptide C-terminal Cam-ester (Ac-Phe-Ile-Glu-Trp-Leu-OCam) and 3 mM dipeptide C-terminal amide (H-Ala-Phe-NH$_2$). Different amounts of metal ions (10 mM), EDTA (10 mM) or organic solvent were added and after 60 min the reaction mixtures were analyzed by LC-MS. The product, hydrolysed pentapeptide C-terminal Cam-ester and remaining peptapeptide Cam-ester peaks were integrated. The activity of BS149-DM is defined as the total of the amount of product and the amount of hydrolysed pentapeptide C-terminal Cam-ester divided by the total of the amount of product, hydrolysed pentapeptide C-terminal Cam-ester and remaining Cam-ester, within the specified reaction time. The most reaction with the highest activity was set to 100%, see Tables 4-8.

TABLE 4

Effect of metal ions (10 mM) and the chelating agent EDTA (10 mM) on the activity of BS149-DM.

| | Activity (%) |
|---|---|
| No additive | 87 |
| $Ca^{2+}$ | 67 |
| $Mg^{2+}$ | 87 |
| $Mn^{2+}$ | 100 |
| $Ni^{2+}$ | 73 |
| EDTA | 87 |

TABLE 5

Effect of THF on the activity of BS149-DM.

| | Activity (%) |
|---|---|
| No additive | 100 |
| 10 vol % THF | 60 |
| 20 vol % THF | 30 |
| 30 vol % THF | 10 |
| 40 vol % THF | 4 |

TABLE 6

Effect of DMF on the activity of BS149-DM.

| | Activity (%) |
|---|---|
| No additive | 100 |
| 10 vol % DMF | 64 |

TABLE 6-continued

Effect of DMF on the activity of BS149-DM.

| | Activity (%) |
|---|---|
| 20 vol % DMF | 36 |
| 30 vol % DMF | 32 |
| 40 vol % DMF | 18 |
| 50 vol % DMF | 14 |

TABLE 7

Effect of DMSO on the activity of BS149-DM.

| | Activity (%) |
|---|---|
| No additive | 100 |
| 10 vol % DMSO | 87 |
| 20 vol % DMSO | 73 |
| 30 vol % DMSO | 76 |
| 40 vol % DMSO | 62 |
| 50 vol % DMSO | 35 |

TABLE 8

Effect of GndCl on the activity of BS149-DM.

| | Activity (%) |
|---|---|
| No additive | 92 |
| 0.66M GndCl | 100 |
| 1.32M GndCl | 90 |
| 2.00M GndCl | 81 |
| 2.64M GndCl | 75 |
| 3.33M GndCl | 67 |
| 4.00M GndCl | 43 |

Example 23: Enzymatic Oligopeptide Fragment Coupling Using BS149-DM with and without His-Tag To test the activity and S/H ratio of the different enzymes, the following two standard reactions were performed. 800 μL of phosphate buffer (100 mM, pH 8.0) was added to a mixture of 100 μL pentripeptide C-terminal amide stock solution (0.01 mmol H-Ala-Leu-Arg-NH$_2$.2TFA in 300 μL water) and 100 μL pentapeptide C-terminal Cam-ester stock solution (0.01 mmol Ac-Asp-Phe-Ser-Lys-Leu-OCam.TFA in 1200 μL water). To this mixture was added 5.5 μg BS149-DM either with or without His-tag was added and the reaction mixtures were shaken (150 rpm) at room temperature. After 30 min a 500 μL aliquot of the reaction mixtures was withdrawn and quenched with 500 μL MSA/water (1/99, v/v) and analyzed by LC-MS. The product, hydrolysed pentapeptide C-terminal Cam-ester and remaining pentapeptide C-terminal Cam-ester peaks were integrated.

The S/H ratio of BS149-DM with His-tag respectively without His-tag is defined as the amount of product (synthesized oligopeptide) divided by the amount of hydrolysed pentapeptide C-terminal Cam-ester, within the specified time. The S/H ratio for BS149 with His-tag was 1.91 and for BS149 without His-tag 1.98.

The activity of BS149-DM with and without His-tag is defined as the total of the amount of product and the amount of hydrolysed pentapeptide C-terminal Cam-ester divided by the total of the amount of product, hydrolysed pentapeptide C-terminal Cam-ester and remaining Cam-ester, within the specified reaction time. The activity of BS149-DM with His-tag was 97.3% and for BS149-DM without His-tag 98.6%.

Conclusions: the presence or absence of the His-tag has no significant effect on the S/H ratio and the activity.

Example 24: S/H Ratio of Enzymes Corresponding to SEQ ID NO 3 with Different Mutations To test the activity and S/H ratio of the different mutants, the following standard reaction was performed. 800 µL of phosphate buffer (100 mM, pH 8.0) was added to a mixture of 100 µL tripeptide C-terminal amide stock solution (0.01 mmol H-Ala-Leu-Arg-NH$_2$.2TFA in 300 µL water) and 100 µL pentapeptide C-terminal Cam-ester stock solution (0.01 mmol Ac-Asp-Phe-Ser-Lys-Leu-OCam.TFA in 1200 µL water). To this mixture 5.5 µg enzyme was added and the reaction mixture was shaken (150 rpm) at room temperature. After 30 min a 500 µL aliquot of the reaction mixture was withdrawn and quenched with 500 µL MSA/water (1/99, v/v) and analyzed by LC-MS. The product, hydrolysed pentapeptide C-terminal Cam-ester and remaining pentapeptide C-terminal Cam-ester peaks were integrated.

The S/H ratio of the different mutants is defined as the amount of product divided by the amount of hydrolysed pentapeptide C-terminal Cam-ester, within the specified time (see Table 9).

TABLE 9

S/H ratio of enzymes corresponding to SEQ ID NO 3 with different mutations

| Amino acid at position X225 of SEQ ID NO 3 | Additive mutations | S/H ratio |
|---|---|---|
| P (proline, as in wild-type subtilisin BPN') | | 1.97 |
| A | | 2.03 |
| G | | 1.76 |
| A | N218S | 2.40 |
| A | N218S, M50F | 2.55 |
| A | N218S, M50F, S3C-Q206C, Q2K, A73L, P5S | 2.40 |
| A | N218S, M50F, S3C-Q206C, Q2K, A73L, P5S, Y217L | 2.09 |

Conclusions: clearly, several enzymes corresponding to SEQ ID NO 3 (X=A) with the S221C mutation have a twofold increased S/H ratio compared to subtiligase (S/H subtiligase=0.9, see example 1). The S/H ratio remains unaffected with X=P, G or A.

Example 25: S/H Ratio of BS149-DM+M222P+L217H+X225 Mutants

To test the activity and S/H ratio of the different mutants, the following standard reaction was performed. 800 µL of phosphate buffer (100 mM, pH 8.0) was added to a mixture of 100 µL tripeptide C-terminal amide stock solution (0.01 mmol H-Ser-Leu-Arg-NH$_2$.2TFA in 300 µL water) and 100 µL pentapeptide C-terminal Cam-ester stock solution (0.01 mmol Ac-Asp-Phe-Ser-Lys-Leu-OCam.TFA in 1200 µL water). To this mixture 5.5 µg enzyme was added and the reaction mixture was shaken (150 rpm) at room temperature. After 30 min a 500 µL aliquot of the reaction mixture was withdrawn and quenched with 500 µL MSA/water (1/99, v/v) and analyzed by LC-MS. The product, hydrolysed pentapeptide C-terminal Cam-ester and remaining pentapeptide C-terminal Cam-ester peaks were integrated.

The S/H ratio of the different mutants is defined as the amount of product divided by the amount of hydrolysed pentapeptide C-terminal Cam-ester, within the specified time (see Table 10).

TABLE 10

S/H ratio of BS149-DM + M222P + L217H + X225 mutants

| Mutant | S/H ratio |
|---|---|
| BS149-DM + M222P + L217H + X225N | 7.33 |
| BS149-DM + M222P + L217H + X225D | 6.69 |
| BS149-DM + M222P + L217H + X225S | 6.07 |
| BS149-DM + M222P + L217H + X225C | 5.25 |
| BS149-DM + M222P + L217H + X225G | 4.63 |
| BS149-DM + M222P + L217H + X225A | 4.47 |
| BS149-DM + M222P + L217H + X225T | 4.28 |
| BS149-DM + M222P + L217H + X225V | 4.26 |
| BS149-DM + M222P + L217H + X225I | 4.00 |
| BS149-DM + M222P + L217H + X225L | 3.55 |
| BS149-DM + M222P + L217H + X225H | 1.84 |
| BS149-DM + M222P + L217H + X225Q | 1.45 |
| BS149-DM + M222P + L217H + X225F | 0.71 |
| BS149-DM + M222P + L217H + X225E | 0.36 |
| BS149-DM + M222P + L217H + X225P | 0.17 |
| BS149-DM + M222P + L217H + X225K | 0.07 |
| BS149-DM + M222P + L217H + X225Y | 0.03 |
| BS149-DM + M222P + L217H + X225M | 0.03 |
| BS149-DM + M222P + L217H + X225R | 0.02 |
| BS149-DM + M222P + L217H + X225W | 0.01 |

Conclusions: clearly, the mutations at the X225 position have a large effect on the S/H ratio. Many mutations have a superb effect such as with X=N, D, S, C, G and A. Several further enzymes have an over three fold increased S/H ratio as compared to subtiligase (S/H subtiligase=0.9, see example 1) such as with X=L, I, V and T. Also, mutations of X225 into H, Q, and—to a lesser extent—F and E showed an improvement over the wild-type enzyme with X225 being P.

Example 26: Coupling of a Pentapeptide Selectively to the N-Terminus of the A-Chain of Human Insulin 5 mg of human insulin (CAS #11061-68-0) and 2.5 mg of Ac-Asp-Phe-Ser-Lys-Leu-OCam-Leu-OH.TFA were dissolved in 200 µL DMF. Subsequently, 200 µL of phosphate buffer (1 M, pH 8.0) and 200 µL H$_2$O containing 20 µg of the BS149-DM+M222G mutant were added and the reaction mixture was shaken (150 rpm) at room temperature. After 60 min a 100 µL aliquot of the reaction mixture was withdrawn and quenched with 500 µL MSA/water (1/99, v/v) and analyzed by LC-MS, showing that 92% of the insulin starting material was converted to a single product, i.e. Ac-Asp-Phe-Ser-Lys-Leu- coupled to the N-terminus of the insulin A-chain.

Example 27: Coupling of a Pentapeptide to the N-Terminus of the A- and B-Chain of Human Insulin 5 mg of human insulin (CAS #11061-68-0) and 5 mg of Ac-Asp-Phe-Ser-Lys-Leu-OCam-Leu-OH.TFA were dissolved in 200 µL DMF. Subsequently, 200 µL of phosphate buffer (1 M, pH 8.0) and 200 µL H$_2$O containing 55 µg of BS149-DM+M222G+L217F mutant were added and the reaction mixture was shaken (150 rpm) at room temperature. After 60 min a 100 µL aliquot of the reaction mixture was withdrawn and quenched with 500 µL MSA/water (1/99, v/v) and analyzed by LC-MS, showing that the insulin starting material was completely consumed and converted to three product peaks, i.e. 1) Ac-Asp-Phe-Ser-Lys-Leu- coupled to the N-terminus of the Insulin A-chain (22 area %), 2) Ac-Asp-Phe-Ser-Lys-Leu- coupled to the N-terminus of the insulin B-chain (3 area %) and 3) Ac-Asp-Phe-Ser-Lys-Leu- coupled to the N-terminus of both the Insulin A- and B-chain (75 area %).

SEQUENCES

```
SEQ ID NO 1: wild type gene encoding for subtilisin BPN' amino acids-107 to 275
ENA|K02496|K02496.1 B. Subtilisin BPN' Bacillus amyloliquefaciens
GTGAGAGGCAAAAAAGTATGGATCAGTTTGCTGTTTGCTTTAGCGTTAATCTTTACGAT

GG

CGTTCGGCAGCACATCCTCTGCCCAGGCGGCAGGGAAATCAAACGGGGAAAAGAAATA

TAT

TGTCGGGTTTAAACAGACAATGAGCACGATGAGCGCCGCTAAGAAGAAAGATGTCATT

TCT

GAAAAAGGCGGGAAAGTGCAAAAGCAATTCAAATATGTAGACGCAGCTTCAGCTACAT

TAA

ACGAAAAAGCTGTAAAAGAATTGAAAAAAGACCCGAGCGTCGCTTACGTTGAAGAAGA

TCA

CGTAGCACATGCGTACGCGCAGTCCGTGCCTTACGGCGTATCACAAATTAAAGCCCCT

GCT

CTGCACTCTCAAGGCTACACTGGATCAAATGTTAAAGTAGCGGTTATCGACAGCGGTA

TCG

ATTCTTCTCATCCTGATTTAAAGGTAGCAGGCGGAGCCAGCATGGTTCCTTCTGAAACA

AA

TCCTTTCCAAGACAACAACTCTCACGGAACTCACGTTGCCGGCACAGTTGCGGCTCTTA

AT

AACTCAATCGGTGTATTAGGCGTTGCGCCAAGCGCATCACTTTACGCTGTAAAAGTTCT

CG

GTGCTGACGGTTCCGGCCAATACAGCTGGATCATTAACGGAATCGAGTGGGCGATCGC

AAA

CAATATGGACGTTATTAACATGAGCCTCGGCGGACCTTCTGGTTCTGCTGCTTTAAAAG

CG

GCAGTTGATAAAGCCGTTGCATCCGGCGTCGTAGTCGTTGCGGCAGCCGGTAACGAAG

GCA

CTTCCGGCAGCTCAAGCACAGTGGGCTACCCTGGTAAATACCCTTCTGTCATTGCAGTA

GG

CGCTGTTGACAGCAGCAACCAAAGAGCATCTTTCTCAAGCGTAGGACCTGAGCTTGAT

GTC

ATGGCACCTGGCGTATCTATCCAAAGCACGCTTCCTGGAAACAAATACGGGGCGTACA

ACG

GTACGTCAATGGCATCTCCGCACGTTGCCGGAGCGGCTGCTTTGATTCTTTCTAAGCAC

CC

GAACTGGACAAACACTCAAGTCCGCAGCAGTTTAGAAAACACCACTACAAAACTTGGT

GAT

TCTTTCTACTATGGAAAAGGGCTGATCAACGTACAGGCGGCAGCTCAGTAA
```

-continued

SEQ ID NO 2: wild type subtilisin BPN' (mature)
>SUBT_BACAM Subtilisin BPN' *Bacillus* amyloliquefaciens mature 1 to 275
AQSVPYGVSQIKAPALHSQGYTGSNVKVAVIDSGIDSSHPDLKVAGGASMVPSETNPFQ

DNNSHGTHVAGTVAALNNSIGVLGVAPSASLYAVKVLGADGSGQYSWIINGIEWAIANN

MDVINMSLGGPSGSAALKAAVDKAVASGVVVVAAAGNEGTSGSSSTVGYPGKYPSVIAV

GAVDSSNQRASFSSVGPELDVMAPGVSIQSTLPGNKYGAYNGTSMASPHVAGAAALILS

KHPNWTNTQVRSSLENTTTKLGDSFYYGKGLINVQAAAQ

SEQ ID NO 3: subtilisin BPN' variant with deletion of Ca$^{2+}$ binding loop
and S221C and preferably P225 mutation (denoted as P225X)
AQSVPYGVSQIKAPALHSQGYTGSNVKVAVIDSGIDSSHPDLKVAGGASMVPSETNPFQ

DNNSHGTHVAGTVAAVAPSASLYAVKVLGADGSGQYSWIINGIEWAIANNMDVINMSLG

GPSGSAALKAAVDKAVASGVVVVAAAGNEGTSGSSSTVGYPGKYPSVIAVGAVDSSNQR

ASFSSVGPELDVMAPGVSIQSTLPGNKYGAYNGTCMASXHVAGAAALILSKHPNWTNTQ

VRSSLENTTTKLGDSFYYGKGLINVQAAAQ

SEQ ID NO 4: subtilisin BPN' variant with preferred mutation positions
compared to SEQ ID NO 3
AXXVXYGVXQIKAPALHSQGYTGSNVKVAVXDSGIDSSHPDLXVAGGASXVPSETNPFQ

DNNSHGTHVAGTVXAVAPSASLYAVKVLGADGSGQYSWIINGIEWAIANNMDVINMSLG

GPSGSAALKAAVDKAVASGVVVVAAAGNXGTSGSSSTVXYPXKYPSVIAVGAVDSSNQR

AXFSSVGPELDVMAPGVSIXSTLPGXKYGAXXGTCMASXHVAGAAALILSKHPNWTNTQ

VRSSLENTXTKLGDSFYYGKGLINVXAAAQ

SEQ ID NO 5: The segment of *E. coli/B. subtilis* shuttle vector pBES:Pt1149DM His
containing the *B. subtilis*-derived subtilisin (aprE) promoter region (bp 1-197,
Takara), the BPN' signal sequence (bp 198-287), the BPN' prodomain (bp 288-518),
the mature B5149-DM, 6xHistag, stop codon. From nucleotide 1590 onwards the
sequence follows pBES from Takara.

```
  1  ACTAGTGTTC TTTTCTGTAT GAAAATAGTT ATTTCGAGTC TCTACGGAAA TAGCGAGAGA

61  TGATATACCT AAATAGAGAT AAAATCATCT CAAAAAATG GGTCTACTAA AATATTATTC

121  CATCTATTAC AATAAATTCA CAGAATAGTC TTTTAAGTAA GTCTACTCTG AACTTAAGCA

181  AAAGGAGAGG GACGCGT GTG AGA GGC AAA AAA GTA TGG ATC AGT TTG CTG TTT
     RBS        MluI   Val Arg Gly Lys Lys Val Trp Ile Ser Leu Leu Phe
                      -107    -105                -100

234  GCT TTA GCG TTA ATC TTT ACG ATG GCG TTC GGC AGC ACA TCC TCT GCC
     Ala Leu Ala Leu Ile Phe Thr Met Ala Phe Gly Ser Thr Ser Ser Ala
     -95             -90              -85             -80

282  CAG GCG GCA GGG AAA TCA AAC GGG GAA AAG AAA TAT ATT GTC GGG TTT
     Gln Ala Ala Gly Lys Ser Asn Gly Glu Lys Lys Tyr Ile Val Gly Phe
                 -75             -70              -65

330  AAA CAG ACA ATG AGC ACG ATG AGC GCC GCT AAG AAG AAA GAT GTC ATT
     Lys Gln Thr Met Ser Thr Met Ser Ala Ala Lys Lys Lys Asp Val Ile
             -60             -55              -50

378  TCT GAA AAA GGC GGG AAA GTG CAA AAG CAA TTC AAA TAT GTA GAC GCA
     Ser Glu Lys Gly Gly Lys Val Gln Lys Gln Phe Lys Tyr Val Asp Ala
             -45             -40              -35

426  GCT TCA GCT ACA TTA AAC GAA AAA GCT GTA AAA GAA TTG AAA AAA GAC
     Ala Ser Ala Thr Leu Asn Glu Lys Ala Val Lys Glu Leu Lys Lys Asp
         -30             -25              -20

474  CCG AGC GTC GCT TAC GTT GAA GAA GAT CAC GTA GCA CAC GCG ATG GCG
     Pro Ser Val Ala Tyr Val Glu Glu Asp His Val Ala His Ala Met Ala
     -15             -10              -5                1

522  AAG TGC GTG TCT TAC GGC GTA GCG CAA ATT AAA GCC CCT GCT CTG CAC
     Lys Cys Val Ser Tyr Gly Val Ala Gln Ile Lys Ala Pro Ala Leu His
                  5               10              15

570  TCT CAA GGC TAC ACT GGA TCA AAT GTT AAA GTA GCG GTT CTT GAC AGC
     Ser Gln Gly Tyr Thr Gly Ser Asn Val Lys Val Ala Val Leu Asp Ser
```

-continued

```
                        20                      25                      30
 618    GGT ATC GAT TCT TCT CAT CCT GAT TTA AAC GTA GCA GGC GGA GCC AGC
        Gly Ile Asp Ser Ser His Pro Asp Leu Asn Val Ala Gly Gly Ala Ser
                35                      40                      45

666    TTC GTT CCT TCT GAA ACA AAT CCT TTC CAA GAC AAC AAC TCT CAC GGA
        Phe Val Pro Ser Glu Thr Asn Pro Phe Gln Asp Asn Asn Ser His Gly
        50                      55                      60                      65

714    ACT CAC GTT GCC GGC ACA GTT TTG GCT GTT GCG CCA AGC GCA TCA CTT
        Thr His Val Ala Gly Thr Val Leu Ala Val Ala Pro Ser Ala Ser Leu
                        70              74* 84  85                      90

762    TAC GCT GTA AAA GTT CTC GGT GCT GAC GGT TCC GGC CAA TAC AGC TGG
        Tyr Ala Val Lys Val Leu Gly Ala Asp Gly Ser Gly Gln Tyr Ser Trp
                        95                      100                     105

810    ATC ATT AAC GGA ATC GAG TGG GCG ATC GCA AAC AAT ATG GAC GTT ATT
        Ile Ile Asn Gly Ile Glu Trp Ala Ile Ala Asn Asn Met Asp Val Ile
                        110                     115                     120

858    AAC ATG AGC CTC GGC GGA CCT TCT GGT TCT GCT GCT TTA AAA GCG GCA
        Asn Met Ser Leu Gly Gly Pro Ser Gly Ser Ala Ala Leu Lys Ala Ala
                        125                     130                     135

906    GTT GAT AAA GCC GTT GCA TCC GGC GTC GTA GTC GTT GCG GCA GCC GGT
        Val Asp Lys Ala Val Ala Ser Gly Val Val Val Ala Ala Ala Gly
                140                     145                     150

954    AAC TCT GGC ACT TCC GGC AGC TCA AGC ACA GTG AGC TAC CCT GCT AAA
        Asn Ser Gly Thr Ser Gly Ser Ser Ser Thr Val Ser Tyr Pro Ala Lys
        155                     160                     165                     170

1002    TAC CCT TCT GTC ATT GCA GTA GGC GCT GTT GAC AGC AGC AAC CAA AGA
        Tyr Pro Ser Val Ile Ala Val Gly Ala Val Asp Ser Ser Asn Gln Arg
                        175                     180                     185

1050    GCA CCG TTC TCA AGC GTA GGA CCT GAG CTT GAT GTC ATG GCA CCT GGC
        Ala Pro Phe Ser Ser Val Gly Pro Glu Leu Asp Val Met Ala Pro Gly
                        190                     195                     200

1098    GTA TCT ATC TGT AGC ACG CTT CCT GGA GGC AAA TAC GGG GCG CTT TCT
        Val Ser Ile Cys Ser Thr Leu Pro Gly Gly Lys Tyr Gly Ala Leu Ser
                        205                     210                     215

1146    GGT ACG TGC ATG GCA TCT GCG CAC GTT GCC GGA GCG GCT GCT TTG ATT
        Gly Thr Cys Met Ala Ser Ala His Val Ala Gly Ala Ala Ala Leu Ile
                        220                     225                     230

1194    CTT TCT AAG CAC CCG AAC TGG ACA AAC ACT CAA GTC CGC AGC AGT TTA
        Leu Ser Lys His Pro Asn Trp Thr Asn Thr Gln Val Arg Ser Ser Leu
                        235                     240                     245                     250

1242    GAA AAC ACC GCT ACA AAA CTT GGT GAT TCT TTC TAC TAT GGA AAA GGG
        Glu Asn Thr Ala Thr Lys Leu Gly Asp Ser Phe Tyr Tyr Gly Lys Gly
                        255                     260                     265

1290    CTG ATC AAC GTA GAA GCG GCA GCT CAG CAC CAC CAC CAC CAC CAC TAA
        Leu Ile Asn Val Glu Ala Ala Ala Gln His His His His His His ---
                        270                     275                     280

1338    AACATAAAAA ACCGGCCTTG GCCCCGCCGG TTTTTTATTA TTTTTCTTCC TCCGCATGTT

1398    CAATCCGCTC CATAATCGAC GGATGGCTCC CTCTGAAAAT TTTAACGAGA AACGGCGGGT

1458    TGACCCGGCT CAGTCCCGTA ACGGCCAAGT CCTGAAACGT CTCAATCGCC GCTTCCCGGT

1518    TTCCGGTCAG CTCAATGCCG TAACGGTCGG CGGCGTTTTC CTGATACCGG GAGACGGCAT

1578    TCGTAATCGG ATGGATCC
                       BamHI
```
*Deletion with respect to BPN' of amino acid 72-80 (Val-Ala-Ala-Leu-Asn-Asn-Ser-Ile-Gly); GTT GCG GCT
CTT AAT AAC TCA ATC GGT.

The invention claimed is:

1. A method for enzymatically synthesizing an (oligo)peptide, comprising:
coupling (a) an (oligo)peptide C-terminal ester or thioester and (b) an (oligo)peptide nucleophile having an N-terminally unprotected amine,
wherein the coupling is carried out in a fluid comprising water, and
wherein the coupling is catalyzed by a subtilisin BPN' variant or mutant, said variant or mutant comprising mutations, said mutations comprising:
a deletion of the calcium binding domain corresponding to amino acid corresponding to positions 75-83; and
a mutation at the amino acid position corresponding to S221, the mutation corresponding to S221C or S221selenocysteine;
wherein the amino acid positions are defined based upon the numbering of the amino acid sequence of SEQ ID NO:2, and wherein the subtilisin BPN' variant or mutant has enzymatic activity.

2. A method for enzymatically synthesizing a cyclic (oligo)peptide of at least 12 amino acids, comprising:
subjecting an (oligo)peptide C-terminal ester or thioester having an N-terminally unprotected amine to a cyclisation step wherein said cyclization is carried out in a fluid comprising water, and
wherein the cyclization is catalyzed by a subtilisin BPN' variant or mutant, said variant or mutant comprising mutations, said mutations comprising:
a deletion of the calcium binding domain corresponding to amino acid corresponding to positions 75-83; and
a mutation at the amino acid position corresponding to S221, the mutation being S221C or S221selenocysteine;
wherein the amino acid positions are defined based upon the numbering of the amino acid sequence of SEQ ID NO: 2, and wherein the subtilisin BPN' variant or mutant has enzymatic activity.

3. The method of claim 1, wherein the mutation at the amino acid position corresponding to S221 is S221C.

4. The method of claim 1, wherein the subtilisin BPN' variant or mutant comprises a mutation at the amino acid position corresponding to P225.

5. The method of claim 1 wherein the subtilisin BPN' variant or mutant, comprises one or more mutations, and wherein said mutations correspond to amino acid positions Q2, S3, P5, S9, I31, K43, M50, A73, E156, G166, G169, S188, Q206, N212, N218, T254 or Q271 of SEQ ID NO: 2.

6. The method of claim 5, wherein said one or more mutations correspond to Q2K, S3C, P5S, S9A, I31L, K43N, M50F, A73L, E156S, G166S, G169A, S188P, Q206C, N212G, N218S, T254A or Q271E.

7. The method of claim 6, wherein the subtilisin BPN' variant or mutant, comprises at least four of said mutations, and wherein said mutations correspond to Q2K, S3C, P5S, S9A, I31L, K43N, M50F, A73L, E156S, G166S, G169A, S188P, Q206C, N212G, N218S, T254A or Q271E.

8. The method of claim 7, wherein the subtilisin BPN' variant or mutant, comprises the mutations corresponding to Q2K, S3C, P5S, S9A, I31L, K43N, M50F, A73L, E156S, G166S, G169A, S188P, Q206C, N212G, N218S, T254A or Q271E.

9. The method of claim 1, wherein the subtilisin BPN' variant or mutant, comprises one or more mutations selected from the group of mutations at an amino acid position corresponding to N62, G100, S125, L126, G127, P129, N155, Y217, N218 or M222 of SEQ ID NO: 2.

10. The method of claim 9, wherein the subtilisin BPN' variant or mutant, contains a mutation at the position corresponding to M222 of SEQ ID NO: 2.

11. The method of claim 10, wherein said mutation at the position corresponding to M222 is M222G, M222P, M222N, M222E, M222Q or M222A.

12. The method of claim 9, wherein the subtilisin BPN' variant or mutant, comprises a mutation at the amino acid position corresponding to Y217 of SEQ ID NO: 2.

13. The method of claim 12, wherein the mutation at Y217 is Y217L, Y217N, Y217E, Y217G, Y217F, Y217S, Y217A or Y217H.

14. The method of claim 1, wherein the subtilisin BPN' variant or mutant, comprises at least one mutation, and wherein said mutation is at an amino acid position corresponding to Y104, I107, L126, S101, G102, G127, G128, L135, or P168 of SEQ ID NO: 2.

15. The method of claim 14, wherein said mutation is at an amino acid corresponding to Y104, I107 and L135.

16. The method of claim 1, wherein the (oligo)peptide C-terminal ester is defined by the formula peptide-(C=O)O—$CX_2$—C(=O)N—$R_1R_2$, each X independently representing a hydrogen atom or an alkyl group; and $R_1$ representing a hydrogen atom or an alkyl group and $R_2$ representing a hydrogen atom or an alkyl group or an amino acid or a peptide residue with a C-terminal carboxyamide or carboxylic acid functionality, optionally protected on the side-chain functionality of the amino acid or on one or more of the side-chain functionalities of the amino acids.

17. The method of claim 4, wherein said mutation corresponds to P225N, P225D, P225S, P225C, P225G, P225T, P225V, P225I, P225L, P225H or P225Q.

18. The method of claim 2, wherein the subtilisin BPN' variant or mutant comprises a mutation at the amino acid position corresponding to P225.

19. The method of claim 18, wherein said mutation corresponds to P225N, P225D, P225S, P225C, P225G, P225T, P225V, P225I, P225L, P225H or P225Q.

20. The method of claim 2, wherein the mutation at the amino acid position corresponding to S221 is S221C.

* * * * *